United States Patent
Xu et al.

(10) Patent No.: US 10,308,682 B2
(45) Date of Patent: Jun. 4, 2019

(54) INHIBITION OF TUMOR GROWTH WITH AGGREGATES OF SMALL MOLECULES

(71) Applicant: BRANDEIS UNIVERSITY, Waltham, MA (US)

(72) Inventors: Bing Xu, Newton, MA (US); Yi Kuang, Waltham, MA (US)

(73) Assignee: Brandeis University, Waltham, MA (US)

( * ) Notice: Subject to any disclaimer, the term of this patent is extended or adjusted under 35 U.S.C. 154(b) by 0 days.

(21) Appl. No.: 14/773,690

(22) PCT Filed: Mar. 6, 2014

(86) PCT No.: PCT/US2014/021129
§ 371 (c)(1),
(2) Date: Sep. 8, 2015

(87) PCT Pub. No.: WO2014/138367
PCT Pub. Date: Sep. 12, 2014

(65) Prior Publication Data
US 2016/0016994 A1      Jan. 21, 2016

Related U.S. Application Data

(60) Provisional application No. 61/773,296, filed on Mar. 6, 2013.

(51) Int. Cl.
| C07K 5/072 | (2006.01) |
| A61K 38/00 | (2006.01) |
| A61P 35/00 | (2006.01) |
| A61K 31/195 | (2006.01) |

(52) U.S. Cl.
CPC ........ C07K 5/06121 (2013.01); A61K 31/195 (2013.01)

(58) Field of Classification Search
CPC .......................... A61K 31/195; C07K 5/06121
See application file for complete search history.

(56) References Cited

U.S. PATENT DOCUMENTS

| 5,595,756 A * | 1/1997 | Bally .................... A61K 9/1272 264/4.1 |
| 2012/0142616 A1 | 6/2012 | Gao et al. |
| 2014/0148410 A1 | 5/2014 | Xu |

FOREIGN PATENT DOCUMENTS

| RU | 1568480 A1 * | 1/1994 | ........... A61K 31/195 |
| WO | 2010/151644 A2 | 12/2010 | |
| WO | 2012/166705 A2 | 12/2012 | |
| WO | 2012/166706 A2 | 12/2012 | |
| WO | 2014/138367 A1 | 9/2014 | |

OTHER PUBLICATIONS

Sporn, B and Suh, N, Chemoprevention of cancer, Carcinogenesis, 2000, 21, pp. 525-530.*
Auerbach. R. et al, Angiogenesis assays: Problems and pitfalls, Cancer and Metastasis Reviews, 2000, 19, pp. 167-172,.*
Gura, T. Systems for Identifying New Drugs Are Often Faulty, Science, 1997, 278, pp. 1041-1042.*
Jain R. K., Barriers to Drug Delivery in Solid Tumors, Scientific American, 1994, pp. 58-65.*
Cancer Drug Design and Discovery. Neidle, Stephen, ed., Elsevier/ACademic Press, 2008, p. 427-431.*
Cellular and Molecular Basis of Cancer from Merck Manual, 2008, pp. 1-5, accessed Nov. 7, 2012.*
Rudinger, Peptide Hormones, JA Parsons, Ed., 1976, pp. 1-7.*
SIGMA, 2004, pp. 1-2.*
Berendsen, A Glimpse of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-494.*
Bradley et al., Limits of Cooperativity in a Structurally Modular Protein: Response of the Notch Ankyrin Domain to Analogous Alanine Substitutions in Each Repeat, J. Mol. BIoL (2002) 324, 373-386.*
Gao et al, Enzyme-Instructed Molecular Self-assembly Confers Nanofibers and a Supramolecular Hydrogel of Taxol Derivative, J. Am. Chem. Soc., 2009, 131, pp. 13576-13577.*
Yang et al, Intracellular Enzymatic Formation of Nanofibers Results in Hydrogelation and Regulated Cell Death, Adv. Mater., 2007, 19, pp. 3152-3156.*
English translation of SU 1568480 A1, pp. 1-10, accessed Jul. 2016.*
PCT International Search Report and Written Opinion corresponding to PCT/US2014/021129, filed Mar. 6, 2014 (dated May 30, 2014).
Liang et al., "Supramolecular Hydrogel of a D-Amino Acid Dipeptide for Controlled Drug Release in Vivo," Langmuir 25(15):8419-422 (2009).
Gao et al., "Imaging Enzyme-Triggered Self-Assembly of Small Molecules Inside Live Cells," Nat Commun. 3:1033 (2012).
Li et al., "Molecular Nanofibers of Olsalazine Confer Supramolecular Hydrogels for Reductive Release of an Anti-Inflammatory Agent," J Am Chem Soc. 132(50):17707-709 (2010).
Zhang et al., "Versatile Small Molecule Motifs for Self-Assembly in Water and Formation of Biofunctional Supramolecular Hydrogels," Langmuir. 27(2):529-37 (2011).
Li et al., "The Conjugation of Nonsteroidal Anti-Inflammatory Drugs (NSAID) to Small Peptides for Generating Multifunctional Supramolecular Nanofibers/Hydrogels," Beilstein J. Org. Chem. 9:908-917 (2013).

(Continued)

Primary Examiner — Karlheinz R. Skowronek
Assistant Examiner — Li N Komatsu
(74) Attorney, Agent, or Firm — Pepper Hamilton LLP

(57) ABSTRACT

Disclosed herein are fibrillar molecular aggregates, which are morphologically and phenotypically similar to oligomers of aberrant proteins. The molecular aggregates, formed by self-assembly of small hydrophobic molecules, prevent the growth of microtubules. This unprecedented mechanism of "self-assembly to interfere with self-organization" allows inhibition of the growth of cancer cells.

18 Claims, 39 Drawing Sheets

Specification includes a Sequence Listing.

(56) References Cited

OTHER PUBLICATIONS

Li et al., "Introducing D-Amino Acid or Simple Glycoside into Small Peptides to Enable Supramolecular Hydrogelators to Resist Proteolysis," Langmuir. 28(37):13512-517 (2012).

Li et al., "'Molecular Trinity' for Soft Nanomaterials: Integrating Nucleobases, Amino Acids, and Glycosides to Construct Multifunctional Hydrogelators," Soft Matter. 8(10):2801-806 (2012).

Zhao et al., "A Novel Anisotropic Supramolecular Hydrogel with High Stability over a Wide PH Range," Langmuir. 27 (4):1510-12 (2011).

Li et al., "Supramolecular Nanofibers and Hydrogels of Nucleopeptides," Angew Chem Int Ed Engl. 50(40):9365-69 (2011).

\* cited by examiner

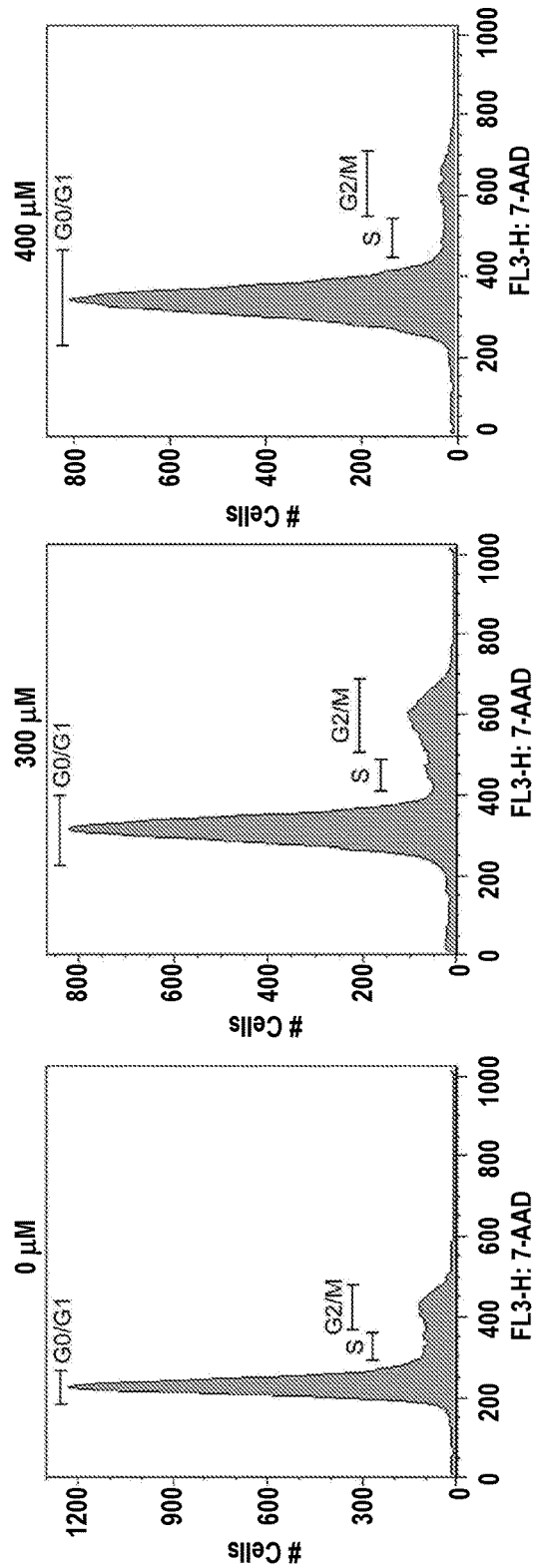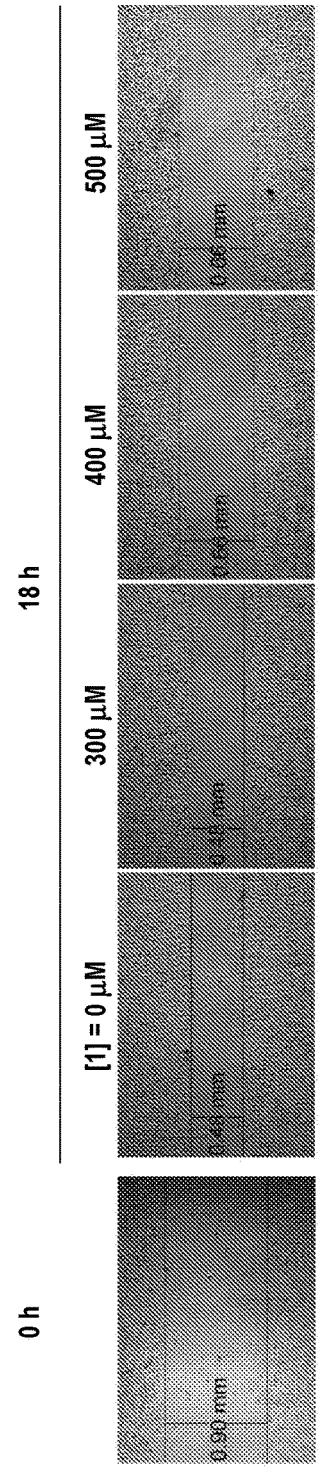
FIG. 3D
FIG. 3E

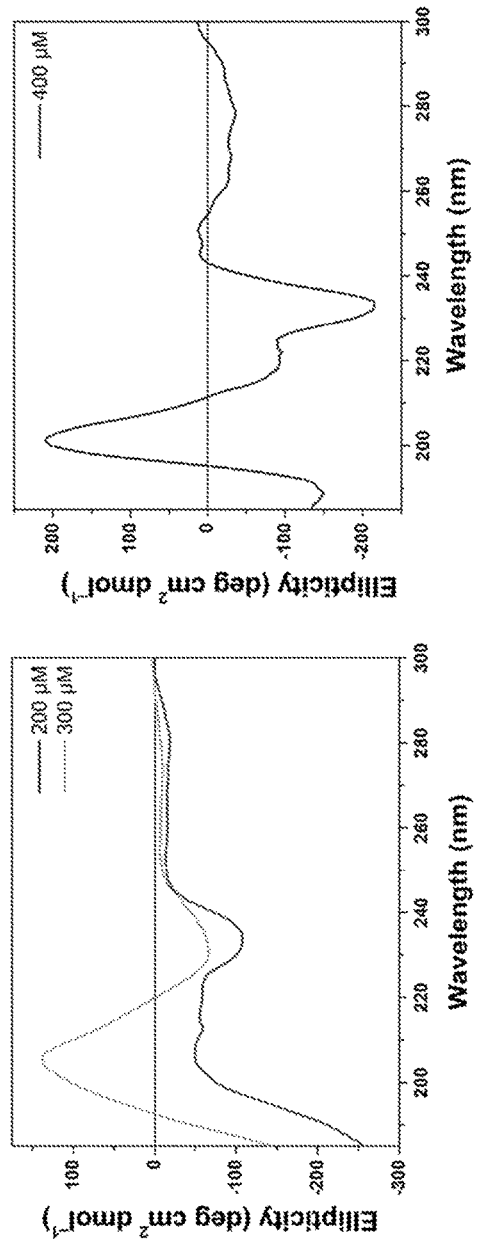
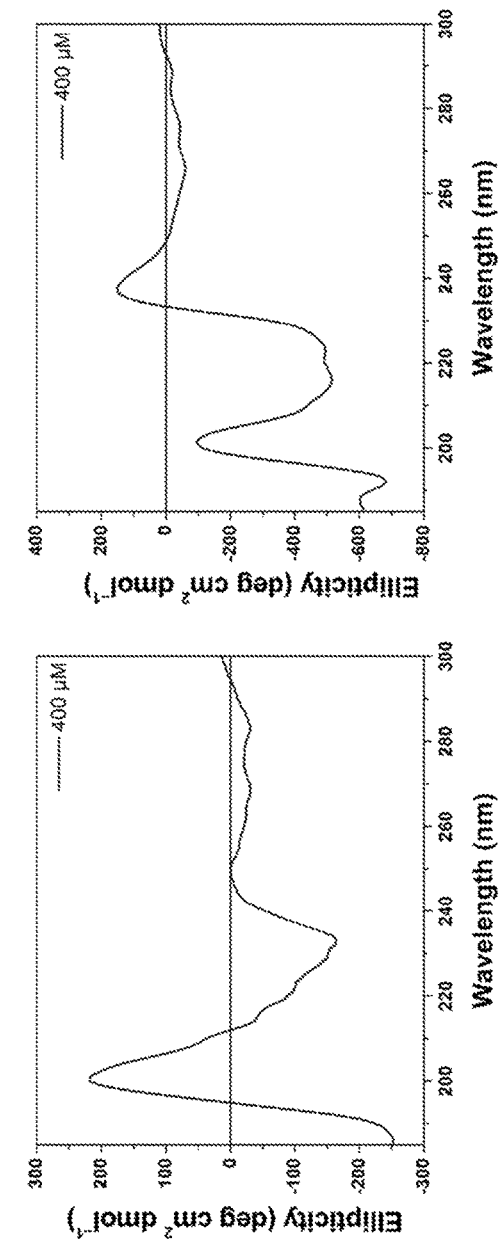
FIG. 13A, FIG. 13B, FIG. 13C, FIG. 13D

| Protein | Coverage (%) |
|---|---|
| BASP1 | 66.5 |
| CCT2 | 63.4 |
| TUBA4A | 56.5 |
| SERPINH1 | 54.4 |
| TUBB2C | 53.8 |
| FKBP4 | 52.1 |
| ATP5B | 51.2 |
| VIM | 50.9 |
| ENO1 | 50.4 |
| TUFM | 48.6 |
| NUDC | 48 |
| PDIA3 | 47.4 |
| G6PD | 45.9 |
| SSB | 45.6 |
| EIF4A1 | 45.3 |
| EIF4A3 | 45.3 |
| PSMC3 | 44.2 |
| GPI | 44.1 |
| BZW1 | 43.9 |
| DNAJA1 | 43.6 |
| PSMD11 | 42.8 |
| PDIA6 | 42.3 |
| EIF3E | 40.2 |
| ATP5A1 | 40 |

*FIG. 16*

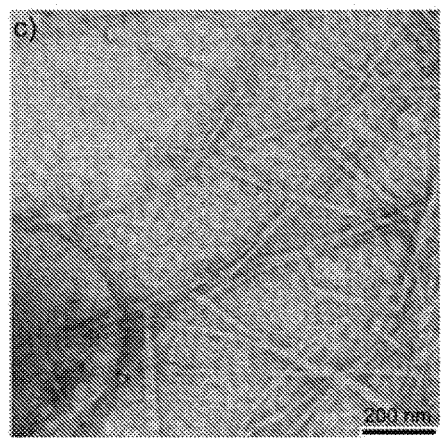
FIG. 22C
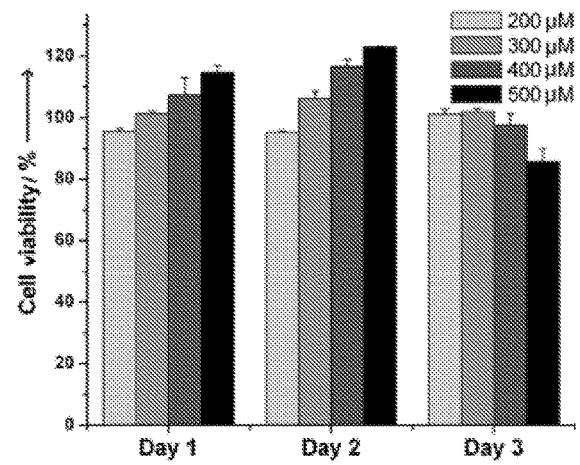
FIG. 22D
| Initial Concentration (uM) | Concentration after filtration (uM)[a] |
|---|---|
| 200 | 190 |
| 300 | 251 |
| 400 | 336 |
| 500 | 329 |
FIG. 23

| Protein name | Total peptide # | Peptide | SEQ ID NO: | Peptide # | Reference | Protein coverage (%) |
|---|---|---|---|---|---|---|
| Tubulin, beta | 135 | KEVDEQMLNVQNKN | 1 | 6 | TUBB2C_IPI:IPI 00007752.1 | 54.2 |
| | | KFWEVISDEHGIDPTGTYHGDSDLQLERI | 2 | 1 | | |
| | | KGHYTEGAELVDSVLDVVRK | 3 | 7 | | |
| | | KGHYTEGAELVDSVLDVVRKE | 4 | 1 | | |
| | | KLTTPTYGDLNHLVSATMSGVTTCLRF | 5 | 2 | | |
| | | KNMMAACDPRH | 6 | 2 | | |
| | | KNSSYFVEWIPNNVKT | 7 | 7 | | |
| | | KRISEQFTAMFRR | 8 | 1 | | |
| | | RALTVPELTQQMFDAKN | 9 | 5 | | |
| | | RAVLVDLEPGTMDSVRS | 10 | 3 | | |
| | | REIVHLQAGQCNQIGAKF | 11 | 2 | | |
| | | RIMNTFSVVPSPKV | 12 | 6 | | |
| | | RINVYYNEATGGKY | 13 | 3 | | |
| | | RISEQFTAMFRR | 14 | 4 | | |
| | | RLHFFMPGFAPLTSRG | 15 | 8 | | |
| | | RMSMKEVDEQMLNVQNKN | 16 | 4 | | |
| | | RSGPFGQIFRPDNFVFGQSGAGNNWAKG | 17 | 4 | | |
| | | RYLTVAAVFRG | 18 | 2 | | |
| | | KFWEVISDEHGIDPTGTYHGDSDLQLDRI | 19 | 1 | TUBB_IPI:IPI00 011654.2 | 23.2 |
| | | KMAVTFIGNSTAIQELFKR | 20 | 12 | | |
| | | RAILVDLEPGTMDSVRS | 21 | 6 | | |
| | | RALTVPELTQQVFDAKN | 22 | 8 | | |
| | | REIVHIQAGQCGNQIGAKF | 23 | 2 | | |
| | | RISVYYNEATGGKY | 24 | 2 | | |
| | | KFWEVISDEHGIDPAGGYVGDSALQLERI | 25 | 1 | TUBB6_IPI:IPI0 0641706.1 | 18.8 |
| | | KLTTPTYGDLNHLVSATMSGVTTSLRF | 26 | 3 | | |
| | | RALTVPELTQQMFDARN | 27 | 1 | | |
| | | RISEQFSAMFRR | 28 | 1 | | |
| | | KEVDEQMLAIQSKN | 29 | 2 | TUBB3_IPI:IPI0 0013683.2 | 16.7 |
| | | KLATPTYGDLNHLVSATMSGVTTSLRF | 30 | 1 | | |
| | | KMSSTFIGNSTAIQELFKR | 31 | 1 | | |
| | | RISVYYNEASSHKY | 32 | 1 | | |
| | | RYLTVATVFRG | 33 | 1 | | |

*FIG. 24A*

|  |  | Sequence | # | Count | Protein ID | |
|---|---|---|---|---|---|---|
|  |  | KIREEYPDRI | 34 | 1 | TUBB1_IPI:IPI00006510.1 | 6.4 |
|  |  | KLAVNMVPFPRL | 35 | 5 |  |  |
|  |  | RFPGQLNADLRK | 36 | 7 |  |  |
|  |  | RFPGQLNADLRKL | 37 | 2 |  |  |
|  |  | RKLAVNMVPFPRL | 38 | 1 |  |  |
|  |  | RAALVDLEPGTMDSVRS | 39 | 2 | TUBB6_IPI:IPI00646779.2 | 9.2 |
|  |  | RSGPFGQLFRPDNFIFGQTGAGNNWAKG | 40 | 1 |  |  |
|  |  | RALTVPELTQQMFDSKN | 41 | 1 | TUBB2A_IPI:IPI00013475.1 | 8.8 |
|  |  | RMNTFSVMPSPKV | 42 | 2 |  |  |
|  |  | RINVYYNEAAGNKY | 43 | 1 |  |  |
|  |  | KGHYTEGAELVDAVLDVVRK | 44 | 1 | TUBB4_IPI:IPI00023598.2 | 4.1 |
| Tubulin, alpha | 83 | KAYHEQLSVAEITNACFEPANQMVKC | 45 | 3 | TUBA4A_IPI:IPI00007750.1 | 56.9 |
|  |  | KDVNAAIAAIKT | 46 | 2 |  |  |
|  |  | KEIIDPVLDRI | 47 | 1 |  |  |
|  |  | KFDLMYAKR | 48 | 3 |  |  |
|  |  | KRAFVHWYVGEGMEEGEFSEARE | 49 | 1 |  |  |
|  |  | KTIGGGDDSFTTFFCETGAGKH | 50 | 1 |  |  |
|  |  | KVGINYQPPTVVPGGDLAKV | 51 | 6 |  |  |
|  |  | RAFVHWYVGEGMEEGEFSEARE | 52 | 5 |  |  |
|  |  | RAVCMLSNTTAIAEAWARL | 53 | 4 |  |  |
|  |  | RAVFVDLEPTVIDEIRN | 54 | 3 |  |  |
|  |  | REDMAALEKD | 55 | 1 |  |  |
|  |  | RFDGALNVDLTEFQTNLVPYPRI | 56 | 1 |  |  |
|  |  | RGHYTIGKE | 57 | 1 |  |  |
|  |  | RIHFPLATYAPVISAEKA | 58 | 11 |  |  |
|  |  | RLDHKFDLMYAKR | 59 | 3 |  |  |
|  |  | RLISQIVSSITASLRF | 60 | 3 |  |  |
|  |  | RLSVDYGKK | 61 | 1 |  |  |
|  |  | RLSVDYGKKS | 62 | 2 |  |  |
|  |  | RNLDIERPTYTNLNRL | 63 | 2 |  |  |
|  |  | RQLFHPEQLITGKE | 64 | 5 |  |  |
|  |  | RQLFHPEQLITGKEDAANNYARG | 65 | 2 |  |  |
|  |  | RRNLDIERPTYTNLNRL | 66 | 1 |  |  |
|  |  | KAYHEQLTVAEITNACFEPANQMVKC | 67 | 1 | TUBA1C_IPI:IPI00166768.3 | 23.9 |
|  |  | KDVNAAIATIKT | 68 | 2 |  |  |
|  |  | KEIIDLVLDRI | 69 | 1 |  |  |

FIG. 24B

| | | | | | | |
|---|---|---|---|---|---|---|
| | | KTIGGGDDSFNTFFSETGAGKH | 70 | 4 | | |
| | | RAVFVDLEPTVIDEVRT | 71 | 4 | TUBA1A_IPI:IPI 00180675.4 | 6.4 |
| | | KDYEEVGVDSVEGEGEEEGEEY | 72 | 3 | | |
| | | REDMAALEKDYEEVGVDSVEGEGEEEGEEY | 73 | 2 | | |
| | | KDYEEVGADSADGEDEGEEY | 74 | 1 | TUBA1C_IPI:IPI 00218343.4 | 6 |
| | | REDMAALEKDYEEVGADSADGEDEGEEY | 75 | 1 | | |
| | | RLIGQIVSSITASLRF | 76 | 1 | TUBA3D_IPI:IPI 00179709.4 | 3.1 |
| | | RQIFHPEQLITGKE | 77 | 1 | TUBA4B_IPI:IPI 00017454.4 | 5 |
| T-complex protein1 subunit beta | 50 | KEAVAMESYAKA | 78 | 3 | CCT2_IPI:IPI00 297779.7 | 63.4 |
| | | KILIANTGMDTDKIKI | 79 | 1 | | |
| | | KKIHPQTIIAGWRE | 80 | 1 | | |
| | | KKLGGSLADSYLDEGFLLDKK | 81 | 1 | | |
| | | KKLGGSLADSYLDEGFLLDKKI | 82 | 1 | | |
| | | KLAVEAVLRL | 83 | 1 | | |
| | | KLGGSLADSYLDEGFLLDKK | 84 | 1 | | |
| | | KLGGSLADSYLDEGFLLDKKI | 85 | 4 | | |
| | | KLIEEVMIGEDKL | 86 | 1 | | |
| | | KNIGVDNPAAKV | 87 | 1 | | |
| | | KVAEIEHAEKEKM | 88 | 1 | | |
| | | KVLVDMSRV | 89 | 1 | | |
| | | RAAHSEGNTTAGLDMRE | 90 | 3 | | |
| | | RDASLMVTNDGATILKN | 91 | 4 | | |
| | | REAESLIAKK | 92 | 1 | | |
| | | REALLSSAVDHGSDEVKF | 93 | 1 | | |
| | | REGTIGDMAILGITESFQVKR | 94 | 4 | | |
| | | RGATQQILDEAERS | 95 | 1 | | |
| | | RLALVTGGEIASTFDHPELVKL | 96 | 2 | | |
| | | RLKGSGNLEAIHIIKK | 97 | 1 | | |
| | | RLTSFIGAIAIGDLVKS | 98 | 1 | | |
| | | RMLPTIIADNAGYDSADLVAQLRA | 99 | 4 | | |
| | | RQDLMNIAGTTLSSKL | 100 | 4 | | |
| | | RQLIYNYPEQLFGAAGVMAIEHADFAGVERL | 101 | 3 | | |
| | | RQVLLSAAEAAEVILRV | 102 | 2 | | |
| | | RVQDDEVGDGTTSVTVLAAELLRE | 103 | 2 | | |
| Actin, beta | 44 | KDLYANTVLSGGTTMYPGIADRM | 104 | 13 | ACTB_IPI:IPI00 021439.1 | 36.5 |
| | | KLCYVALDFEQEMATAASSSSLEKS | 105 | 1 | | |

*FIG. 24C*

| | | KQEYDESGPSIVHRK | 106 | 4 | | |
|---|---|---|---|---|---|---|
| | | KYPIEHGIVTNWDDMEKI | 107 | 2 | | |
| | | RDIKEKLCYVALDFEQEMATAASSSSLEKS | 108 | 1 | | |
| | | RGYSFTTTAERE | 109 | 3 | | |
| | | RKDLYANTVLSGGTTMYPGIADRM | 110 | 6 | | |
| | | RTTGIVMDSGDGVTHTVPIYEGYALPHAILRL | 111 | 8 | | |
| | | RVAPEEHPVLLTEAPLNPKA | 112 | 6 | | |
| Vimentin | 37 | KFADLSEAANRN | 113 | 1 | VIM_IPI:IPI0041 8471.6 | 51.1 |
| | | KILLAELEQLKG | 114 | 1 | | |
| | | KILLAELEQLKGQGKS | 115 | 1 | | |
| | | KLQEEMLQRE | 116 | 2 | | |
| | | KLQEEMLQREEAENTLQSFRQ | 117 | 1 | | |
| | | KVELQELNDRF | 118 | 1 | | |
| | | RDGQVINETSQHHDDLE | 119 | 1 | | |
| | | RDNLAEDIMRL | 120 | 1 | | |
| | | REKLQEEMLQRE | 121 | 1 | | |
| | | REKLQEEMLQREEAENTLQSFRQ | 122 | 1 | | |
| | | REMEENFAVEAANYQDTIGRL | 123 | 3 | | |
| | | RETNLDSLPLVDTHSKR | 124 | 2 | | |
| | | RFANYIDKV | 125 | 1 | | |
| | | RISLPLPNFSSLNLRE | 126 | 2 | | |
| | | RKVESLQEEIAFLKK | 127 | 2 | | |
| | | RKVESLQEEIAFLKKL | 128 | 1 | | |
| | | RLGDLYEEEMRE | 129 | 2 | | |
| | | RLLQDSVDFSLADAINTEFKN | 130 | 3 | | |
| | | RLQDEIQNMKE | 131 | 1 | | |
| | | RLQDEIQNMKEEMARH | 132 | 1 | | |
| | | RQVDQLTNDKA | 133 | 1 | | |
| | | RRQVDQLTNDKA | 134 | 1 | | |
| | | RSLYASSPGGVYATRS | 135 | 1 | | |
| | | RTNEKVELQELNDRF | 136 | 2 | | |
| | | RTYSLGSALRPSTSRS | 137 | 1 | | |
| | | RVEVERDNLAEDIMRL | 138 | 2 | | |
| Protein Disulfide Isomerase Family A, Member 3 | 35 | KDASIVGFFDDSFSEAHSEFLKA | 139 | 1 | PDIA3_IPI:IPI00 025252.1 | 47.5 |
| | | KDLLIAYYDVDYEKN | 140 | 2 | | |
| | | KDPNIVIAKM | 141 | 1 | | |
| | | KFEDKTVAYTEQKM | 142 | 1 | | |
| | | KFVMQEEFSRD | 143 | 2 | | |
| | | KGSNYWRN | 144 | 1 | | |

*FIG. 24D*

| | | | | | | |
|---|---|---|---|---|---|---|
| | | KIFRDGEEAGAYDGPRT | 145 | 2 | | |
| | | KLNFAVASRK | 146 | 2 | | |
| | | KLSKDPNIVIAKM | 147 | 1 | | |
| | | KMDATANDVPSPYEVRG | 148 | 3 | | |
| | | KQAGPASVPLRT | 149 | 1 | | |
| | | KRLAPEYEAAATRL | 150 | 1 | | |
| | | KSEPIPESNDGPVKV | 151 | 1 | | |
| | | KTFSHELSDFGLESTAGEIPVVAIRT | 152 | 1 | | |
| | | KTVAYTEQKM | 153 | 1 | | |
| | | KYGVSGYPTLKI | 154 | 1 | | |
| | | RDGEEAGAYDGPRT | 155 | 2 | | |
| | | REATNPPVIQEEKPKK | 156 | 1 | | |
| | | RELSDFISYLQRE | 157 | 1 | | |
| | | RFLQDYFDGNLKR | 158 | 1 | | |
| | | RFLQDYFDGNLKRY | 159 | 1 | | |
| | | RGFPTIYFSPANKK | 160 | 2 | | |
| | | RKTFSHELSDFGLESTAGEIPVVAIRT | 161 | 1 | | |
| | | RLAPEYEAAATRL | 162 | 2 | | |
| | | RTADGIVSHLKK | 163 | 1 | | |
| | | RTADGIVSHLKKQ | 164 | 1 | | |
| Enolase 1, (alpha) | 35 | KAGYTDKVVIGMDVAASEFFRS | 165 | 1 | ENO1_IPI:IPI00 465248.5 | 50.7 |
| | | KDATNVGDEGGFAPNILENKE | 166 | 2 | | |
| | | KDATNVGDEGGFAPNILENKEGLELLKT | 167 | 1 | | |
| | | KDYPVVSIEDPFDQDDWGAWQKF | 168 | 2 | | |
| | | KFTASAGIQVVGDDLTVTNPKR | 169 | 3 | | |
| | | KLAMQEFMILPVGAANFRE | 170 | 10 | | |
| | | KLAQANGWGVMVSHRS | 171 | 1 | | |
| | | KSFIKDYPVVSIEDPFDQDDWGAWQKF | 172 | 1 | | |
| | | KTIAPALVSKK | 173 | 1 | | |
| | | KVVIGMDVAASEFFRS | 174 | 3 | | |
| | | RGNPTVEVDLFTSKG | 175 | 1 | | |
| | | RHIADLAGNSEVILPVPAFNVINGGSHAGNKL | 176 | 1 | | |
| | | RIEEELGSKA | 177 | 3 | | |
| | | RIGAEVYHNLKN | 178 | 1 | | |
| | | RSGKYDLDFKS | 179 | 1 | | |
| | | RSGKYDLDFKSPDDPSRY | 180 | 1 | | |
| | | RYISPDQLADLYKS | 181 | 2 | | |
| FK506 binding protein 4 | 34 | KAEASSGDHPTDTEMKEEQKS | 182 | 2 | FKBP4_IPI:IPI0 0219005.3 | 52.7 |
| | | KATESGAQSAPLPMEGVDISPKQ | 183 | 4 | | |
| | | KAWDIAIATMKV | 184 | 2 | | |

*FIG. 24E*

| | | KDKFSFDLGKGEVIKA | 185 | 1 | | |
|---|---|---|---|---|---|---|
| | | KESWEMNSEEKL | 186 | 1 | | |
| | | KFDSSLDRK | 187 | 1 | | |
| | | KFDSSLDRKD | 188 | 1 | | |
| | | KGEDLTEEEDGGIIRR | 189 | 1 | | |
| | | KGEHSIVYLKPSYAFGSVGKE | 190 | 2 | | |
| | | KIVSWLEYESSFSNEEAQKA | 191 | 1 | | |
| | | KKIVSWLEYESSFSNEEAQKA | 192 | 1 | | |
| | | KLEQSTIVKE | 193 | 1 | | |
| | | KLYANMFERL | 194 | 2 | | |
| | | KVLQLYPNNKA | 195 | 2 | | |
| | | REGTGTEMPMIGDRV | 196 | 3 | | |
| | | RFEIGEGENLDLPYGLERA | 197 | 3 | | |
| | | RGEAHLAVNDFELARA | 198 | 1 | | |
| | | RGEGYAKPNEGAIVEVALEGYYKD | 199 | 1 | | |
| | | RGEGYAKPNEGAIVEVALEGYYKDKL | 200 | 1 | | |
| | | RRGEAHLAVNDFELARA | 201 | 1 | | |
| | | RVFVHYTGWLLDGTKF | 202 | 2 | | |
| Glucose-6-phosphate dehydrogenase | 31 | KEMVQNLMVLRF | 203 | 2 | G6PD_IPI:IPI00216008.4 | 45.8 |
| | | KGYLDDPTVPRG | 204 | 1 | | |
| | | KKPGMFFNPEESELDLTYGNRY | 205 | 3 | | |
| | | KLKLEDFFARN | 206 | 1 | | |
| | | KLPDAYERL | 207 | 1 | | |
| | | KRNELVIRV | 208 | 1 | | |
| | | RDGLLPENTFIVGYARS | 209 | 2 | | |
| | | REELFQGDAFHQSDTHIFIIMGASGDLAKK | 210 | 1 | | |
| | | RGGYFDEFGIIRG | 211 | 1 | | |
| | | RGPTEADELMKR | 212 | 1 | | |
| | | RGPTEADELMKRV | 213 | 1 | | |
| | | RGSTTATFAAVVLYVENERW | 214 | 2 | | |
| | | RIFGPIWNRD | 215 | 1 | | |
| | | RIIVEKPFGRD | 216 | 1 | | |
| | | RLFYLALPPTVYEAVTKN | 217 | 2 | | |
| | | RLNSHMNALHLGSQANRL | 218 | 1 | | |
| | | RLSNHISSLFRE | 219 | 2 | | |
| | | RLTVADIRK | 220 | 1 | | |
| | | RNSYVAGQYDDAASYQRL | 221 | 3 | | |
| | | RVGFQYEGTYKW | 222 | 1 | | |
| | | RVQPNEAVYTKM | 223 | 1 | | |
| | | RWDGVPFILRC | 224 | 1 | | |

*FIG. 24F*

| Serpin peptidase inhibitor, clade H | 30 | KAATLAERS | 225 | 1 | SERPINH1_IPI: IPI00032140.4 | 54.8 |
|---|---|---|---|---|---|---|
| | | KAVAISLPKG | 226 | 1 | | |
| | | KAVLSAEQLRD | 227 | 1 | | |
| | | KGVVEVTHDLQKH | 228 | 2 | | |
| | | KHLAGLGLTEAIDKN | 229 | 2 | | |
| | | KHLAGLGLTEAIDKNKA | 230 | 2 | | |
| | | KKAVAISLPKG | 231 | 1 | | |
| | | KKPAAAAAPGTAEKL | 232 | 2 | | |
| | | KLFYADHPFIFLVRD | 233 | 1 | | |
| | | KLQIVEMPLAHKL | 234 | 2 | | |
| | | KLSSLIILMPHHVEPLERL | 235 | 2 | | |
| | | RDEEVHAGLGELLRS | 236 | 2 | | |
| | | RDTQSGSLLFIGRL | 237 | 1 | | |
| | | RLYGPSSVSFADDFVRS | 238 | 1 | | |
| | | RSAGLAFSLYQAMAKD | 239 | 1 | | |
| | | RSALQSINEWAAQTTDGKL | 240 | 2 | | |
| | | RSALQSINEWAAQTTDGKLPEVTKD | 241 | 1 | | |
| | | RSALQSINEWAAQTTDGKLPEVTKDVERT | 242 | 1 | | |
| | | RSYTVGVMMMHRT | 243 | 1 | | |
| | | RTDGALLVNAMFFKPHWDEKF | 244 | 1 | | |
| | | RTGLYNYYDDEKE | 245 | 1 | | |
| | | RTGLYNYYDDEKEKL | 246 | 1 | | |
| Eukaryotic translation elongation factor 1 alpha 2 | 29 | KEGNASGVSLLEALDTILPPTRPTDKPLRL | 247 | 1 | EEF1A2_IPI:IPI 00014424.1 | 30.2 |
| | | KEVSAYIKK | 248 | 1 | | |
| | | KFEKEAAEMGKG | 249 | 2 | | |
| | | KIGGIGTVPVGRV | 250 | 3 | | |
| | | KQLIVGVNKM | 251 | 2 | | |
| | | KSTTTGHLIYKC | 252 | 3 | | |
| | | KSVEMHHEALSEALPGDNVGFNVKN | 253 | 1 | | |
| | | KTHINIVVIGHVDSGKS | 254 | 8 | | |
| | | KYAWVLDKL | 255 | 3 | | |
| | | REHALLAYTLGVKQ | 256 | 4 | | |
| | | RQTVAVGVIKN | 257 | 1 | | |
| Eukaryotic translation initiation factor 4A1 | 27 | KATQALVLAPTRE | 258 | 1 | EIF4A1_IPI:IPI0 0025491.1 | 45.6 |
| | | KDQIYDIFQKL | 259 | 1 | | |
| | | KEELTLEGIRQ | 260 | 1 | | |
| | | KGVAINMVTEEDKRT | 261 | 1 | | |
| | | KGYDVIAQAQSGTGKT | 262 | 1 | | |
| | | KKEELTLEGIRQ | 263 | 1 | | |
| | | KLNSNTQVVLLSATMPSDVLEVTKK | 264 | 2 | | |

FIG. 24G

| | | | | | | |
|---|---|---|---|---|---|---|
| | | KLNSNTQVVLLSATMPSDVLEVTKKF | 265 | 1 | | |
| | | KLQMEAPHIIVGTPGRV | 266 | 2 | | |
| | | KMFVLDEADEMLSRG | 267 | 3 | | |
| | | RDFTVSAMHGDMDQKE | 268 | 1 | | |
| | | RELAQQIQKV | 269 | 1 | | |
| | | RENYIHRI | 270 | 1 | | |
| | | RGFKDQIYDIFQKL | 271 | 1 | | |
| | | RGIDVQQVSLVINYDLPTNRE | 272 | 1 | | |
| | | RKGVAINMVTEEDKRT | 273 | 2 | | |
| | | RQFYINVERE | 274 | 2 | | |
| | | RVFDMLNRR | 275 | 3 | | |
| | | RVLITTDLLARG | 276 | 1 | | |
| Kappa-actin | 26 | KDLYANTVLSGGSTMYPGIADRM | 277 | 1 | ACTBL2_IPI:IPI 00003269.1 | 25 |
| | | KIIAPPERKY | 278 | 1 | | |
| | | RDLTDYLMKI | 279 | 4 | | |
| | | RHQGVMVGMGQKD | 280 | 11 | | |
| | | RSYELPDGQVITIGNERF | 281 | 8 | | |
| | | RTTGIVMDSGDGVTHIVPIYEGYALPHAILRL | 282 | 1 | | |
| Glucose-6-phosphate isomerase | 25 | KEFGIDPQNMFEFWDWVGGRY | 283 | 2 | GPI_IPI:IPI0002 7497.5 | 45 |
| | | KEWFLQAAKD | 284 | 1 | | |
| | | KHFVALSTNTTKV | 285 | 2 | | |
| | | KILLANFLAQTEALMRG | 286 | 3 | | |
| | | KLTPFMLGALVAMYEHKI | 287 | 1 | | |
| | | KNLVTEDVMRM | 288 | 1 | | |
| | | KNLVTEDVMRMLVDLAKS | 289 | 1 | | |
| | | KSPEDLERL | 290 | 1 | | |
| | | KTFTTQETITNAETAKE | 291 | 1 | | |
| | | KTITDVINIGIGGSDLGPLMVTEALKPYSSGGP RV | 292 | 1 | | |
| | | KTLAQLNPESSLFIIASKT | 293 | 2 | | |
| | | KVFEGNRPTNSIVFTKL | 294 | 1 | | |
| | | KVKEFGIDPQNMFEFWDWVGGRY | 295 | 1 | | |
| | | RFAAYFQQGDMESNGKY | 296 | 2 | | |
| | | RMLVDLAKS | 297 | 1 | | |
| | | RSNTPILVDGKD | 298 | 1 | | |
| | | RSNTPILVDGKDVMPEVNKV | 299 | 1 | | |
| | | RVDHQTGPIVWGEPGTNGQHAFYQLIHQGTK M | 300 | 1 | | |
| | | RVWYVSNIDGTHIAKT | 301 | 1 | | |
| Tu translation elongation factor, mitochondrial | 24 | KADAVQDSEMVELVELEIRE | 302 | 4 | TUFM_IPI:IPI00 027107.5 | 48.6 |
| | | KELAMPGEDLKF | 303 | 1 | | |

*FIG. 24H*

| | | | | | | |
|---|---|---|---|---|---|---|
| | | KILAEGGGAKF | 304 | 1 | | |
| | | KKYEEIDNAPEERA | 305 | 1 | | |
| | | KLLDAVDTYIPVPARD | 306 | 1 | | |
| | | KTTLTAAITKI | 307 | 1 | | |
| | | KVEAQVYILSKE | 308 | 1 | | |
| | | RAEAGDNLGALVRG | 309 | 1 | | |
| | | RDKPHVNVGTIGHVDHGKT | 310 | 1 | | |
| | | RDLEKPFLLPVEAVYSVPGRG | 311 | 2 | | |
| | | REHLLLARQ | 312 | 1 | | |
| | | RELLTEFGYKG | 313 | 1 | | |
| | | RGITINAAHVEYSTAARH | 314 | 1 | | |
| | | RGTVVTGTLERG | 315 | 1 | | |
| | | RIILPPEKELAMPGEDLKF | 316 | 1 | | |
| | | RQIGVEHVVVYVNKA | 317 | 1 | | |
| | | RTIGTGLVTNTLAMTEEEKN | 318 | 3 | | |
| | | RTVVTGIEMFHKS | 319 | 1 | | |
| Actin, alpha | 23 | KAGFAGDDAPRA | 320 | 3 | ACTA2_IPI:IPI0 0008603.1 | 21 |
| | | KDSYVGDEAQSKR | 321 | 2 | | |
| | | KEITALAPSTMKI | 322 | 6 | | |
| | | KQEYDEAGPSIVHRK | 323 | 3 | | |
| | | KYPIEHGIITNWDDMEKI | 324 | 5 | | |
| | | RAVFPSIVGRPRH | 325 | 1 | | |
| | | KDSYVGHEAQSKR | 326 | 1 | ACTA2_IPI:IPI0 0927545.1 | 3.3 |
| | | KDLYANNVMSGGTTMYPGIADRM | 327 | 1 | ACTA1_IPI:IPI0 0021428.1 | 8.5 |
| | | KIWHHTFYNELRV | 328 | 1 | | |
| Chaperonin containing TCP1, subunit 7 (eta) | 22 | KALEIIPRQ | 329 | 1 | CCT7_IPI:IPI00 018465.1 | 34.1 |
| | | KATISNDGATILKL | 330 | 1 | | |
| | | KLLDVVHPAAKT | 331 | 1 | | |
| | | KLPIGDVATQYFADRD | 332 | 1 | | |
| | | KMVVDAVMMLDDLLQLKM | 333 | 5 | | |
| | | KNDSVVAGGGAIEMELSKY | 334 | 2 | | |
| | | KQQLLIGAYAKA | 335 | 1 | | |
| | | KSQDAEVGDGTTSVTLLAAEFLKQ | 336 | 2 | | |
| | | KTFSYAGFEMQPKK | 337 | 2 | | |
| | | KVQGGALEDSQLVAGVAFKK | 338 | 2 | | |
| | | RGGAEQFMEETERS | 339 | 2 | | |
| | | RSTVDAPTAAGRG | 340 | 1 | | |
| | | RVHTVEDYQAIVDAEWNILYDKLEKI | 341 | 1 | | |
| Integrin-linked | 22 | KGIEILTDMSRPVELSDRE | 342 | 3 | ILK- | 33.8 |

*FIG. 24I*

| | | | | | | |
|---|---|---|---|---|---|---|
| kinase | | KGIEILTDMSRPVELSDRETLLNSATTSLNSKV | 343 | 1 | 2_IPI:IPI003 02927.6 | |
| | | KLVIEEAERS | 344 | 1 | | |
| | | KMIQDGKGDVTITNDGATILKQ | 345 | 2 | | |
| | | KTDMDNQIVVSDYAQMDRV | 346 | 4 | | |
| | | KVIDPATATSVDLRD | 347 | 2 | | |
| | | KVSNSGITRV | 348 | 2 | | |
| | | KVVSQYSSLLSPMSVNAVMKV | 349 | 2 | | |
| | | RAFADAMEVIPSTLAENAGLNPISTVTELRN | 350 | 2 | | |
| | | RALIAGGGAPEIELALRL | 351 | 1 | | |
| | | RAYILNLVKQ | 352 | 1 | | |
| | | RDALSDLALHFLNKM | 353 | 1 | | |
| Phosphoglycerate dehydrogenase | 22 | KFMGTELNGKT | 354 | 1 | PHGDH_IPI:IPI 00011200.5 | 31 |
| | | KILQDGGLQVVEKQ | 355 | 1 | | |
| | | KQADVNLVNAKL | 356 | 1 | | |
| | | KQHVTEAFQFHF | 357 | 2 | | |
| | | KTLGILGLGRI | 358 | 1 | | |
| | | KVTADVINAAEKL | 359 | 2 | | |
| | | RAGTGVDNVDLEAATRK | 360 | 2 | | |
| | | RALQSGQCAGAALDVFTEEPPRDRA | 361 | 1 | | |
| | | RCGEEIAVQFVDMVKG | 362 | 1 | | |
| | | RDLPLLLFRT | 363 | 1 | | |
| | | RGGIVDEGALLRA | 364 | 2 | | |
| | | RQIPQATASMKD | 365 | 1 | | |
| | | RTQTSDPAMLPTMIGLLAEAGVRL | 366 | 6 | | |
| Sjogren syndrome antigen B (autoantigen La) | 21 | KDANNGNLQLRN | 367 | 1 | SSB_IPI:IPI000 09032.1 | 45.6 |
| | | KEVTWEVLEGEVEKE | 368 | 1 | | |
| | | KGFPTDATLDDIKEWLEDKG | 369 | 1 | | |
| | | KGFPTDATLDDIKEWLEDKGQVLNIQMRR | 370 | 1 | | |
| | | KGQVLNIQMRR | 371 | 1 | | |
| | | KGSIFVVFDSIESAKK | 372 | 1 | | |
| | | KIIEDQQESLNKW | 373 | 2 | | |
| | | KKFVETPGQKY | 374 | 1 | | |
| | | KLDEGWVPLEIMIKF | 375 | 2 | | |
| | | KLEEDAEMKS | 376 | 1 | | |
| | | KQKLEEDAEMKS | 377 | 1 | | |
| | | KSKAELMEISEDKTKI | 378 | 1 | | |
| | | KYKETDLLILFKD | 379 | 1 | | |
| | | KYKETDLLILFKDDYFAKK | 380 | 1 | | |
| | | REDLHILFSNHGEIKW | 381 | 1 | | |
| | | RLTTDFNVIVEALSKS | 382 | 1 | | |

*FIG. 24J*

| | | RNKEVTWEVLEGEVEKE | 383 | 1 | | |
| --- | --- | --- | --- | --- | --- | --- |
| | | RSPSKPLPEVTDEYKNDVKN | 384 | 2 | | |
| nudC nuclear distribution protein | 21 | KDAENHEAQLKN | 385 | 1 | NUDC_IPI:IPI00550746.4 | 48 |
| | | KDMVVDIQRR | 386 | 1 | | |
| | | KELTDEEAERL | 387 | 1 | | |
| | | KELTDEEAERLQLEIDQKK | 388 | 1 | | |
| | | KFMDQHPEMDFSKA | 389 | 1 | | |
| | | KGQPAIIDGELYNEVKV | 390 | 1 | | |
| | | KKDAENHEAQLKN | 391 | 1 | | |
| | | KLITQTFSHHNQLAQKT | 392 | 1 | | |
| | | KLKPNLGNGADLPNYRW | 393 | 3 | | |
| | | KLSDLDSETRS | 394 | 1 | | |
| | | KSMGLPTSDEQKK | 395 | 2 | | |
| | | KTDFFIGGEEGMAEKL | 396 | 2 | | |
| | | KVEESSWLIEDGKV | 397 | 1 | | |
| | | KVVTVHLEKI | 398 | 1 | | |
| | | RKTDFFIGGEEGMAEKL | 399 | 1 | | |
| | | RLQLEIDQKK | 400 | 1 | | |
| | | RLVSSDPEINTKK | 401 | 1 | | |
| Inosine 5'-monophosphate dehydrogenase 2 | 21 | KALALGASTVMMGSLLAATTEAPGEYFFSDGIRL | 402 | 1 | IMPDH2_IPI:IPI00291510.3 | 37.7 |
| | | KDKYPNLQVIGGNVVTAAQAKN | 403 | 2 | | |
| | | KGKLPIVNEDDELVAIIART | 404 | 2 | | |
| | | KNLIDAGVDALRV | 405 | 2 | | |
| | | KREDLVVAPAGITLKE | 406 | 2 | | |
| | | KVAQGVSGAVQDKG | 407 | 2 | | |
| | | KVSEYARR | 408 | 1 | | |
| | | KYEQGFITDPVVLSPKD | 409 | 1 | | |
| | | REDLVVAPAGITLKE | 410 | 1 | | |
| | | RFGVPVIADGGIQNVGHIAKA | 411 | 1 | | |
| | | RGMGSLDAMDKH | 412 | 1 | | |
| | | RLVGIISSRD | 413 | 1 | | |
| | | RRFGVPVIADGGIQNVGHIAKA | 414 | 1 | | |
| | | RTSSAQVEGGVHSLHSYEKR | 415 | 2 | | |
| | | RYFSEADKIKV | 416 | 1 | | |
| Brain abundant, membrane attached signal protein 1[a] | 21 | KAEGAATEEEGTPKE | 417 | 3 | BASP1_IPI:IPI00299024.9 | 66.5 |
| | | KAEGAATEEEGTPKESEPQAAAEPAEAKE | 418 | 1 | | |
| | | KAEPEKTEGAAEAKA | 419 | 1 | | |
| | | KAEPPKAPEQEQAAPGPAAGGEAPKA | 420 | 5 | | |
| | | KAPEQEQAAPGPAAGGEAPKA | 421 | 1 | | |

FIG. 24K

| | | | | | | |
|---|---|---|---|---|---|---|
| | | KAQGPAASAEEPKPVEAPAANSDQTVTVKE | 422 | 4 | | |
| | | KETPAATEAPSSTPKA | 423 | 1 | | |
| | | KGYNVNDEKA | 424 | 1 | | |
| | | KKAEGAATEEEGTPKE | 425 | 1 | | |
| | | KKTEAPAAPAAQETKS | 426 | 1 | | |
| | | KSDGAPASDSKPGSSEAAPSSKE | 427 | 2 | | |
| Eukaryotic translation elongation factor 1 alpha 1 | 21 | KDGNASGTTLLEALDCILPPTRPTDKPLRL | 428 | 2 | EEF1A1_IPI:IPI 00025447.8 | 23.8 |
| | | KEVSTYIKK | 429 | 1 | | |
| | | KSGDAAIVDMVPGKPMCVESFSDYPPLGRF | 430 | 5 | | |
| | | KYYVTIIDAPGHRD | 431 | 4 | | |
| | | RVETGVLKPGMVVTFAPVNVTTEVKS | 432 | 8 | | |
| | | RYEEIVKE | 433 | 1 | | |
| ATP synthase, H+ transporting, mitochondrial F1 complex, alpha subunit 1 | 20 | KAVDSLVPIGRG | 434 | 1 | ATP5A1_IPI:IPI 00440493.2 | 40 |
| | | KEIVTNFLAGFEA | 435 | 1 | | |
| | | KFENAFLSHVVSQHQALLGTIRA | 436 | 1 | | |
| | | KGIRPAINVGLSVSRV | 437 | 1 | | |
| | | KGMSLNLEPDNVGVVVFGNDKL | 438 | 2 | | |
| | | KHALIIYDDLSKQ | 439 | 1 | | |
| | | KQGQYSPMAIEEQVAVIYAGVRG | 440 | 3 | | |
| | | KTGTAEMSSILEERI | 441 | 1 | | |
| | | KTSIAIDTIINQKR | 442 | 1 | | |
| | | REAYPGDVFYLHSRL | 443 | 1 | | |
| | | REVAAFAQFGSDLDAATQQLLSRG | 444 | 2 | | |
| | | RILGADTSVDLEETGRV | 445 | 2 | | |
| | | RNVQAEEMVEFSSGLKG | 446 | 1 | | |
| | | RVLSIGDGIARV | 447 | 1 | | |
| | | RVVDALGNAIDGKG | 448 | 1 | | |
| Fascin homolog 1, actin-bundling protein | 20 | KKNGQLAASVETAGDSELFLMKL | 449 | 1 | FSCN1_IPI:IPI0 0163187.1 | 37.5 |
| | | KLINRPIIVFRG | 450 | 1 | | |
| | | KNGQLAASVETAGDSELFLMKL | 451 | 1 | | |
| | | KVNASASSLKK | 452 | 1 | | |
| | | KVNASASSLKKK | 453 | 1 | | |
| | | KYLTAEAFGFKV | 454 | 1 | | |
| | | KYWTLTATGGVQSTASSKN | 455 | 1 | | |
| | | RDVPWGVDSLITLAFQDQRY | 456 | 1 | | |
| | | RFLIVAHDDGRW | 457 | 2 | | |
| | | RKVTGTLDANRSSYDVFQLEFNDGAYNIKD | 458 | 1 | | |
| | | RLVARPEPATGYTLEFRS | 459 | 2 | | |
| | | RQGMDLSANQDEETDQETFQLEIDRD | 460 | 1 | | |
| | | RQGMDLSANQDEETDQETFQLEIDRDTKK | 461 | 2 | | |

*FIG. 24L*

| | | RSSYDVFQLEFNDGAYNIKD | 462 | 2 | | |
| --- | --- | --- | --- | --- | --- | --- |
| | | RWSLQSEAHRR | 463 | 1 | | |
| | | RYSVQTADHRF | 464 | 1 | | |
| Eukaryotic translation initiation factor 4A3 | 20 | KEQIYDVYRY | 465 | 1 | EIF4A3_IPI:IPI0 0009328.4 | 45.3 |
| | | KFMTDPIRI | 466 | 1 | | |
| | | KGRDVIAQSQSGTGKT | 467 | 2 | | |
| | | KLDYGQHVVAGTPGRV | 468 | 2 | | |
| | | KMLVLDEADEMLNKG | 469 | 1 | | |
| | | KRDELTLEGIKQ | 470 | 1 | | |
| | | KRKVDWLTEKM | 471 | 1 | | |
| | | RDIEQYYSTQIDEMPMNVADLI | 472 | 1 | | |
| | | RDVIAQSQSGTGKT | 473 | 1 | | |
| | | REANFTVSSMHGDMPQKE | 474 | 1 | | |
| | | RELAVQIQKG | 475 | 1 | | |
| | | RETQALILAPTRE | 476 | 1 | | |
| | | RGIYAYGFEKPSAIQQRA | 477 | 2 | | |
| | | RGLDVPQVSLIINYDLPNNRE | 478 | 1 | | |
| | | RKLDYGQHVVAGTPGRV | 479 | 1 | | |
| | | RLLKEEDMTKV | 480 | 1 | | |
| | | RVLISTDVWARG | 481 | 1 | | |

FIG. 24M

INHIBITION OF TUMOR GROWTH WITH AGGREGATES OF SMALL MOLECULES

RELATED APPLICATIONS

This application claims the benefit of priority to U.S. Provisional Patent Application Ser. No. 61/773,296, filed Mar. 6, 2013; the contents of which are hereby incorporated by reference.

GOVERNMENT SUPPORT

This invention was made with government support under R01-CA142746 awarded by the National Institutes of Health. The government has certain rights in the invention.

BACKGROUND OF THE INVENTION

Cancer and Alzheimer's disease are major threats to the public health. While both diseases are still being understood, epidemiological and clinical studies suggest that there is an inverse association between cancer and Alzheimer's disease. The intriguing inverse association has stimulated the hope that the understanding of the mechanisms underlying the inverse association may lead to novel therapies for both diseases. Several plausible biological mechanisms have been postulated. For example, several groups have suggested that cancer and Alzheimer's disease may share same genes (e.g., TP53 and PIN1) and biological pathways (e.g., Wnt) related to activation and deregulation of the cell cycle. While the genetic links between cancer and Alzheimer's disease are biological plausibility that contributes to the observed inverse comorbidity, the complexity of the two groups of diseases obviously is beyond genetic definition, suggesting that other processes and mechanisms deserve serious consideration and rigorous examination.

In fact, after long debates about the causative agents of Alzheimer's disease, now it is suggested that amyloid oligomers are the most neurotoxic species. Recent studies also suggest that the early aggregates of misfolded non-disease-associated proteins and oligomers of disease-associated proteins (e.g., Aβs) exhibit similar inherent cytotoxicity, an important mechanistic advance that implies a common mechanism of the cytotoxicity of the aggregates. Since the aggregation of proteins (especially aberrant proteins), which represents a kinetically trapped state, is not directly defined at the genetic level, the elucidation of the molecular mechanism of the cytotoxicity of the aggregates may provide new information that eludes genetic studies. Despite its potential significance, the common origin of the cytotoxicity of the aggregates of aberrant proteins remains to be established.

SUMMARY OF THE INVENTION

In certain embodiments, the invention relates to a method of treating or preventing cancer comprising the step of administering to a subject in need thereof a plurality of hydrophobic, self-assembling monomers.

In certain embodiments, the invention relates to a method of retarding or preventing the growth of a microtubule comprising the step of contacting tubulin with a plurality of hydrophobic, self-assembling monomers.

In certain embodiments, the invention relates to any one of the aforementioned methods, wherein the hydrophobic, self-assembling monomer is represented by Formula I:

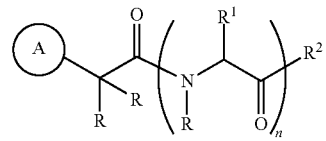

wherein, independently for each occurrence,

is aryl, heteroaryl, aralkyl, or heteroaralkyl;
R is H or alkyl;
$R^1$ is aralkyl or heteroaralkyl;
$R^2$ is H, alkyl, —OR, or —$NR_2$;
n is 1, 2, 3, 4, 5, 6, 7, 8, 9, 10, 11, 12, 13, 14, 15, 16, 17, 18, 19, or 20.

BRIEF DESCRIPTION OF THE FIGURES

FIG. 13 depicts CD spectra showing the polymorphic structures of nanofibers of 1. (a) As 1 exists mostly in monomeric form at low concentrations, the CD spectra are always consistent (200 μM=bottom line; 300 μM=top line). (b, c and d) At 400 μM, 1 displaces various CD spectra, indicating the fibril aggregates of 1 exist in more than one morphology.

FIG. 16 tabulates the major components of the proteins (40 to 70 kDa on SDS-PAGE) pulled-down by hydrogel formed by 1 measured by protein mass-spectrometry. Tubulin proteins are TUBA4A and TUBB2C.

FIG. 23 tabulates the concentrations of 1 after filtration. $^a$Following filtration, the solutions of 1 were diluted three-fold by MeOH to ensure complete dissolution of 1. The concentration of 1 was calculated from the absorbance of the solution at 260 nm.

FIG. 24 tabulates the protein composition (40 kDa to 70 kDa on SDS-PAGE) pulled-down by hydrogel formed by 1.

DETAILED DESCRIPTION OF THE INVENTION

Overview

Figure 1A:
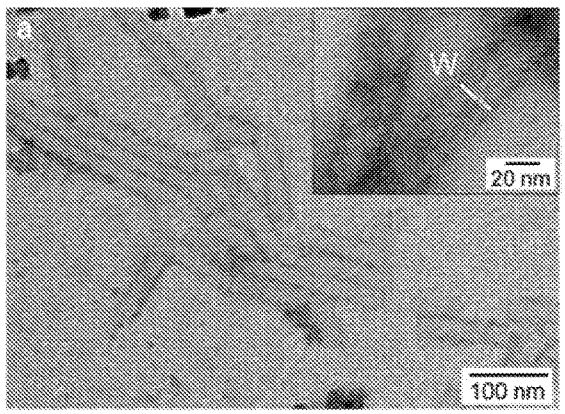
FIG. 1 depicts characteristics of fibrillar aggregates of 1. (a) Negative-stained TEM images of the solution of 1 at 400 μM and (b) the histogram of the length distribution of fibrillar aggregates according to the TEM images of 1 at 400 μM. (c) The plot of the heat release, measured by ITC, from the dilution of the solution of 1 at different concentrations. Data are presented as mean±SD. (d) Circular dichroism (CD) spectra of 1 at different concentrations. (e) ThT fluorescence emission at 480 nm ($\lambda_{ex}$ 440 nm) of ThT (20 μM) with increased concentrations of 1 in PBS buffer. See also FIG. 8.

In certain embodiments, the invention relates to a study of the aggregates of a small hydrophobic molecule (1) (to distinguish these aggregates from the aggregates or oligomers of proteins, we term them as "molecular aggregates"). In certain embodiments, the molecular aggregates of 1 (FIG. 6) biophysically and morphologically resemble the aggregates of aberrant protein. In certain embodiments, the molecular aggregates of 1 display extensive, non-covalent intermolecular interactions (i.e., supramolecular interactions), resulting in an exceptional capability of self-assembly to form cross-β fibrillar aggregates in aqueous medium. In certain embodiments, the invention relates to the origin of the cytotoxicity of the molecular aggregates of 1 in cancer cells in the hope to provide insights for understanding the role of protein aggregates in inverse association between cancer and Alzheimer's disease.

While the monomers of 1 are innocuous to all cell lines tested, the molecular aggregates of 1 display differential cytotoxicity towards cancer cell lines and a neuronal cell line. In other words, the aggregates sufficiently inhibit growth of the cancer cells within 48 h but have little acute toxicity on the neuronal cell line. The molecular aggregates enter the cancer cells via active transportation, accumulate in cytoplasm, and disrupt the cell cycle by arresting the cancer cells in G1/G0 phase, in addition to being able to delay cell migration. On the other hand, the neuronal cells uptake less of the molecular aggregates than the cancer cells. Protein pull-down by the hydrogel of the molecular aggregates helps discover the leads of protein targets of the aggregates of 1. Tubulin is one of the targets. In vitro tubulin polymerization and cell-based assays not only confirm tubulin heterodimer as the major protein target, but also indicate that the molecular aggregates of 1 cluster short microtubules and prevent growth of microtubules in cancer cell lines. This observation of self-assembly of small molecules to disrupt self-organization of functional proteins demonstrates an unprecedented mechanism of molecular interaction. Contrary to the case of cancer cells, 1 exhibits little observable disruption of the microtubule network of PC12. This selective cytotoxicity likely stems from not only the increased cellular uptake of cancer cells, but also the existence of neuron-rich microtubule-stabilizing proteins. Moreover, the molecular aggregates inhibit the growth of cancer cells in the xenograft tumor mice model without inducing noticeable inflammation on the mice model. The successful inhibition of xenograft tumor growth promises a new direction for developing anti-cancer drug based on the interaction between molecular aggregates and proteins. Moreover, considering the morphological and phenotypical similarity between the aggregates of 1 and the aggregates or oligomers of aberrant proteins, the molecular basis of the cytotoxicity of the aggregates of 1 implies possibility for the oligomers or aggregates of aberrant protein to exhibit acute cytotoxicity to cancer cells, as well as chronic toxicity to neural cells. The verification of this hypothesis ultimately may provide insights for understanding and treating cancer and Alzheimer disease, the two most devastating human diseases.

Discussion

Cytotoxic oligomers of amyloids, although arising from different proteins and associated with different diseases, share many common properties. The similarities have driven exploration of peptide mimics of β-amyloids in the hope of providing insights regarding Alzheimer's disease and other neurodegenerative diseases. Most of the research, however, has focused on the ability of the peptide fragments (i) to form the cross-β structure, a unique morphological feature of β-amyloid, and (ii) to exhibit neurotoxicity. Although this work recreates one or two key aspects of amyloid proteins, identification of the molecular targets of the aggregates of aberrant proteins has not been possible.

Figure 14:
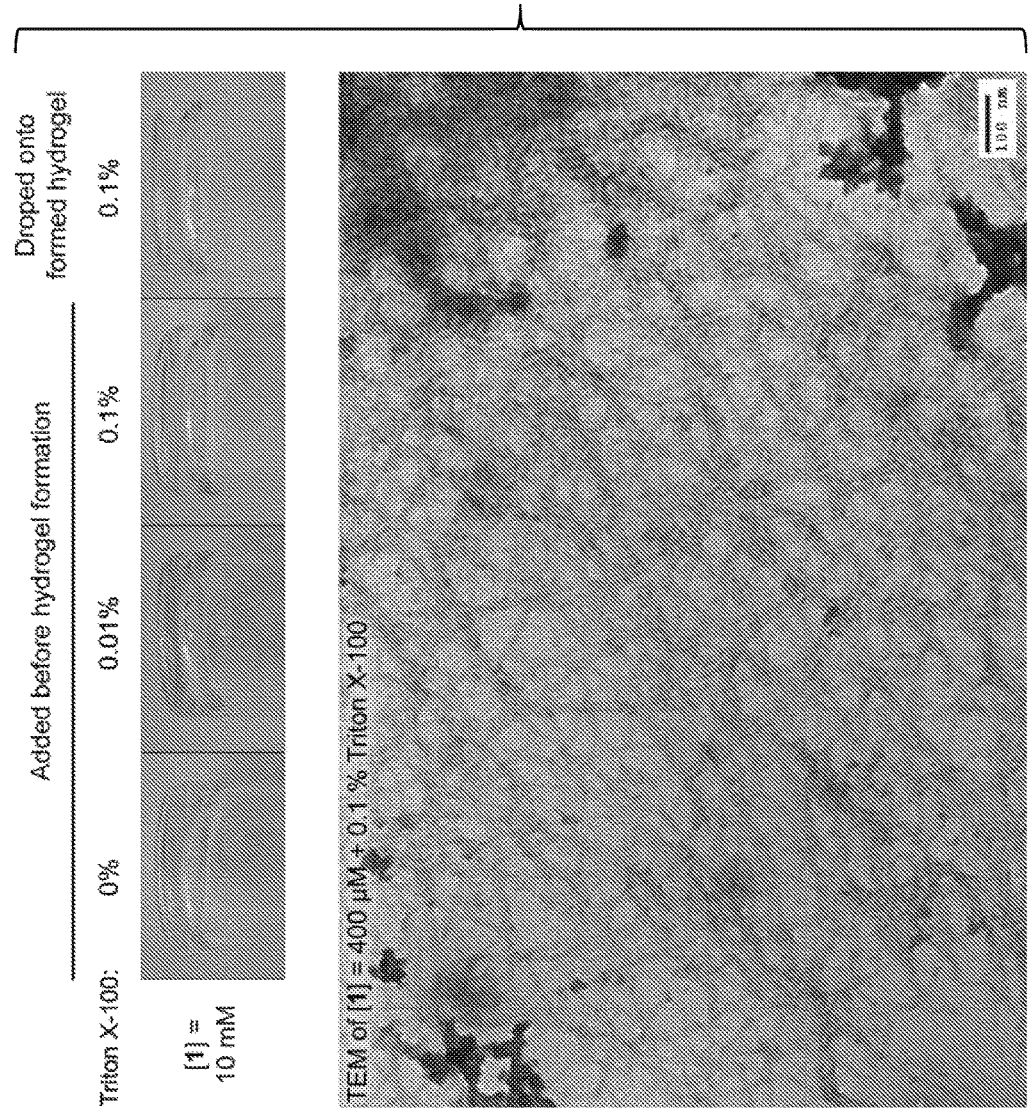
FIG. 14 depicts the influence of a surfactant on self-assembly of 1. Triton X-100 was mixed with 1 (10 mM) before and after hydrogel formation. The hydrogel of 1 can tolerate up to 0.1% Triton X-100. Treated with 0.1% Triton X-100, the fibrillar aggregates of 1 tend to cross-link with each other instead of randomly dispersing, but the width of fibrillar aggregates remains unchanged.

Despite the fact that their building blocks are much smaller ($M_r$ of 1 is 480 Da) than the aberrant proteins (ranging from several thousand to hundred thousand Da), the molecular aggregates of 1 share both morphological and phenotypical features with the aggregates or oligomers of the aberrant proteins. The most notable similarity is that, like the core segments of amyloids, the molecules of 1 self-assemble in water to form fibrillar aggregates that adopt cross-β structure. In addition, like amyloid oligomers, the aggregates of 1 exhibit polymorphism. As observed by CD, different batches of the solutions of 1 at 400 μM give the CD spectra with different intensity and peaks (FIG. 13). Although the characteristic peaks of β-sheets appear in all the CD spectra of the aggregates of 1, indicating the β-sheet like superstructure as the core structure of molecular aggregates of 1, the discordance of the CD measurements resembles the trait of the CD spectra of amyloid peptides, confirming that the aggregates of 1 are kinetically trapped cross-β nanofibers. Moreover, like amyloid oligomers, the aggregates of 1 also resist detergent. That is, the addition of detergent is unable to break up the aggregates of 1 (FIG. 14). These results suggest that the aggregates of 1 and the aggregates of aberrant proteins or the amyloid oligomers share similar thermodynamic and kinetic features.

A less noticed common feature among the aberrant protein aggregates is that they exhibit cytotoxicity at the similar weight/volume concentration. For example, the $IC_{50}$ values of several aberrant protein aggregates (e.g., transthyretin (0.2 mg/mL), HypF-N (0.03~0.2 mg/L), and K11V-TR (0.8 mg/mL)) are mostly in the similar range (several tenths mg/mL) when they exhibit cytotoxicity. The molecular aggregates of 1 exhibit cytotoxicity at the concentrations of 400 µM, which is about 0.19 mg/mL. This coincidence also implies a common, yet unidentified origin for the cytotoxicity of the aggregates of hydrophobic molecules.

Figure 15:
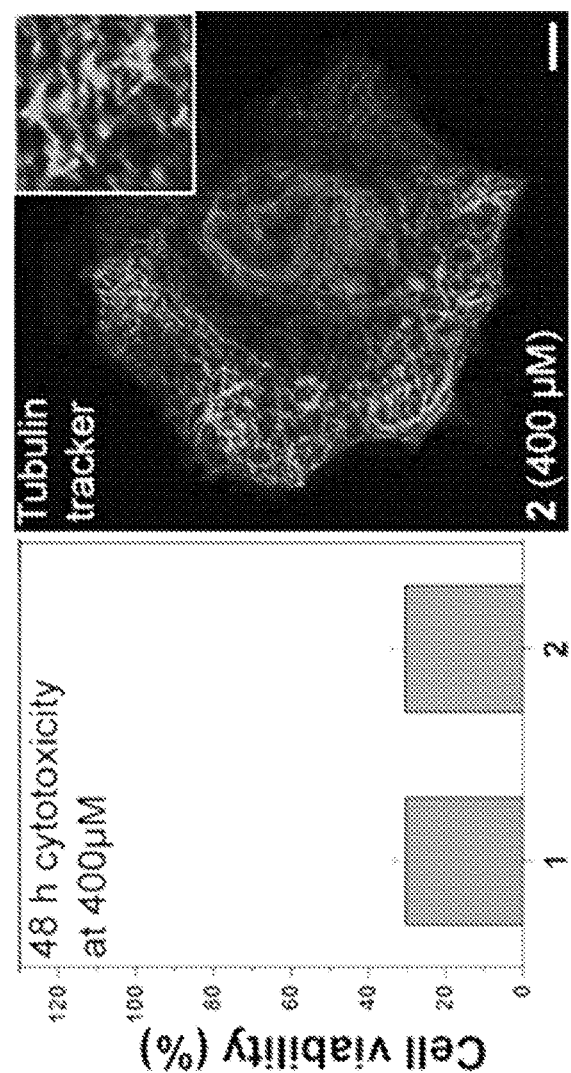
FIG. 15 depicts the structure, cytotoxicity, and cell response of the enantiomer of 1. In molecule 2, L-Phe is replaced by D-Phe. Cytotoxicity of 1 and 2 are examined on HeLa cells at the concentration of 400 μM after 48 h incubation. Data are presented as mean±SD of three independent experiments. Tubulin staining of 2 is performed on HeLa cells at the concentration of 400 μM after 24 h incubation. Scale bar=10 μm.

Another often overlooked feature of amyloid oligomers is that their cytotoxicity is independent of chirality of the amino acids. The enantiomer of 1 (i.e., 2, formed by the replacement of the L-Phe with D-Phe), which has similar ability of aggregation as that of 1, exhibits similar cytotoxicity and ability to disrupt the formation of microtubules (FIG. 15). These results not only exclude the possibility that the dipeptide motif acts as a specific ligand for unknown receptors to result in cell death for the case of 1, but also indicate that the cytotoxicity of molecular aggregates of 1 is independent of chirality of the residue of the peptides. This observation suggests that molecular aggregates of 1 and amyloid oligomers share similar phenotypical features.

Figure 7:
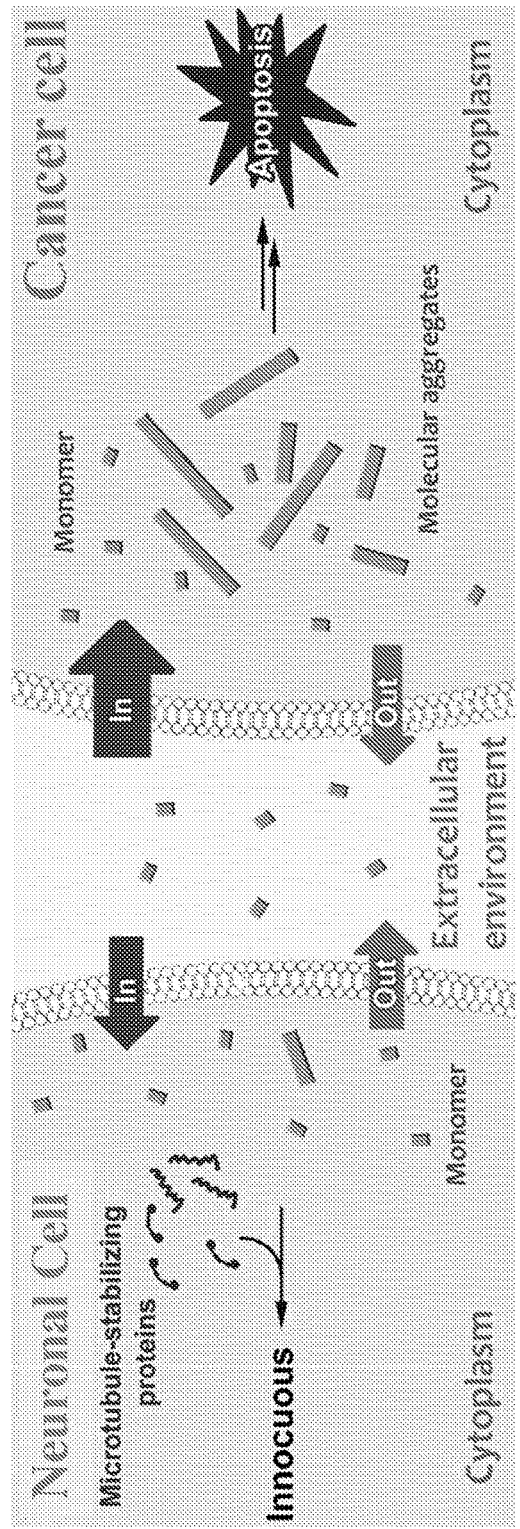
FIG. 7 is an illustration of a plausible molecular mechanism of selective cytotoxicity induced by 1. Due to the Warburg effect, cancer cells uptake an excessive amount of 1 by active transportation. 1 is accumulated in cancer cells, and its aggregates inhibit growth of microtubule, which eventually triggers the apoptosis cascade. In neuronal cells, the uptake and accumulation of 1 is slower than in cancer cells, resulting in less aggregates of 1. The presence of abundant microtubule-stabilizing proteins in the neuronal cells diminishes the inhibition of microtubule growth caused by the aggregates of 1. Thus, 1 induces little acute cytotoxicity on neuronal cells.

The morphological and phenotypical similarities between the molecular aggregates of 1 and amyloid oligomers allow the molecular aggregates of 1 to serve as a mimic of aggregates of aberrant proteins or amyloid oligomers. The molecular aggregates of 1 cluster short microtubules on their surface. The clustered short microtubules likely lack oriented arrangement. Such disorientation disfavors the connection between the short microtubules or sterically hinders the growth of microtubule fibrils. When many of tubulin heterodimers exist in clusters, the cell fails to produce sufficient amount of microtubules. The loss of microtubules mediates cell-cycle arrestment and eventually triggers the apoptosis cascade (FIG. 7). This result also provides a plausible detail for the interaction between tubulin and amyloid-like protein aggregates inside cells. However, multiple bands on SDS-PAGE (FIG. 4) imply that the interaction between molecular aggregates of 1 and cellular proteins, though have a rather specific target, is yet promiscuous. Therefore, it remains a possibility that molecular aggregates of 1 might interact with other proteins in cells to promote clustering of microtubules.

Figure 10A:
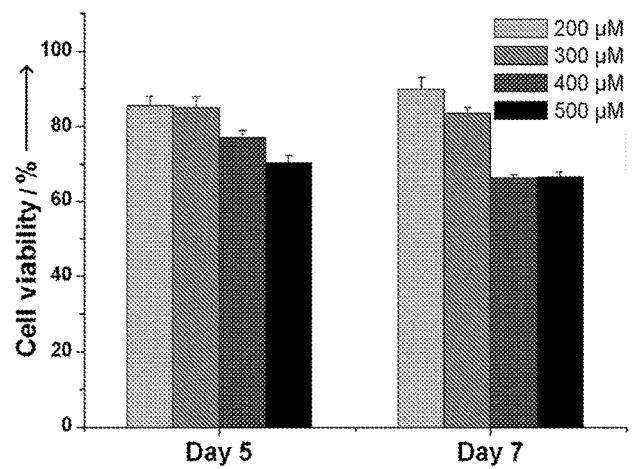
FIG. 10 depicts the long term cytotoxicity of 1 on PC12 cells. Related to FIG. 2. (a) MTT viability test of cell incubated with gradient concentration of 1 for up to 7 days without changing medium. Data are presented as mean±SD of three independent experiments. (b) Intracellular concentration of 1 in PC12 cells treated with 1 for 12 h at 37° C. measured by LC-MS (left bar=400 μM; right bar=300 μM). (c) Cells were subcultured and re-seeded with new medium containing the same concentration of 1 (0 for control group and 400 μM for test group) every 4 days. Data are presented as mean±SD of three independent experiments.
Figure 10B:
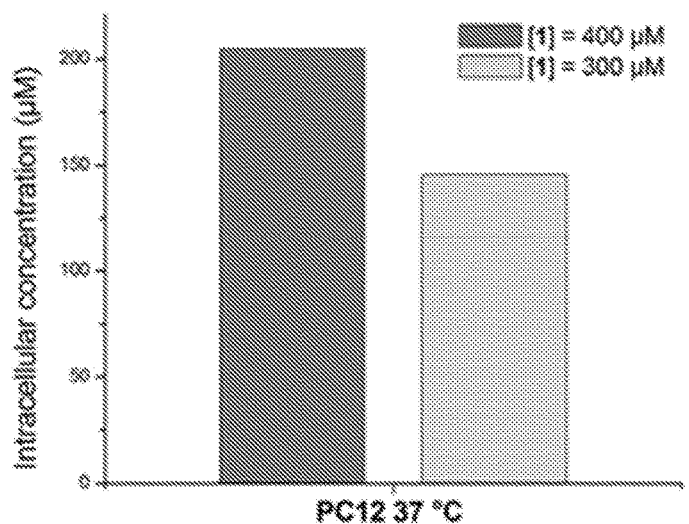
Figure 10C:
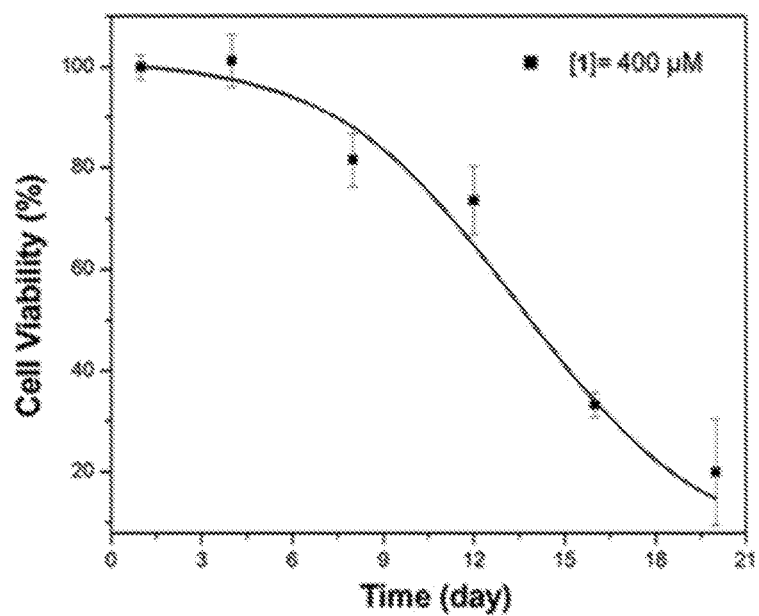

Unlike the case for cancer cells, the aggregates of 1 exhibit little acute cytotoxicity towards neuron cell line (PC12). One reason is that PC12 cells have slower metabolism and growth (e.g., doubling every 72 h) than that of cancer cells. In fact, PC12 cells accumulate much less amount of 1 than HeLa cells do (FIG. 10b). Another reason is that, PC12 cells, as a neuronal cell, have abundant amount of microtubule-stabilizing proteins (e.g., tau and MAP2) to promote tubulin polymerization and stabilize microtubules. Meanwhile, the pull-down assay suggests molecular aggregates of 1 has little or no interaction with tau (FIG. 16), thus hardly disrupting the functions of tau. Therefore, the existence of microtubule-stabilizing proteins in neurons can counter the effect of the molecular aggregates of 1, which is consistent with that PC12 cells, incubated with 1 at 400 µM (FIG. 5p), still display intact microtubule network. These two effects together, protect the PC12 cells from cytotoxicity induced by molecular aggregates of 1 (FIG. 7). However, the constant supply of 400 µM of 1 causes significant loss of cell viability of PC12 cells after 7 days (FIG. 10c), a scenario that is similar to the chronic toxicity of amyloid oligomers in Alzheimer's disease.

Figure 17:
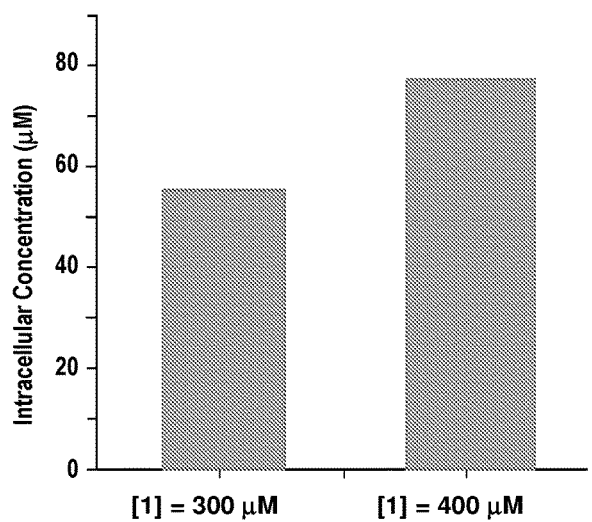
FIG. 17 depicts the degradation of 1 in HeLa cells. HeLa cells were lysed after incubation with 1 at different concentrations for 12 h at 37° C. The fragmental residue of 1 detected and quantified by LC-MS was (S)-2-(2-(naphthalen-2-yl) acetamido)-3-phenylpropanoic acid.
Figure 18:
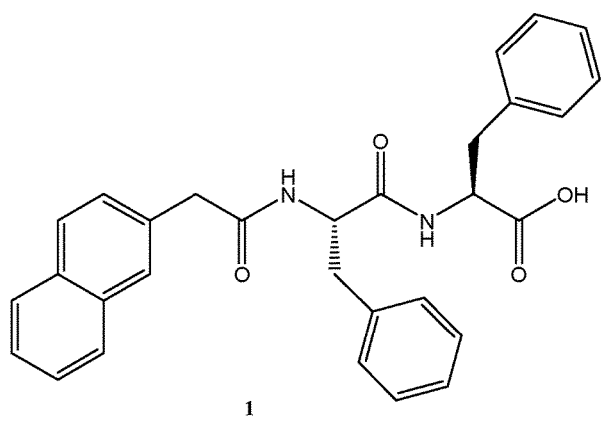
FIG. 18 depicts the structure of compound 1.
Figure 19:
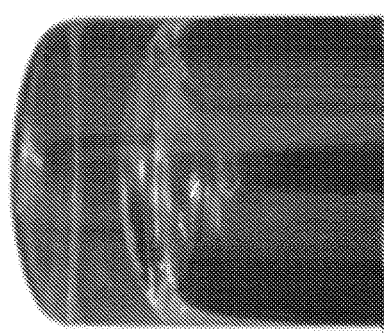
FIG. 19 depicts an optical image of the hydrogel formed by 0.4 wt % of 1 in PBS buffer.

The self-assembly of small molecules to disrupt self-organization of protein is a new mechanism of molecular interaction. While self-organization of tubulin heterodimers in cell is already a very complex process, characterization of the atomic-level structures of molecular aggregates of 1 is of great difficulty because of their polymorphism. Due to these two reasons, elucidating the atomistic detail of the interactions between the molecular aggregates of 1 and tubulin heterodimers remains to be a challenge. Nonetheless, selective inhibition of tumor cells over neuronal cells in cell assays and successful inhibition of tumor progression in the xenograft animal model underscore the potential of molecular aggregates of 1, or aggregates formed by other small molecules, as a new paradigm for cancer therapy without depending on tight ligand-receptor binding. Notably, the abated cytotoxicity of 1 towards neuronal cell promises the application of 1 in targeting brain tumors while leaving the central nerve system unharmed. Moreover, a merit of these self-assembled aggregates is that their cytotoxicity is governed by the spatiotemporal profiles of the aggregates. Unlike amyloid proteins that resist degradation and induce chronic cytotoxicity, the degradation of 1 (FIG. 17) and other small molecular aggregates are rather fast and even tunable. The spatiotemporal profiles of the molecular aggregates not only promise little chronic effect but also offer controllable cytotoxicity via tuning of aggregation.

Although it remains unable to provide a simple notion for explaining the lowered Alzheimer's disease rate in cancer patients, this study on the aggregates of 1 offers valuable insights for understanding the lowered cancer rate in Alzheimer's disease patients. The molecular aggregates of 1 induce differential and selective cytotoxicity in both cell and animal models. These results imply that amyloid oligomers, as they are similar with molecular aggregates of 1 in many aspects, might also inhibit the growth of cancer cells to result in the inverse cancer comorbidity in patients with Alzheimer's disease. Although other possible molecular mechanisms remain to be elucidated, this study offers a new perspective and a new direction for understanding the complicated inverse association between Alzheimer's disease and cancers.

Definitions

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

In order for the present invention to be more readily understood, certain terms and phrases are defined below and throughout the specification.

The articles "a" and "an" are used herein to refer to one or to more than one (i.e., to at least one) of the grammatical object of the article. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of", or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Certain compounds contained in compositions of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

For purposes of this invention, the chemical elements are identified in accordance with the Periodic Table of the Elements, CAS version, Handbook of Chemistry and Physics, 67th Ed., 1986-87, inside cover.

Exemplary Methods of the Invention

In certain embodiments, the invention relates to a method of treating or preventing cancer comprising the step of
administering to a subject in need thereof a plurality of hydrophobic, self-assembling monomers.

In certain embodiments, the invention relates to any one of the aforementioned methods, wherein the cancer is a sarcoma, a carcinoma, or a lymphoma.

In certain embodiments, the invention relates to any one of the aforementioned methods, wherein the cancer is a brain tumor.

In certain embodiments, the invention relates to a method of retarding or preventing the growth of a microtubule comprising the step of contacting tubulin with a plurality of hydrophobic, self-assembling monomers.

In certain embodiments, the invention relates to any one of the aforementioned methods, wherein the tubulin is in the form of a heterodimer. In certain embodiments, the invention relates to any one of the aforementioned methods, wherein the tubulin is in the form of an α- and β-tubulin heterodimer.

In certain embodiments, the invention relates to any one of the aforementioned methods, wherein the hydrophobic, self-assembling monomer is represented by Formula I:

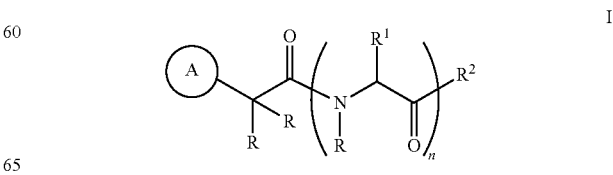

I wherein, independently for each occurrence, (A)

is aryl, heteroaryl, aralkyl, or heteroaralkyl;

R is H or alkyl;

$R^1$ is aralkyl or heteroaralkyl;

$R^2$ is H, alkyl, —OR, or —$NR_2$;

n is 1, 2, 3, 4, 5, 6, 7, 8, 9, 10, 11, 12, 13, 14, 15, 16, 17, 18, 19, or 20.

In certain embodiments, the invention relates to any one of the aforementioned methods, wherein (A)

is aryl. In certain embodiments, the invention relates to any one of the aforementioned methods, wherein (A)

is naphthyl. In certain embodiments, the invention relates to any one of the aforementioned methods, wherein (A)

is 2-naphthyl.

In certain embodiments, the invention relates to any one of the aforementioned methods, wherein R is H.

In certain embodiments, the invention relates to any one of the aforementioned methods, wherein $R^1$ is aralkyl. In certain embodiments, the invention relates to any one of the aforementioned methods, wherein $R^1$ is substituted aralkyl. In certain embodiments, the invention relates to any one of the aforementioned methods, wherein $R^1$ is hydroxyaralkyl. In certain embodiments, the invention relates to any one of the aforementioned methods, wherein $R^1$ is 4-hydroxyaralkyl. In certain embodiments, the invention relates to any one of the aforementioned methods, wherein $R^1$ is benzyl. In certain embodiments, the invention relates to any one of the aforementioned methods, wherein $R^1$ is substituted benzyl. In certain embodiments, the invention relates to any one of the aforementioned methods, wherein $R^1$ is hydroxybenzyl. In certain embodiments, the invention relates to any one of the aforementioned methods, wherein $R^1$ is 4-hydroxybenzyl.

In certain embodiments, the invention relates to any one of the aforementioned methods, wherein $R^2$ is —OR or —$NR_2$. In certain embodiments, the invention relates to any one of the aforementioned methods, wherein $R^2$ is —OR. In certain embodiments, the invention relates to any one of the aforementioned methods, wherein $R^2$ is —OH.

In certain embodiments, the invention relates to any one of the aforementioned methods, wherein n is 1, 2, 3, 4, or 5. In certain embodiments, the invention relates to any one of the aforementioned methods, wherein n is 1, 2, or 3. In certain embodiments, the invention relates to any one of the aforementioned methods, wherein n is 2.

In certain embodiments, the invention relates to any one of the aforementioned methods, wherein the hydrophobic, self-assembling monomer is represented by:

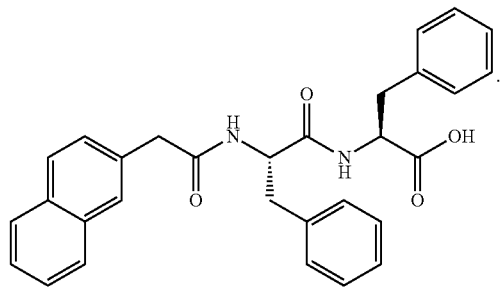 [SMILES: O=C(Cc1ccc2ccccc2c1)N[C@@H](Cc1ccccc1)C(=O)N[C@@H](Cc1ccccc1)C(=O)O]

In certain embodiments, the invention relates to any one of the aforementioned methods, wherein the hydrophobic, self-assembling monomer is represented by:

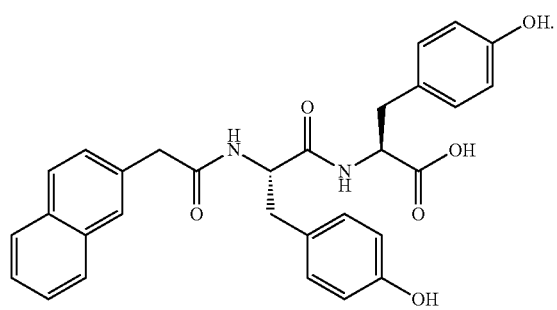 [SMILES: O=C(Cc1ccc2ccccc2c1)N[C@@H](Cc1ccc(O)cc1)C(=O)N[C@@H](Cc1ccc(O)cc1)C(=O)O]

In certain embodiments, the invention relates to any one of the aforementioned methods, wherein the hydrophobic, self-assembling monomer is described in U.S. Patent Application Publication No. US 2012/0142616, PCT Patent Application Publication No. WO 2012/166705, or PCT Patent Application Publication No. WO 2012/166706, the entire contents of each of which are hereby incorporated by reference.

In certain embodiments, the invention relates to any one of the aforementioned methods, wherein the hydrophobic, self-assembling monomer comprises a dipeptide. In certain embodiments, the dipeptide comprises L-amino acids or D-amino acids.

In certain embodiments, the invention relates to any one of the aforementioned methods, wherein the hydrophobic, self-assembling monomer is present at a concentration greater than about 200 µM. In certain embodiments, the invention relates to any one of the aforementioned methods, wherein the hydrophobic, self-assembling monomer is present at a concentration greater than about 300 µM. In certain embodiments, the invention relates to any one of the aforementioned methods, wherein the hydrophobic, self-assembling monomer is present at a concentration of about 300 µM, about 320 µM, about 340 µM, about 360 µM, about 380 µM, about 400 µM, about 420 µM, about 440 µM, about 460 µM, about 480 µM, about 500 µM, about 520 µM, about 540 µM, about 560 µM, about 580 µM, or about 600 µM.

EXEMPLIFICATION

The invention now being generally described, it will be more readily understood by reference to the following examples, which are included merely for purposes of illustration of certain aspects and embodiments of the present invention, and are not intended to limit the invention.

Example 1—General Materials and Methods

Xenograft Mouse Model:

Nu/nu mice were injected with HeLa cells ($5\times10^6$) subcutaneously for tumor development. Treatment was started when average tumor size reached 30 mm$^3$. Mice were divided into three groups. One group (n=3) received 0.1 mL PBS buffer as control, the other two groups (n=4) received 0.1 mL of 1 at 5 mM or 0.5 mM. Six doses were given every three days starting day 1. Progression of tumor was monitored until 19$^{th}$ day of the treatment.

Hydrogel Based Protein Pull-Down Assay:

$4\times10^7$ of HeLa cells were scrapped from petri dish and washed with PBS buffer for 3 times then centrifuged at 300 g for 5 minutes. The collected cell pellet was mixed with phosphate buffer (100 mM) then snap freeze and thaw for 3 cycles to lyse the cells. The cell lysate was clarified by centrifugation at 12,000 g for 20 min at 4° C. to remove the whole cells, nuclei and large mitochondria. 50 µL of the supernatant lysate was gently mixed with 30 µL hydrogel of 1 (10 mM in PBS buffer, pH 7.6) on rotator at RT for 30 min. The hydrogel was collected by centrifugation (12,000 g, 5 min, 4° C.) and the supernatant was collected and placed on ice before analysis. The hydrogel was washed three times by gently mixing with 50 µL of the washing buffer (50 mM phosphate buffer pH 7.6 supplemented with 150 mM NaCl) on rotator at RT for 10 min followed by separation on centrifuge (12,000 g, 5 min, 4° C.). Supernatants were collected and placed on ice before analysis. Finally, the remaining hydrogel was dissolved using 1:1 washing buffer and 5× Laemeli buffer. All other samples were mixed with 5× Laemeli buffer (final concentration 2×) before SDS-PAGE.

Materials and Methods:

All cell lines were obtained from ATCC. All antibodies were obtained from Abcam. Tubulin polymerization assay, tubulin and biotinylated tubulin were obtained from Cytoskeleton. Tubulin tracker and all culture media were obtained from Invitrogen. Anti-tubulin gold nanoparticles were obtained from Antibodies-Online. All other chemicals and reagents were obtained from FisherSci. Circular dichroism was performed on a JASCO J-810 spectrometer, transmission electron microscopy on Morgagni 268 transmission electron microscope, MTT viability assay and tubulin polymerization assay on DTX 880 multimode detector, flow cytometry on FACSCalibur flow cytometer, isothermal titration calorimetry on TA instrument NANO ITC Low volume, fluorescence spectra on RF-5301PC spectrofluorophotometer, confocal images on Leica SP2 microscope.

Isothermal Titration Calorimetry (ITC):

50 µL 1 in PBS buffer (pH 7.6) at 200, 300, 400 or 500 µM was diluted into 170 µL PBS buffer (pH 7.6) at a rate of 2 µL per injection and 300 s interval between each injection. The $\Delta H_{dil}$ was calculated as an average value of heat release from 20 injections.

Cell Viability Assay (MTT):

Cells in exponential growth phase were seeded in a 96 well plate at a concentration of 50,000 cell/well. The cells were allowed to attach to the wells for 24 h at 37° C., 5% $CO_2$, then the culture medium was removed and 100 µL new culture medium containing 1 at gradient concentrations was placed into each well. After culturing at 37° C., 5% CO2 for desired time, each well was added by 10 µL of 5 mg/mL MTT 43-(4,5-Dimethylthiazol-2-yl)-2,5-diphenyltetrazolium bromide), and the plated cells were incubate at dark for 4 h. 100 µL 10% SDS with 0.01 M HCl was added to each well to stop the reduction reaction and to dissolve the purple. After incubation of the cells at 37° C. for overnight, the viability is measured. Data represent the mean±standard deviation of three independent experiments.

Negative Staining of TEM:

Carbon coated grids were glow discharged just before using to increase their hydrophilicity. The sample solution (3 µL) was place on the grid to cover the grid surface. After rinsing the grids for 10 s, a large drop of the ddH$_2$O was placed on parafilm and let the grid touch the water drop, with the sample-loaded surface facing the parafilm. The grid was titled, and water was gently absorbed from the edge of the grid by using a filter paper for 3 times. The grid was stained immediately by letting the grid touch a drop of 2.0% (w/v) uranyl acetate on the parafilm with the sample-loaded surface. The grid was titled, and the stain solution was gently absorbed from the edge of the grid by using a filter paper for 3 times. The grid was allowed to dry in air for a few minutes and was examined immediately.

TEM of Cell Lysate:

After being incubated with 500 µM of 1 for 24 h, the HeLa cells were washed with PBS buffer three times and lysed in water for 30 min. The lysate was collected and the unbroken cells were removed by centrifuge at 300 g for 5 min. $CaCl_2$ was added to the supernatant to a final concentration of 2 mM and incubate at room temperature for 30 min to disrupt microtubule that has similar diameter to molecular aggregates of 1 and thus obscure the observation. 1 µL of 1 mg/mL rabbit anti-β-tubulin@Au (in 0.01 M PBS, pH 7.4 with 10 mg/mL BSA and 0.1% sodium azide) was added to 20 µL of cell lysate, and then the solution was mixed by up and down pipetting. Negative stained TEM sample was prepared as described below.

Tubulin Staining:

Cells in exponential growth phase were seeded in glass bottomed culture chamber at 10,000 cell/mL. The cells were allowed for attachment for 24 h at 37° C., 5% $CO_2$. The culture medium was removed, and new culture medium containing 1 at 0 or 400 µM was added. After 24 h of incubation, cells were washed with PBS buffer for 3 times and stained by Tubulin Tracker™ Green at 100 nM and DAPI 300 nM in PBS for 30 min at 37° C. in dark. The sample was rinsed three times in PBS, and the cells were kept in PBS for imaging.

Example 2—Characterization of the Molecular Aggregates

Figure 1B:
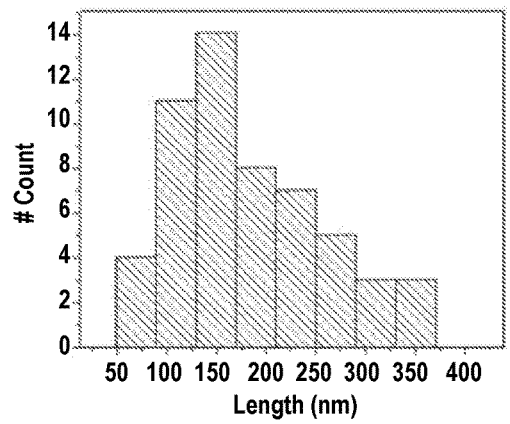
Figure 1C:
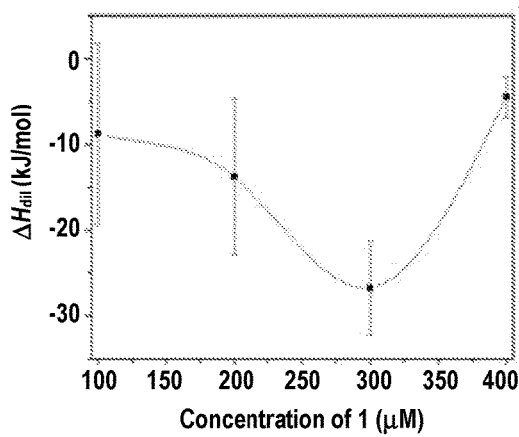
Figure 8:
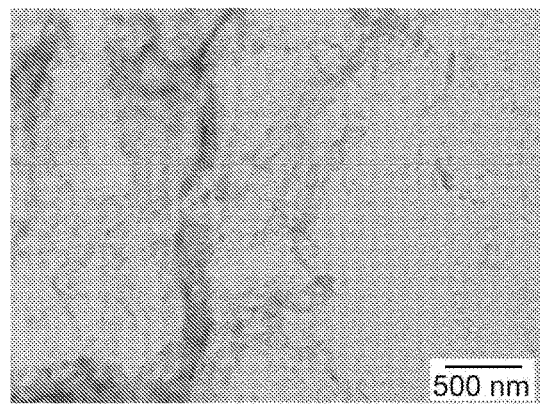
FIG. 8 depicts a TEM image of 1 at 300 μM. Related to FIG. 1. Negative-stained TEM image of 1 at 300 μM in PBS buffer.

After dissolving 1 in PBS buffer (pH 7.6) in a series of dilutions, we used transmission electron microscopy (TEM) (Frado and Craig, 1992) to examine the solutions. The negatively-stained TEM image of the solution of 1 at 400 µM (FIG. 1a) shows fibrillar structure that have uniform width at 24±2 nm and a relatively wide distribution of the lengths with the average value of about 181 nm (FIG. 1b). However, the solution of 1 at 300 µM hardly shows any fibrillar structure in the TEM image (FIG. 8). Isothermal titration calorimetry (ITC) data agree with the results from TEM. The enthalpy of dilution of 1 ($\Delta H_{dil}$) is a negative value as the process of dilution is exothermic. The magnitude of $\Delta H_{dil}$ of 1 becomes larger with the increase of the concentrations of 1 up to 300 µM; this trend follows the modified McMillan-Mayer model, which states that $\Delta H_{dil}$ is a monotonic function of the effective concentration of the solute (Palecz, 1998). At the concentration of 400 µM, $\Delta H_{dil}$ of 1 drastically departs from the trend and is the smallest value measured (FIG. 1c), indicating few monomers of 1 in the 400 µM solution of 1. This exception agrees with that 1 exists mostly as aggregates at this concentration (i.e., 400 µM).

Figure 1D:
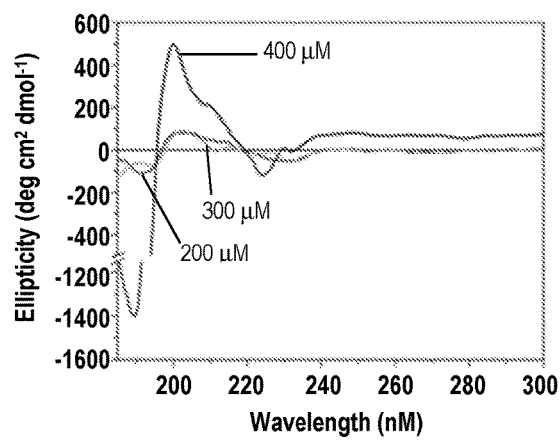
Figure 1E:
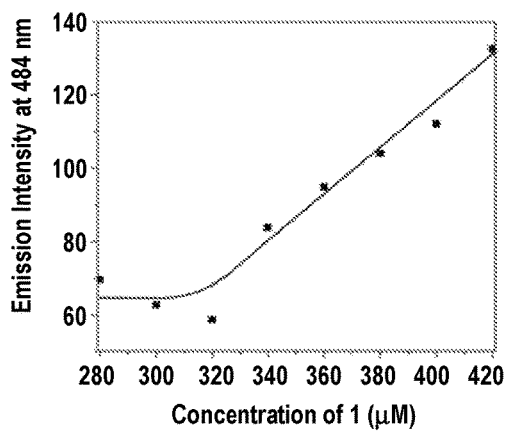

Circular dichroism (CD) spectrum of 1 at 400 µM shows a negative peak at 190 nm followed by a positive peak at 200 nm (FIG. 1d), correlating to cross-β structure according to CD simulation (Greenfield, 2006). This result coincides with the self-assembly molecular model derived from the crystal structure of 1 and, again, confirms existence of the aggregates of 1 at this concentration. At 200 µM and 300 µM, the solutions of 1 give CD signals too weak (FIG. 1d) to be analyzed by the CD simulation, indicating much less amount of aggregates of 1. The CD data not only support the conclusion from TEM and ITC, but also justify the use of thioflavin T (ThT), a benzothiazole dye exhibiting enhanced fluorescence upon binding to β-sheet containing fibrils, to quantify the aggregates of 1. As shown FIG. 1e, the ThT emission changes little at and below 320 µM and starts to increase in a near linear manner with the concentrations of 1 at and above 340 µM, indicating that the threshold concentration for the formation of molecular aggregates of 1 is between 320-340 µM.

Figure 6:
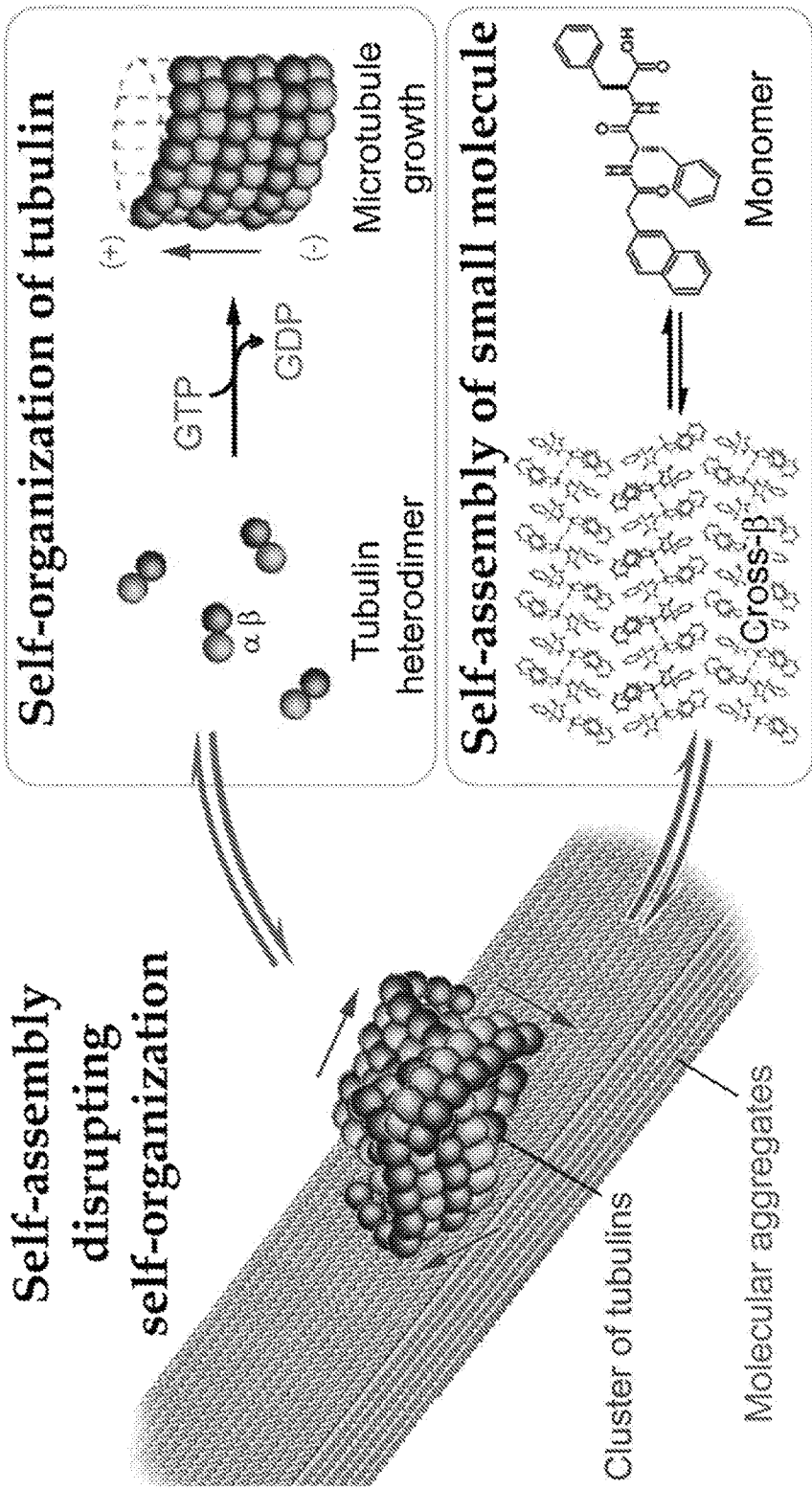
FIG. 6 is an illustration of the interaction between molecular aggregates of 1 and tubulin heterodimers inside cells. Molecules of 1 self-assemble to form cross-β structure that results in fibrillar molecular aggregates (structural simulation showing in gray) in aqueous medium. The molecular aggregates of 1 cluster and disorient short microtubules on the surface, and consequently prevent the formation of oriented long microtubule fibrils. Red arrows point out the orientation of each microtubule.

Collectively, the above results confirm that a significant amount of 1 exists as the fibrillar molecular aggregates in aqueous phase when the concentration of 1 is higher than 320 µM, and the crystal structure of 1 suggests that multiple, intermolecular aromatic-aromatic interactions and intermolecular hydrogen bonding cooperatively promote 1 to self-assembly into β strand-like structures (FIG. 6).

Example 3—Differential Cytotoxicity of the Molecular Aggregates

Figure 2A:
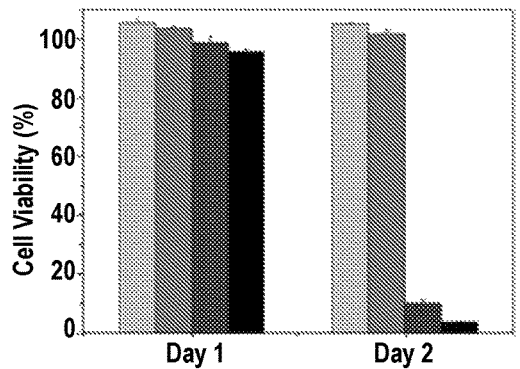
FIG. 2 depicts the cytotoxicity of 1. Cell viability assay (MTT) of HeLa cells after 24 and 48 h of treatment with (a) as prepared or (b) filtered medium containing different concentrations of 1. Also shown are MTT assays of 1 towards (c) MCF 7, (d) HepG2, (e) T98G and (f) PC12 cell lines. Data are presented as mean±SD of three independent experiments. (g) Tumor progression curves of mice bearing HeLa tumors. 0.1 mL of 1 at 5 mM or 0.5 mM in PBS buffers or just PBS buffer as control (six doses, starting day 1) was subcutaneous peritumorally injected every three days. Data are presented as mean±SD of relative tumor volume (n=4 for treatment groups and n=3 for control group). *p<0.05, by Student's t test. (at day 19, 5 mM=bottom data point; 0.5 mM=middle data point; control=top data point). (h) A representative image to show the mice, started with similar initial tumor volume ($V_0$), from each group on $19^{th}$ day of treatment. White arrows point at tumor. See also FIG. 9, FIG. 10, and FIG. 11.
Figure 2B:
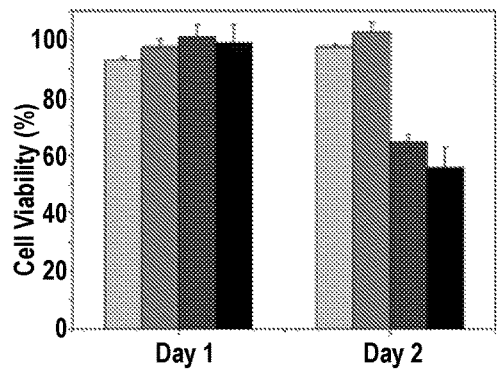
Figure 2C:
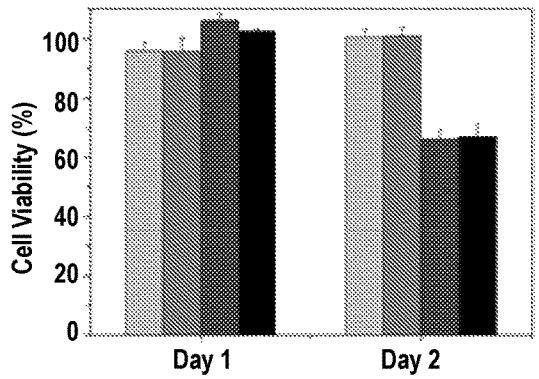
Figure 2D:
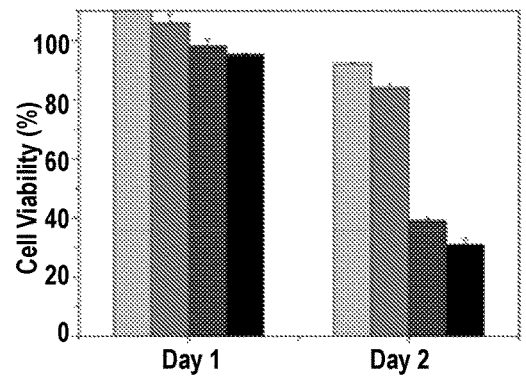
Figure 2E:
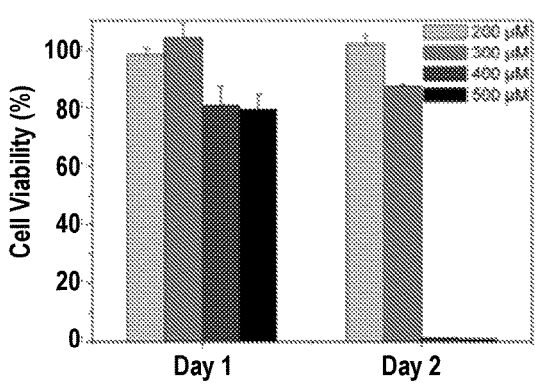
Figure 2F:
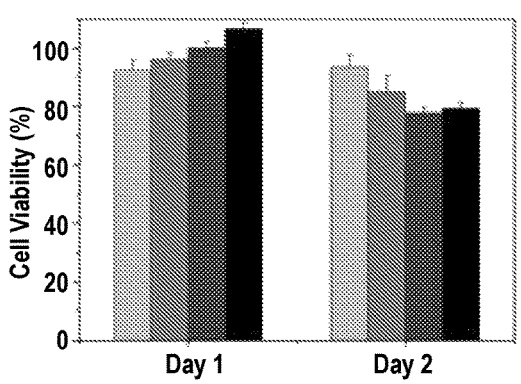
Figure 9A:
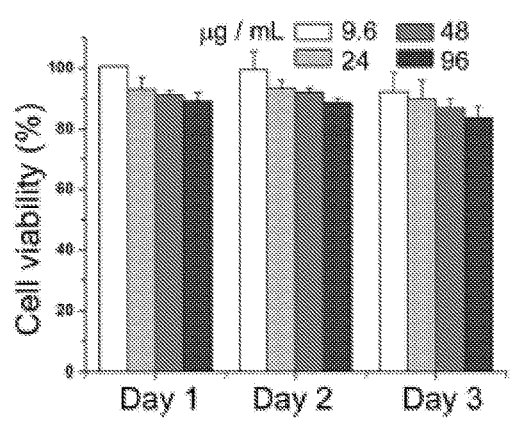
FIG. 9 depicts the cytotoxicity of 1. Related to FIG. 2. (a) 72-h viability test of 1 on HeLa cells below threshold concentrations. Cytotoxicity of 1 towards other cancer cell lines (b) U87MG, (c) Capan-2 and (d) MES-SA. Data are presented as mean±SD of three independent experiments.
Figure 9B:
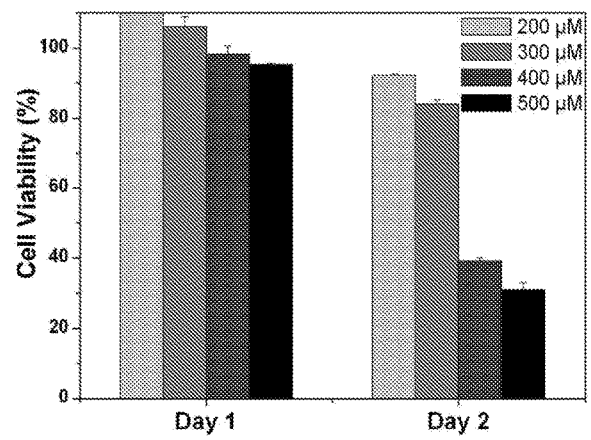
Figure 9C:
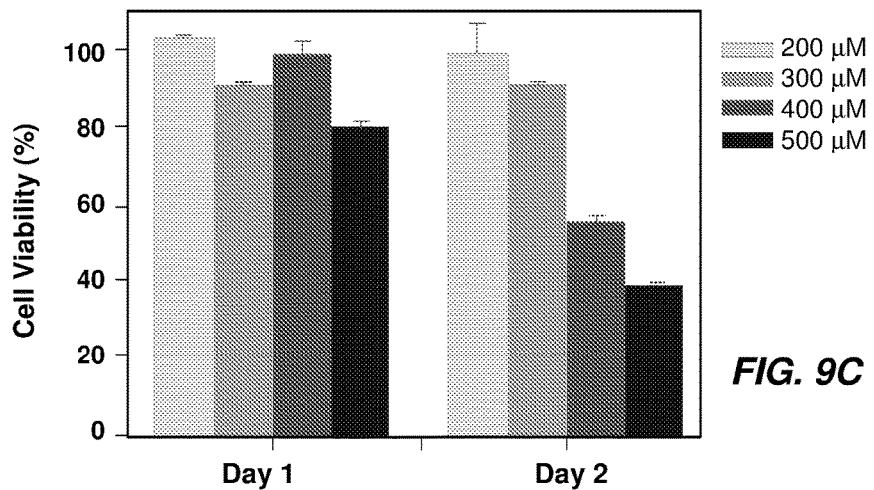
Figure 9D:
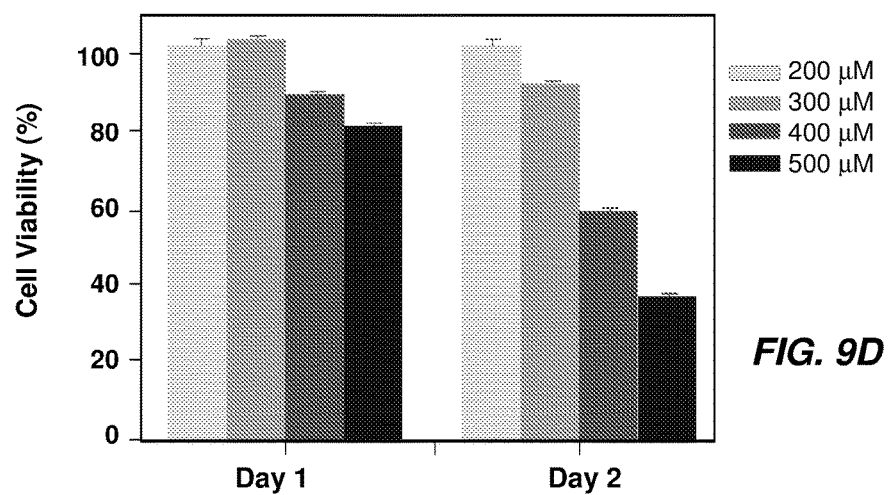
Figures 20A, 20B:
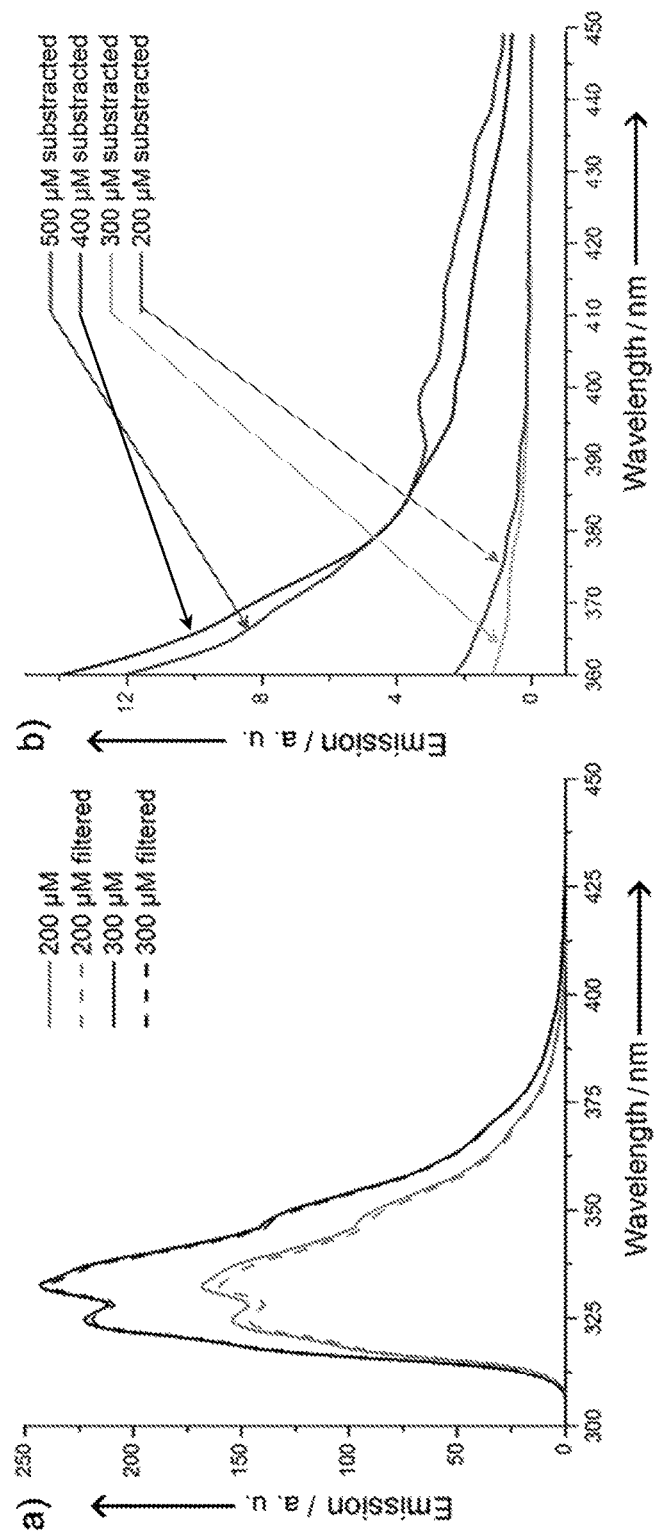
FIG. 20 depicts fluorescence spectra of 1 in PBS buffer with increased concentration of 1 ($\lambda_{ex}$=275 nm). a) Fluorescence spectra of 1 at 200 and 300 μM in PBS buffer with and without filtration. b) The excimer band of naphthalene group was obtained by subtraction of the fluorescence spectra of filtrated 1 from the spectra of as prepared 1 solution ($\lambda_{ex}$=275 nm). Filtration of 1 induces little change in the emission intensity of 1 at 200 and 300 μM and there is little intensity for excimer of naphthalene at 200 and 300 μM.
Figure 21:
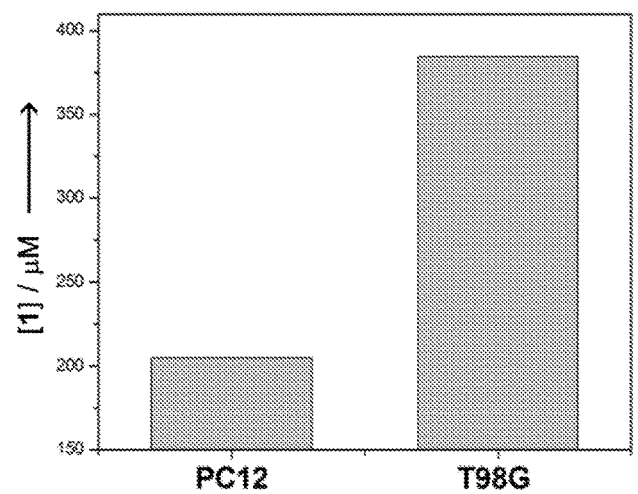
FIG. 21 depicts the intracellular concentration of 1 in PC12 and T98G cells after incubation with 400 μM of 1 for 12 h. Cells in exponential growth phase were seeded in a 10 cm petri dish at 10,000 cell/mL. The cells were allowed to attach for 24 h at 37° C., 5% $CO_2$. The culture medium was removed, and new culture medium containing 1 at 0 or 400 μM was added. After 12 h of incubation, cells were washed with PBS buffer 3 times and collected by cell scraper with 1 mL of PBS buffer. The cell suspension was centrifuged at 600 g for 5 min to obtain a cell pellet. 10 μL of the cell pellet were lysed in 200 μL of water and 200 μL of MeOH. After centrifugation at 12,000 g for 5 min to remove insoluble proteins, the lysate suspension was collected. The concentration of 1 in the lysate was measured by LC-MS.
Figure 22A:
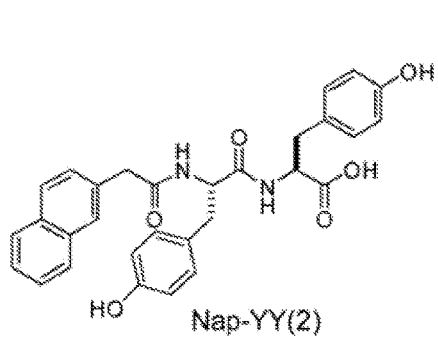
FIG. 22 depicts the characteristics and cytotoxicity of a structural analog of 1. Replacement of phenylalanine in 1 with tyrosine gives rise to Nap-YY (2) that has poorer gelation ability and lower cytotoxicity than 1. a) Chemical structure of 2. b) Circular dichroism spectra of 2 at different concentrations in PBS buffer. c) TEM image of 2 at 5 mM shows the self-assembled structures of 2. d) MTT assay of HeLa cells incubated with 2.
Figure 22B:
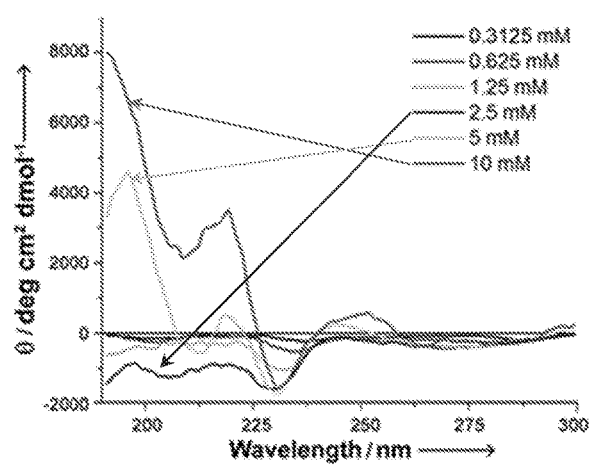

The estimation of the threshold concentration of aggregation (320-340 µM) for 1 allows us to examine the cytotoxicity of 1 in monomer and molecular aggregate forms. We first tested the cytotoxicity of 1 towards HeLa cells, the most widely studied cancer cell line, below and above the threshold concentration. While exhibiting little cytotoxicity at concentrations (200 and 300 µM) below the threshold concentration, 1, at 400 and 500 µM, significantly decreases the viability of the HeLa cells to less than 20% within 48 h (FIG. 2a). The cytotoxicity of 1 towards HeLa cells significantly deviates from the sigmoidal dose response law, suggesting that the cytotoxicity of 1 at and above 400 µM unlikely stems from monomeric 1 or ligand-receptor binding that involves monomeric 1. In addition, the removal of the molecular aggregates of 1, by passing the medium containing 1 through a 0.22 µm PVDF filter, largely alleviates the cytotoxicity of 1 at the concentrations of 400 and 500 µM (FIG. 2b). These results indicate that the cytotoxicity of 1 above the threshold concentration originates from the aggregates of 1. The extension of cell assay at 200 or 300 µM of 1 to 72 h hardly results in significant cell death (FIG. 9a), suggesting the monomeric 1 is cell compatible. Moreover, being incubated with other cancer cell lines (MCF-7, HepG2, T98G, U87MG, Capan-2, and MES-SA), 1 exhibits cytotoxicity in a similar manner to its effect on HeLa cell, with decreases of cell viabilities only observed at 400 and 500 µM (see FIG. 2c, d, and e; and FIG. 9b, c, and d). These results imply that the cytotoxicity of molecular aggregates of 1 and cell compatibility of monomeric 1 towards cancer cell lines is a general phenomenon. While being acutely cytotoxic to all cancer cell lines tested, 1, at 400 and 500 µM, exhibit little toxicity towards PC12, a neuronal cell line (FIG. 20. After being incubation with 1 at 400 and 500 µM for 7 days, PC12 cells remain largely viable (over 60%), suggesting that the molecular aggregates of 1 lack acute toxicity to PC12 (FIG. 10a).

Figure 2G:
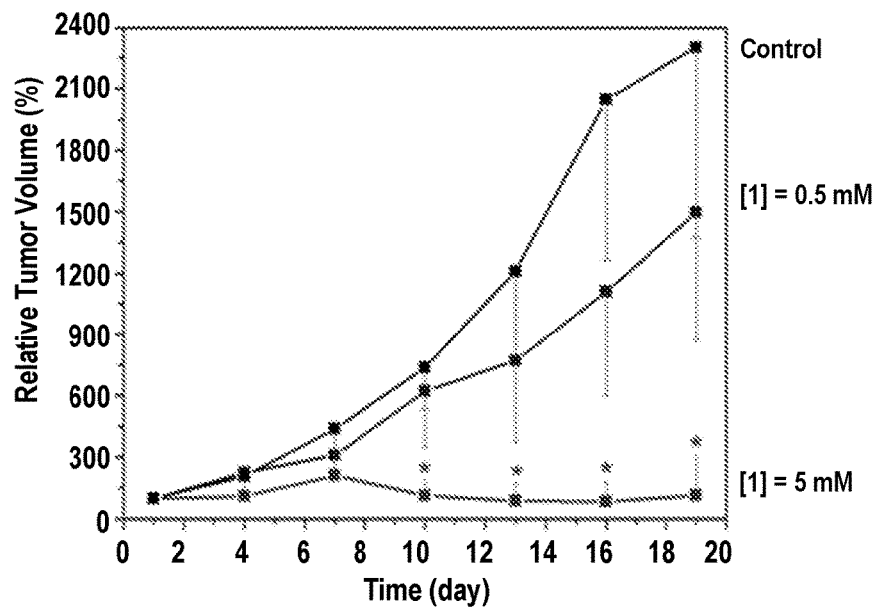
Figure 2H:
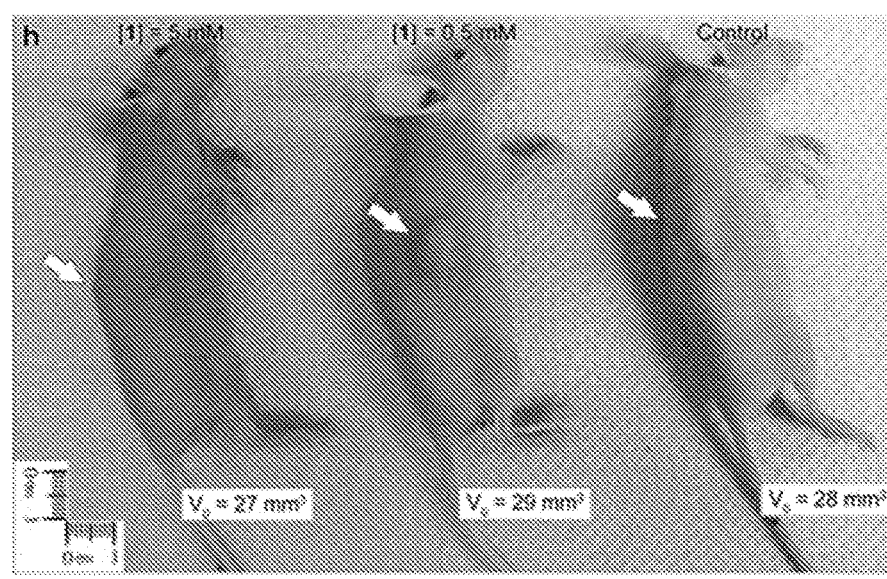
Figure 11A:
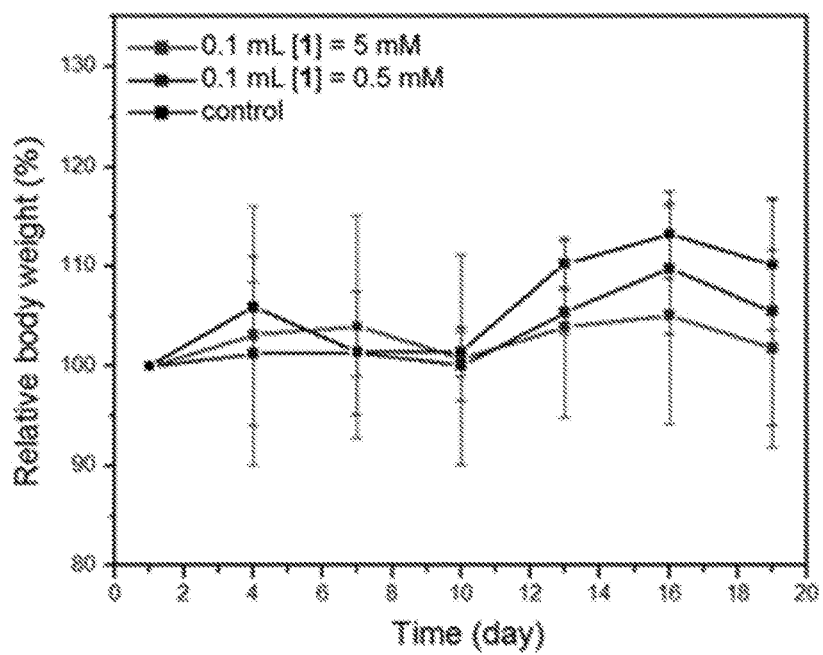
FIG. 11 depicts the effect of 1 on tumor progression in mice models bearing HeLa tumors. Related to FIG. 2. (a) Body weight change curves of mice bearing HeLa tumors. Mice treated with 0.1 mL of 5 mM or 0.5 mM of 1 have no significant weight loss or weight gain comparing with mice in the control group. Data are presented as mean±SD (n=4 for treatment groups and n=3 for control group) of relative tumor volume (at day 19, 5 mM=bottom data point; 0.5 mM=middle data point; control=top data point). Images showing mice bearing tumors from control group (b), 0.5 mM of 1 treatment group (c) and 5 mM of 1 treatment group (d) on 19th day of treatment. White arrows point at tumor.
Figure 11B:
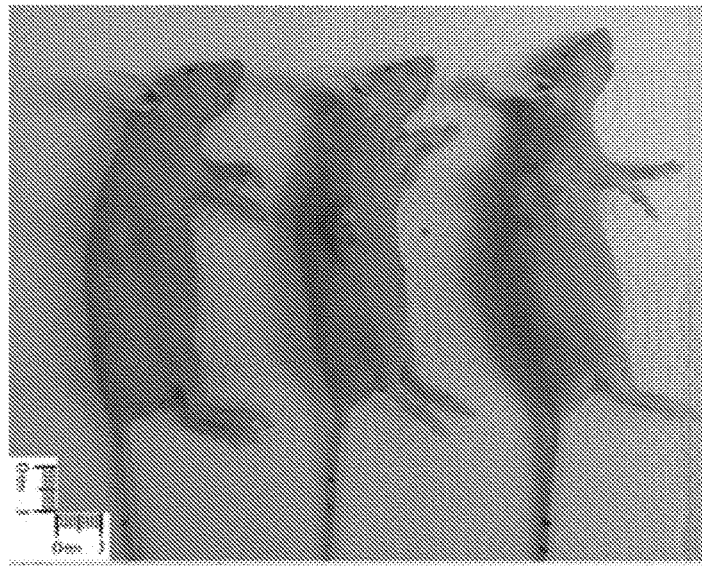
Figure 11C:
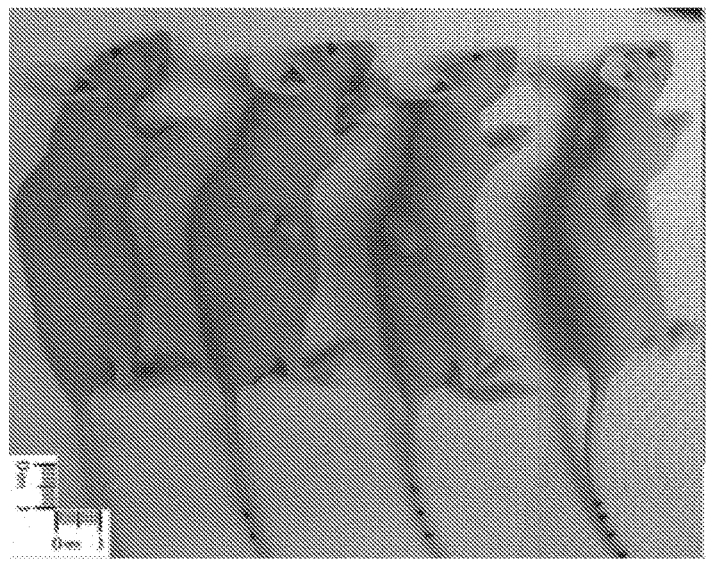
Figure 11D:
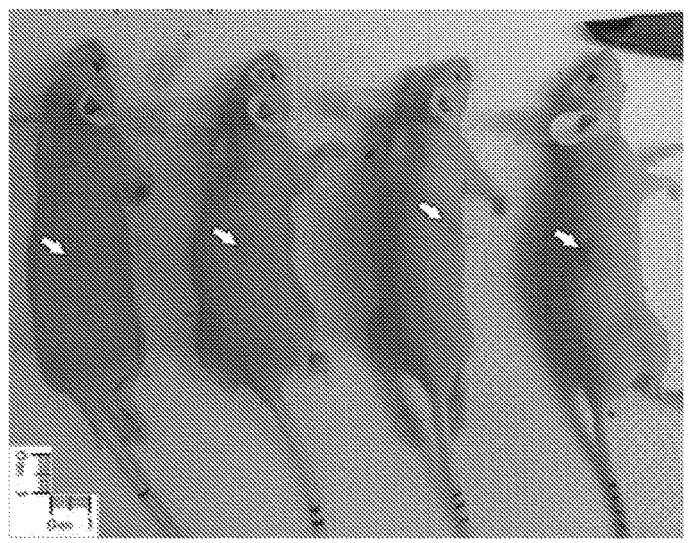

To further assess the inhibitory effect of molecular aggregates of 1 to cancer cells, we inoculated HeLa cells on nude mice and treated the xenograft tumors with molecular aggregates of 1 by peritumoral injection. As shown in FIG. 2g, although 1 at 0.5 mM (~1 mg/kg) has little effect on tumor growth, 1 at 5 mM (~10 mg/kg) starts to inhibit tumor progression after 10th day of treatment (after 3 doses). The appearance of mice on the 19th day of treatment evidently shows the inhibitory effect of 1 at 5 mM (FIG. 2h and FIGS. 11b, c and d). Tumors on the mice from the group treated by 5 mM of 1 are significantly smaller than the tumor on mice from the group treated by 0.5 mM of 1 and the control group. Moreover, the surface of the skin covering and around the tumor is intact (with no ulceration or sclerosis) on every mice treated with 5 mM of 1, and their body weights are similar with mice in control group (FIG. 11a), indicating that the molecular aggregates unlikely elicit inflammation response in skin tissue of the mice or cause any severe side effects.

Example 4—Cellular Response of Cancer Cells Towards the Molecular Aggregates

Figure 3A:
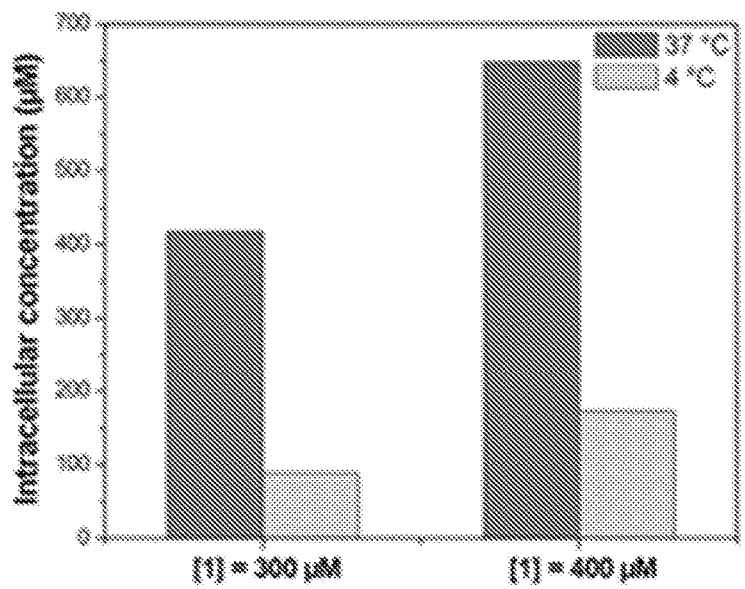
FIG. 3 depicts the response of cancer cells toward molecular aggregates of 1. (a) Intracellular concentration of 1 in HeLa cells treated with 1 for 12 h at different temperatures measure by LC-MS (left bar=37° C.; right bar=4° C.). (b) Confocal images of FITC annexin V and PI stained HeLa cells without incubation with 1 (live cells), HeLa cells treated with 400 μM of 1 for 36 h, and necrotic HeLa cells (induced by DMSO). Scale bar=20 μm. (c) Fluorescence emission of 7-AAD and 1 in cell lysate (15,000 cell/mL) at $\lambda_{ex}$=488 nm. (d) Cell cycle analysis, by flow cytometry, of HeLa cells treated with 0, 300 or 400 μM of 1 for 24 h. Depletion of G2/M phase occurs in cells treated with 400 μM of 1. (e) Cell migration assay of HeLa cells treated with 0, 300, 400 or 500 μM of 1. The gaps were created on the HeLa cells of 100% confluence in 24 well plates, and measured after incubation for 18 h.

The cytotoxicity of the molecular aggregates of 1 toward the cancer cells in cell assays and on animal model warrants further examination on the mechanism of the cell death. Since both extracellular stimuli and intracellular signaling regulate cell-cycle and cell migration, we examined whether the aggregates of 1 enter the HeLa cells. We measured the intracellular concentrations of 1 in the lysate of the HeLa cells incubated with 300 µM and 400 µM of 1 for 24 h (FIG. 3a) at 37° C. or 4° C. Based on the amount of 1, measured by liquid chromatography-mass spectroscopy (LC-MS) and the estimated total cell volume, the concentration of 1 inside the cells is about 150% of the concentration of 1 used for the incubation at 37° C. But, at 4° C., there is much less of 1 (about 30% of the incubating concentration) inside the cells than outside the cells (in the culture media). This result implies the accumulation of both monomers and the aggregates of 1 inside cells likely via processes of active transport.

Figure 3B:
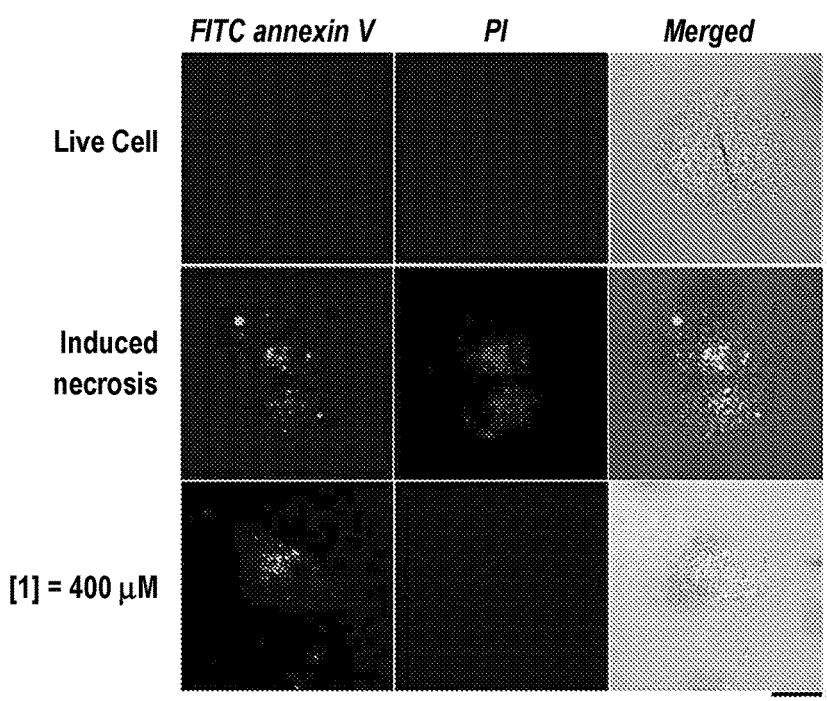

To determine the process of cell death induced by the aggregates of 1, we used FITC conjugated annexin V and propidium iodide (PI) to stain the cells (FIG. 3b). Being membrane impermeable, PI discriminates viable cells from late apoptotic or necrotic cells, and FITC conjugated annexin V binds to plasma membrane of apoptotic and necrotic cells as the former ones have extracellular exposed phosphatidylserine and the latter ones lose membrane integrity. Unlike induced necrotic cells that can be stained by both dyes and viable cells that exclude both dyes, most of the HeLa cells treated by 400 µM of 1 for 36 h exclude PI, but their plasma membranes are stained green by FITC annexin V, indicating that the aggregates of 1 induce apoptosis of the HeLa cells.

Figure 3C:
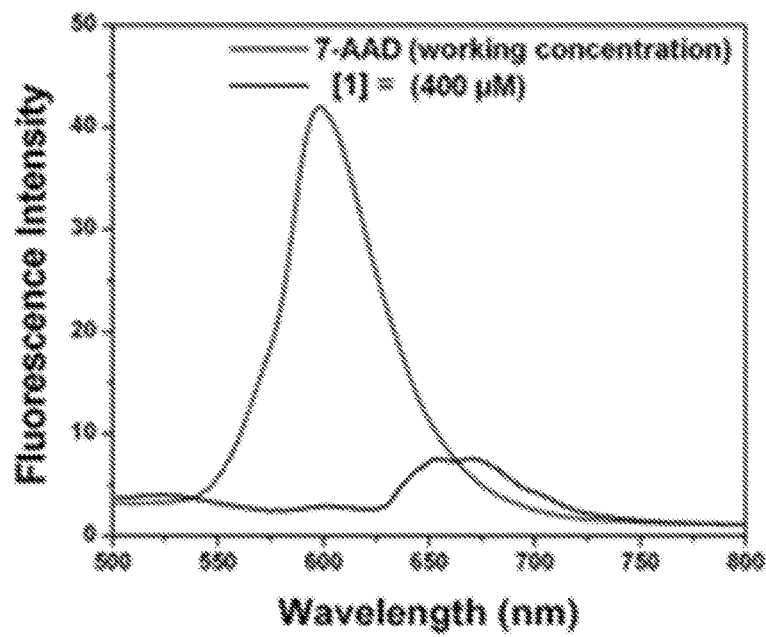

Because apoptosis associates with cell cycle, we examined the effect of the aggregates of 1 on the cell cycle. FIG. 3d shows the flow cytometry cellcycle analysis of the HeLa cells incubated with 1 at different concentrations. The cellcycle distribution of the HeLa cells incubated with 300 µM of 1, showing a large peak of G0/G1 phase and a small peak of G2/M phase that are connected by the S phase, is similar to the cell-cycle distribution of the untreated HeLa cells. The cell-cycle distribution of the HeLa cells incubated with 400 µM of 1 indicates significant decrease of the peaks of S phase and G2/M phase. Thus, the aggregates of 1 arrest the HeLa cells at the G1/G0 phase and consequently prevent cell mitosis. The slight right shift of the whole spectra results from the overlapping of emission of 7-AAD and 1 (FIG. 3c). But such shift barely hampers the distribution of cell-cycle of the spectra. The aggregates of 1 also delay the migration of the HeLa cells. As shown in cell migration assay (FIG. 3e), after 18 h of culture, the untreated cells and the cells incubated with 300 µM of 1 exhibit similar migration rates and cover 47% of the gaps. After incubation with 400 or 500 µM of 1 for 18 h, the HeLa cells only cover 27% of the gaps, indicating that the aggregates of 1 delay the migration of the cells.

Example 5—Protein Targets of the Molecular Aggregates

Figure 4:
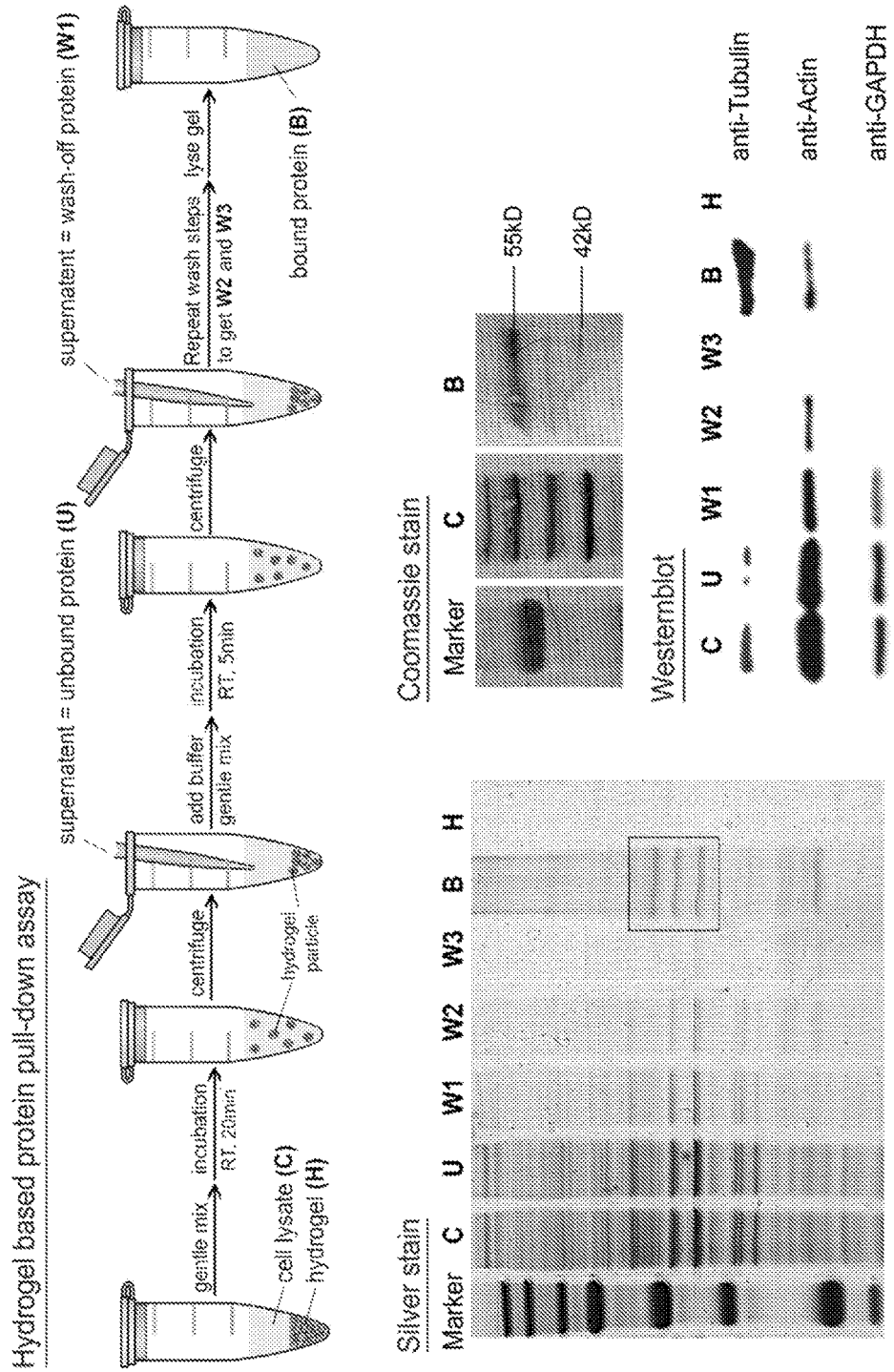
FIG. 4 depicts a hydrogel based protein pull-down assay. Collected samples are: complete cell lysate (C), unbound protein (U), wash-off proteins (W1, W2 and W3), proteins that bound specifically with hydrogel (B) and hydrogel itself as background (H). After SDSPAGE, the protein constituent of each sample was analyzed by silver stain, Coomassie stain, and the identity of the cytoskeletal proteins was further confirmed by Western blot.

That 1 enters the cells to affect cell cycle, cell migration, and eventually cell viability implies the interactions between the aggregates of 1 and certain intracellular proteins. Thus, we modified a hydrogel based protein pull-down assay tailored for evaluating the interactions of the aggregates of 1 with intracellular proteins (FIG. 4). As shown in FIG. 4, hydrogel based protein pull-down assay consists of the following major steps: (1) incubating the hydrogel with a cell lysate; (2) separating the hydrogel; (3) removing the non-specific proteins; (4) analyzing the proteins (by SDS-PAGE, gel staining, and Western blot). The hydrogel of 1 consists of long and entangled fibrils, formed by the self-assembly of 1, that have diameter of 24 nm and cross-β structure, thus the hydrogel of 1 acts as an equivalent of the high density aggregates of 1. Also, it is easy to separate the hydrogel particles from aqueous solution by centrifuging after they interact with the proteins.

The hydrogel-based protein pull-down assay (FIG. 4) suggests that the aggregates of 1 interact with tubulins. Silver stain reveals that three major protein bands (within the molecular weight range of 37~75 kDa) arise from the proteins in sample B, but not from the proteins in sample W3, indicating that these three bands correspond to the proteins bound specifically to the aggregates of 1. Coomassie stain of the three bands within 3775 kDa indicates that the intensities of the bands decrease in the order of the top band (55 kDa), the bottom band (42 kDa), and the middle band (50 kDa). Because the molecular weights of tubulin and actin are around 55 kDa and 42 kDa, respectively, and our previous result indicates that a hydrogel formed by a small molecule, which is structurally similar with 1, binds with tubulin, and that these two proteins are tightly related to cell cycle and cell migration, we used anti-α-tubulin and anti-actin for Western blot. Western blot proves the existence of tubulin and actin in sample B, thus confirming the selective interaction between tubulin and actin with the aggregates of 1. In addition, the absence of tubulin in all wash-off solutions indicates that tubulin has higher affinity to the aggregates of 1 than actin does. Sample B retains only a small amount of actin, suggesting low binding affinity of actin to the aggregates of 1. At lower molecular weight range, several bands come from both the sample B and the sample W3, indicating that these proteins bind to the aggregates of 1 with low affinity and easily dissociate into aqueous medium. In the GAPDH control, the absence of GAPDH in W2, W3, and B (FIG. 4) validates that the washing steps successfully remove non-specific bound proteins from the hydrogel of 1.

Figure 5A:
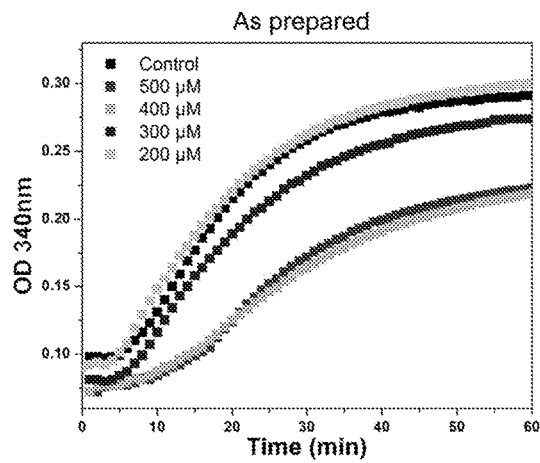
FIG. 5 depicts in vitro and cell-based assays demonstrating the interaction between tubulin and molecular aggregates of 1. Tubulin polymerization assay in the presence of 1. In vitro tubulin polymerization reactions in (a) as prepared or (c) filtered reaction cocktail without 1 (control) or with different concentrations of 1. The amount of microtubule is in proportion to optical density at 340 nm. The calculated polymerization rate ($V_{max}$) and the final tubulin polymer mass vs concentrations of 1 from tubulin polymerization in (b) as prepared or (d) filtered reaction cocktail. Negative stained TEM images of molecular aggregates of 1 binding with tubulin. Buffer (control) or 1 (final concentration at 200 to 500 μM) was introduced into reaction cocktail containing fully assembled microtubule (after 60 min of polymerization). The amount of microtubule remain unchanged after 30 min. (e) Molecular aggregates of 1 (400 μM) incubated with tubulins heterodimers in general tubulin buffer. Scale bar=40 nm. White arrows point at tubulin clusters on the molecular aggregates of 1. Confocal images of tubulin stained HeLa and other cell lines. (f) Time dependent cytotoxicity of 1 towards HeLa cells. Data are presented as mean±SD of three independent experiments. Tubulin staining of HeLa cells treated with as-prepared medium containing (g) 0 μM, (h) 200 μM, (i) 300 μM and (j) 400 μM of 1, and filtered medium (k) containing 400 μM of 1 for 24 h. Insets are 3× enlarged images. T98G (l, m) and PC12 (n, o) were also treated with as-prepared medium containing 0 or 400 μM of 1 for 24 h for tubulin staining DNA was counterstained blue by DAPI. Scale bar=10 μm. See also FIG. 12.
Figure 5B:
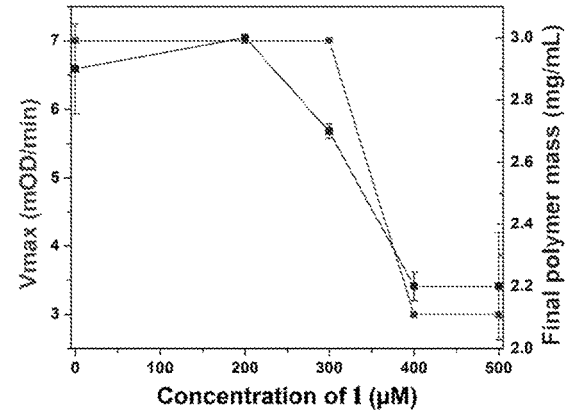
Figure 5C:
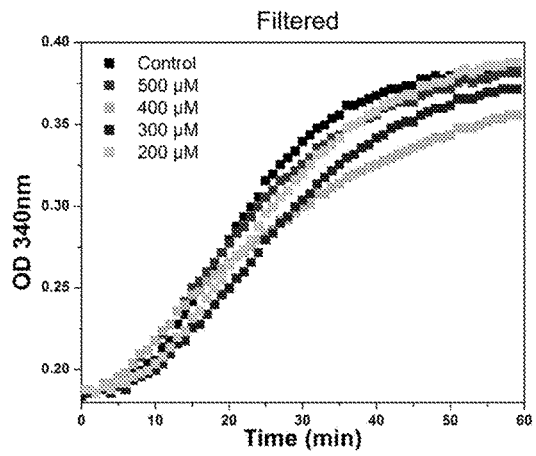
Figure 5D:
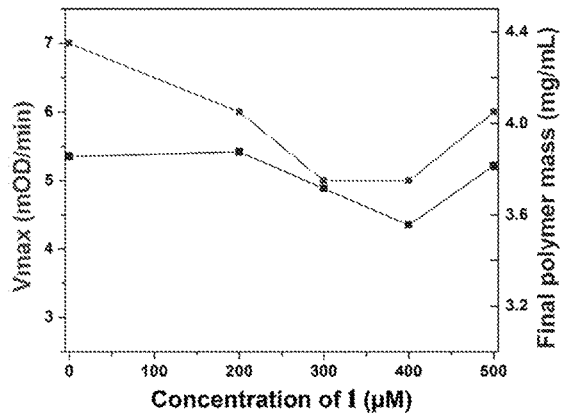

As the major function of tubulin is to polymerize into microtubule, we carried out in vitro tubulin polymerization assay to evaluate how the molecular aggregates of 1 affect the polymerization of tubulin. We incubated tubulin heterodimers (i.e., the α- and β-tubulin heterodimer, existing almost exclusively in heterodimer form in cytoplasm) with 1 at different concentrations and monitored the formation of microtubule (FIG. 5). As shown in FIG. 5a, at 200 µM of 1, the polymerization curve of tubulin almost overlaps with that of control (i.e., normal polymerization with polymerization cocktail only). At 300 µM of 1, the polymerization curve starts to deviate slightly from the control curve. At 400 and 500 µM of 1 (i.e., molecular aggregates of 1 dominate), the polymerization curves significantly deviate from the control curve. According to the rate of exponential growth phase ($V_{max}$) (FIG. 5b), while 200 µM or 300 µM of 1 barely inhibits the polymerization of tubulins, 400 or 500 µM of 1 drastically decreases the $V_{max}$ of the polymerization of tubulins. According to the final amount of polymers (i.e., microtubule), while 300 µM of 1 slightly decreases the amount of microtubules, 400 or 500 µM of 1 also significantly reduces the formation of microtubules (about 30% decrease) (FIG. 5b). To confirm that the molecular aggregates of 1, but not monomeric 1, inhibit the formation of microtubules, we filtrated of the reaction mixture by a 0.22 µm PVDF filter before the addition of tubulins. As shown in FIG. 5c, filtration of the reaction cocktail (control) hardly exhibits any effect on the polymerization of tubulins, indicating that the filtration barely disturbs tubulin polymerization. However, filtrated reaction mixtures containing 200 to 500 µM of 1 has similar polymerization curve to that of control. According to the calculated $V_{max}$ and the final amount of polymers of tubulins (FIG. 5d), 400 or 500 µM of 1, after the filtration, only causes slight decreases in both $V_{max}$ and the final amount of polymers of tubulins. Because filtration significantly minimized the inhibitory effect of 400 or 500 µM of 1 to tubulin polymerization, the molecular aggregates of 1 inhibit the formation of microtubules.

Microtubules are highly dynamic, growing and shrinking at a constant rate. To determine whether molecular aggregates of 1 achieve the inhibition of microtubule formation through preventing microtubule growth or accelerating microtubule shrinkage, we applied 1 to the polymerization mixture after most of tubulin heterodimers already formed microtubules (60 min of pre-incubation) and monitored the change of microtubules. The addition of buffer alone (control) induces little change to the microtubule, indicating that the dilution of reaction mixture barely causes any loss of microtubules. The addition of 1 (final concentration 200 to 500 µM) also induces little notable loss of microtubules. This result, being similar to that of the control, indicates that the molecular aggregates of 1 inhibit microtubule formation by preventing the growth rather than by promoting the shrinkage of microtubules.

Figure 5E:
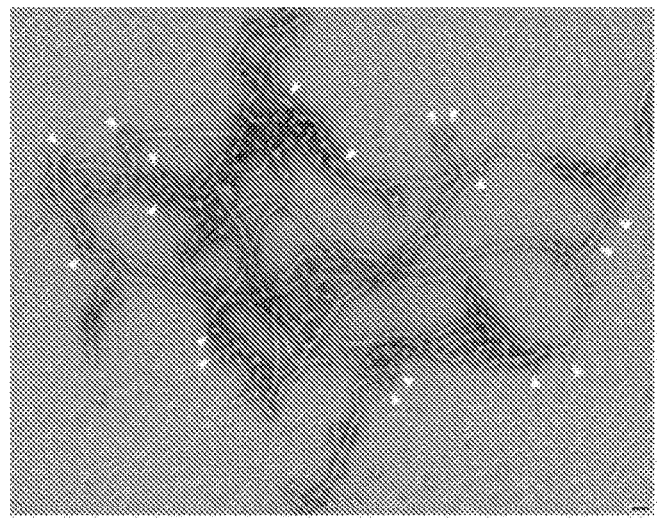
Figure 12A:
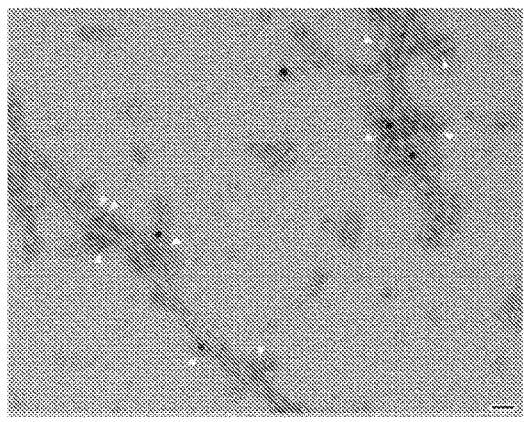
FIG. 12 depicts Negative stained TEM images of fibrillar aggregates of 1 binding with tubulin. Related to FIG. 5. (a) Molecular aggregates of 1 incubated with biotinated tubulins then stained by streptavidin@Au in general tubulin buffer; (b) molecular aggregates of 1 alone stained by streptavidin@Au in general tubulin buffer; (c) anti-β-tubulin@Au stained fibrillar aggregates of 1 like structures in lysate of HeLa cells treated with 500 μM of 1 for 24 h. White arrow heads point at biotinated tubulin. Scale bar=20 nm.
Figure 12B:
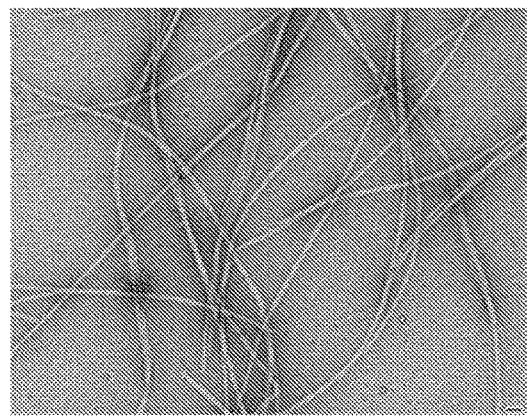
Figure 12C:
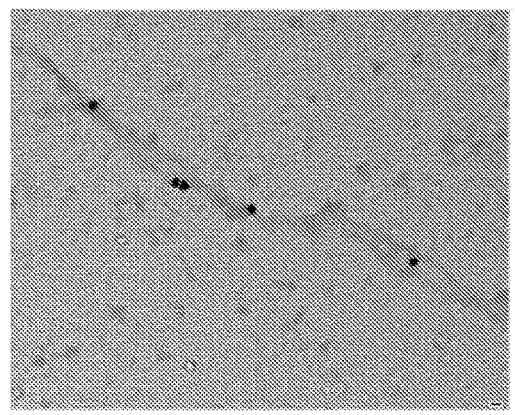

TEM images of the aggregates of 1 incubated with tubulin heterodimers confirm the interactions between the two. The TEM images of 400 µM of 1 incubated with tubulin heterodimer (20 µM, similar to the intracellular concentration of tubulin) at 25° C. show that round dots, attaching not only on the surface but also at the ends the aggregates of 1, connects the fibrillar aggregates of 1 into network (FIG. 5e). The dots have a diameter about 13±2 nm, which is larger than the size of tubulin heterodimer (8 nm in length), suggesting the presence of multiple tubulins heterodimers. The molecular aggregates of 1 have a narrower width than those formed in PBS buffer (FIG. 1a) because the incubations were carried in general tubulin buffer, which differs from that PBS buffer both in composition and pH. To confirm the dots on the aggregates of 1 are tubulin, we repeated the incubation with biotinylated tubulin heterodimers and then added streptavidin conjugated gold nanoparticles to the solution. As shown in the TEM images, the gold nanoparticles appear almost exclusively on or near the aggregates of 1 (FIG. 12a). In the absence of biotinylated tubulin heterodimers, no gold nanoparticle attaches to the aggregates of 1 (FIG. 12b). These results prove the presence of tubulin heterodimers on the aggregates of 1. In another experiment, we used anti-tubulin-gold nanoparticles to label tubulin in lysate of HeLa cells treated with 500 μM of 1 for 24 h. TEM image reveals that fibril-like structures, which evidently differ from those of microtubules, attached with gold nanoparticles (FIG. 12c), suggesting that the interactions between molecular aggregates of 1 and tubulin heterodimers might also occur inside cells.

Example 6—The Molecular Aggregates Interact with Cytoskeletal Proteins in Cells

Figure 5F:
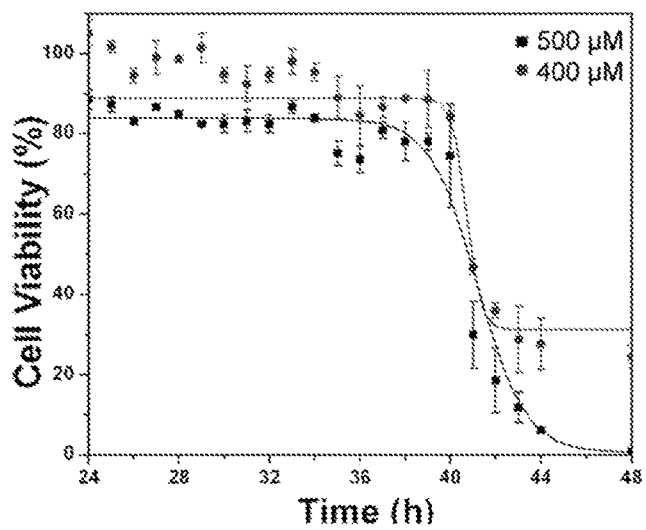
Figures 5G, 5H, 5I:
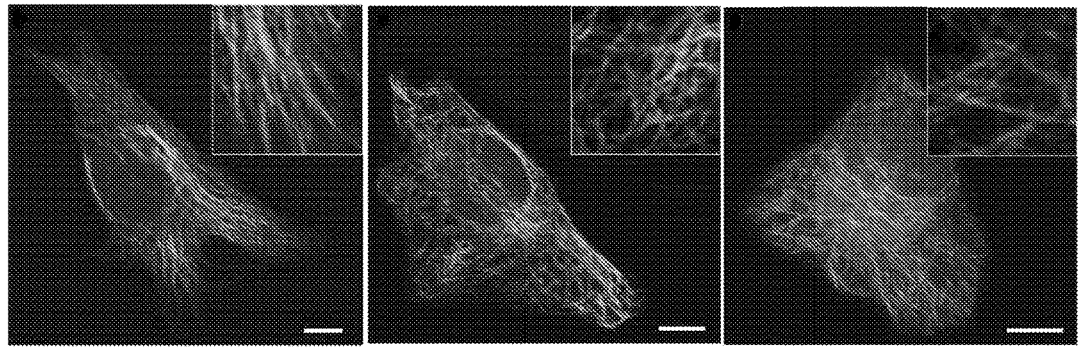
Figures 5J, 5K:
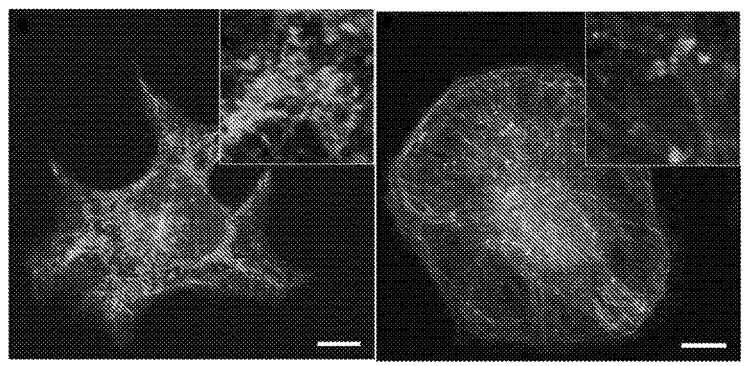
Figures 5L, 5M, 5N, 5O:
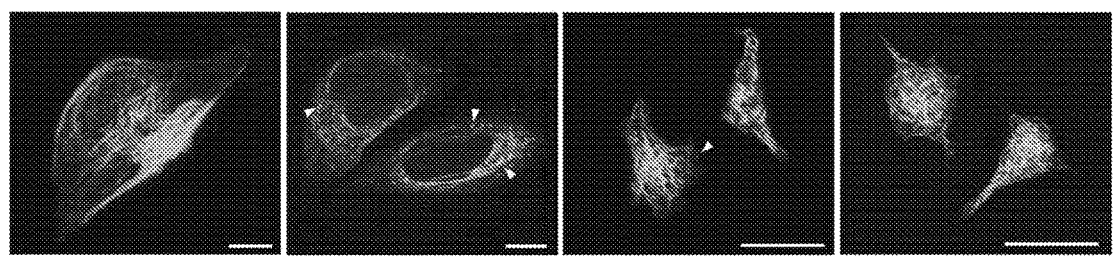

To confirm that the aggregates of 1 clusters multiple tubulin heterodimers and inhibit the formation of microtubules inside live cells, we used a tubulin tracker that selectively binds to tubulin polymers (microtubules) over tubulin monomers to stain the HeLa cells treated with 1 at different concentrations for 24 h. The time dependent viability of the HeLa cells treated with 1 at 400 and 500 μM indicates little loss of cell viability until after 38 h of incubation (FIG. 5f). Thus, at 24 h of incubation, the change in the morphology of microtubule (unlikely resulted from cell death) reveals the interaction between the molecular aggregates of 1 and tubulins. As shown in FIG. 5g, the untreated cells (i.e., the control) displays long, smooth microtubule fibrils stretching through the cell body. The microtubules in the HeLa cells treated with 200 μM of 1 (FIG. 5h) exhibit essentially the same morphology and distribution as those in the control cells. In the HeLa cells treated with 300 μM of 1, the microtubules extend cross the cell body, but a small amount of the microtubules appear to be shorter than those in the control cells (FIG. 5i). This result coincides with the observation that 1, at 300 μM, slightly decreases the final amount of the microtubules in the in vitro tubulin polymerization assay (FIG. 5b). As shown in FIG. 5j, the dominate morphology of tubulins, in the HeLa cells treated with 400 μM of 1, is large clusters surrounded by scattered microtubule fibrils, which differs completely from that of the control. As the tubulin tracker only stains microtubule (i.e., polymerized tubulin heterodimers), the fluorescence from the cluster indicates the tubulin heterodimers in the clusters are short microtubules. Upon incubation with medium that initially contains 400 μM of 1 but filtered by 0.22 μm PVDF membrane, the cells display (almost) normal microtubule networks, with only few clusters (FIG. 5k). These observations, together with the results from tubulin polymerization assay and TEM images, demonstrate that the molecular aggregates of 1 cluster tubulin heterodimers in the form of short microtubules and prevent the growth of microtubules (FIG. 6). The loss of microtubules induced by molecular aggregates of 1 explains the origins of the delay of cell migration and the arrest of cell-cycle in HeLa cells incubated with 400 or 500 μM of 1. In addition, upon incubation with 400 μM of 1, T98G cells, a glioblastoma cell line, also have disrupted microtubule network and show clusters of short microtubules (FIG. 5m). Unlike in HeLa and T98G cells, the microtubules in the PC12 cells treated by 400 μM of 1 still form intact microtubule networks (FIG. 5o) that span through the cell body and exhibit little difference with that in the untreated PC12 cells (FIG. 5n), suggesting there is insignificant disruption of the formation of microtubules by the aggregates of 1 in PC12 cells after 24 h incubation with 1 at 400 μM.

INCORPORATION BY REFERENCE

All of the U.S. patents and U.S. patent application publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A method of treating cancer, comprising the step of: administering to a subject in need thereof a plurality of hydrophobic, self-assembling monomers of Formula (I):

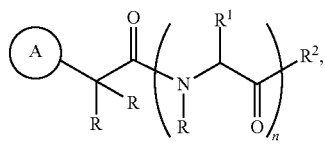

wherein independently for each occurrence:

is naphthyl;

R is H or alkyl;
$R^1$ is substituted or unsubstituted aralkyl or heteroaralkyl;
$R^2$ is H, alkyl, —OR, or —$NR_2$; and
n is 2, 3, 4, 5, or 6;
wherein $R^1$ is an unsubstituted aralkyl for at least one of said $R^1$ groups and $R^1$ is a substituted aralkyl or substituted heteroarylalkyl for at least one of said $R^1$ groups; and
wherein the cancer is selected from the group consisting of cervical carcinoma, hepatocarcinoma, glioblastoma, breast carcinoma, pancreatic carcinoma, and uterine sarcoma.

2. The method of claim 1, wherein the cancer is glioblastoma.

3. The method of claim 1, wherein the hydrophobic, self-assembling monomer comprises a dipeptide.

4. The method of claim 1, wherein R is H.

5. The method of claim 1, wherein $R^1$ is substituted aralkyl for at least one of said $R^1$ groups.

6. The method of claim 1, wherein $R^1$ is hydroxyaralkyl for at least one of said $R^1$ groups.

7. The method of claim 1, wherein $R^1$ is benzyl for at least one of said $R^1$ groups.

8. The method of claim 1, wherein $R^1$ is substituted benzyl for at least one of said $R^1$ groups.

9. The method of claim 1, wherein $R^1$ is hydroxybenzyl for at least one of said $R^1$ groups.

10. The method of claim 1, wherein $R^1$ is 4-hydroxybenzyl for at least one of said $R^1$ groups.

11. The method of claim 1, wherein $R^2$ is —OR or —$NR_2$.

12. The method of claim 1, wherein $R^2$ is —OR.

13. The method of claim 1, wherein $R^2$ is —OH.

14. The method of claim 1, wherein n is 2, 3, 4, or 5.

15. The method of claim 1, wherein n is 3, 4, 5, or 6; and $R^1$ is benzyl for two of said $R^1$ groups.

16. The method of claim 1, wherein the monomers of Formula (I) are present at a concentration of 200 µM or greater.

17. The method of claim 1, wherein the monomers of Formula (I) are present at a concentration of 200 µM to 600 µM.

18. A method of treating cancer, comprising the step of: administering to a subject in need thereof a plurality of hydrophobic, self-assembling monomers, wherein the hydrophobic, self-assembling monomer is

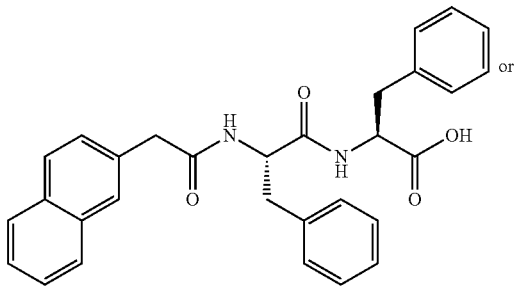

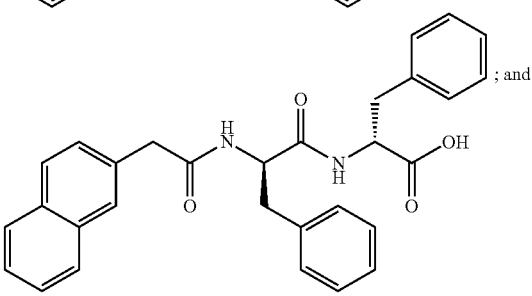

wherein the cancer is selected from the group consisting of cervical carcinoma, hepatocarcinoma, glioblastoma, breast carcinoma, pancreatic carcinoma, and uterine carcinoma.

* * * * *

SEQUENCE LISTING

```
<160> NUMBER OF SEQ ID NOS: 481

<210> SEQ ID NO 1
<211> LENGTH: 14
<212> TYPE: PRT
<213> ORGANISM: Artificial Sequence
<220> FEATURE:
<223> OTHER INFORMATION: peptide fragment of beta tubulin

<400> SEQUENCE: 1

Lys Glu Val Asp Glu Gln Met Leu Asn Val Gln Asn Lys Asn
1               5                   10

<210> SEQ ID NO 2
<211> LENGTH: 29
<212> TYPE: PRT
<213> ORGANISM: Artificial Sequence
<220> FEATURE:
<223> OTHER INFORMATION: peptide fragment of beta tubulin

<400> SEQUENCE: 2
```

```
Lys Phe Trp Glu Val Ile Ser Asp Glu His Gly Ile Asp Pro Thr Gly
1               5                   10                  15

Thr Tyr His Gly Asp Ser Asp Leu Gln Leu Glu Arg Ile
            20                  25

<210> SEQ ID NO 3
<211> LENGTH: 20
<212> TYPE: PRT
<213> ORGANISM: Artificial Sequence
<220> FEATURE:
<223> OTHER INFORMATION: peptide fragment of beta tubulin

<400> SEQUENCE: 3

Lys Gly His Tyr Thr Glu Gly Ala Glu Leu Val Asp Ser Val Leu Asp
1               5                   10                  15

Val Val Arg Lys
            20

<210> SEQ ID NO 4
<211> LENGTH: 21
<212> TYPE: PRT
<213> ORGANISM: Artificial Sequence
<220> FEATURE:
<223> OTHER INFORMATION: peptide fragment of beta tubulin

<400> SEQUENCE: 4

Lys Gly His Tyr Thr Glu Gly Ala Glu Leu Val Asp Ser Val Leu Asp
1               5                   10                  15

Val Val Arg Lys Glu
            20

<210> SEQ ID NO 5
<211> LENGTH: 27
<212> TYPE: PRT
<213> ORGANISM: Artificial Sequence
<220> FEATURE:
<223> OTHER INFORMATION: peptide fragment of beta tubulin

<400> SEQUENCE: 5

Lys Leu Thr Thr Pro Thr Tyr Gly Asp Leu Asn His Leu Val Ser Ala
1               5                   10                  15

Thr Met Ser Gly Val Thr Thr Cys Leu Arg Phe
            20                  25

<210> SEQ ID NO 6
<211> LENGTH: 11
<212> TYPE: PRT
<213> ORGANISM: Artificial Sequence
<220> FEATURE:
<223> OTHER INFORMATION: peptide fragment of beta tubulin

<400> SEQUENCE: 6

Lys Asn Met Met Ala Ala Cys Asp Pro Arg His
1               5                   10

<210> SEQ ID NO 7
<211> LENGTH: 16
<212> TYPE: PRT
<213> ORGANISM: Artificial Sequence
<220> FEATURE:
<223> OTHER INFORMATION: peptide fragment of beta tubulin

<400> SEQUENCE: 7

Lys Asn Ser Ser Tyr Phe Val Glu Trp Ile Pro Asn Asn Val Lys Thr
1               5                   10                  15
```

```
<210> SEQ ID NO 8
<211> LENGTH: 13
<212> TYPE: PRT
<213> ORGANISM: Artificial Sequence
<220> FEATURE:
<223> OTHER INFORMATION: peptide fragment of beta tubulin

<400> SEQUENCE: 8

Lys Arg Ile Ser Glu Gln Phe Thr Ala Met Phe Arg Arg
1               5                   10

<210> SEQ ID NO 9
<211> LENGTH: 17
<212> TYPE: PRT
<213> ORGANISM: Artificial Sequence
<220> FEATURE:
<223> OTHER INFORMATION: peptide fragment of beta tubulin

<400> SEQUENCE: 9

Arg Ala Leu Thr Val Pro Glu Leu Thr Gln Gln Met Phe Asp Ala Lys
1               5                   10                  15

Asn

<210> SEQ ID NO 10
<211> LENGTH: 17
<212> TYPE: PRT
<213> ORGANISM: Artificial Sequence
<220> FEATURE:
<223> OTHER INFORMATION: peptide fragment of beta tubulin

<400> SEQUENCE: 10

Arg Ala Val Leu Val Asp Leu Glu Pro Gly Thr Met Asp Ser Val Arg
1               5                   10                  15

Ser

<210> SEQ ID NO 11
<211> LENGTH: 18
<212> TYPE: PRT
<213> ORGANISM: Artificial Sequence
<220> FEATURE:
<223> OTHER INFORMATION: peptide fragment of beta tubulin

<400> SEQUENCE: 11

Arg Glu Ile Val His Leu Gln Ala Gly Gln Cys Asn Gln Ile Gly Ala
1               5                   10                  15

Lys Phe

<210> SEQ ID NO 12
<211> LENGTH: 14
<212> TYPE: PRT
<213> ORGANISM: Artificial Sequence
<220> FEATURE:
<223> OTHER INFORMATION: peptide fragment of beta tubulin

<400> SEQUENCE: 12

Arg Ile Met Asn Thr Phe Ser Val Val Pro Ser Pro Lys Val
1               5                   10

<210> SEQ ID NO 13
<211> LENGTH: 14
<212> TYPE: PRT
<213> ORGANISM: Artificial Sequence
<220> FEATURE:
<223> OTHER INFORMATION: peptide fragment of beta tubulin
```

<400> SEQUENCE: 13

Arg Ile Asn Val Tyr Tyr Asn Glu Ala Thr Gly Gly Lys Tyr
1               5                   10

<210> SEQ ID NO 14
<211> LENGTH: 12
<212> TYPE: PRT
<213> ORGANISM: Artificial Sequence
<220> FEATURE:
<223> OTHER INFORMATION: peptide fragment of beta tubulin

<400> SEQUENCE: 14

Arg Ile Ser Glu Gln Phe Thr Ala Met Phe Arg Arg
1               5                   10

<210> SEQ ID NO 15
<211> LENGTH: 16
<212> TYPE: PRT
<213> ORGANISM: Artificial Sequence
<220> FEATURE:
<223> OTHER INFORMATION: peptide fragment of beta tubulin

<400> SEQUENCE: 15

Arg Leu His Phe Phe Met Pro Gly Phe Ala Pro Leu Thr Ser Arg Gly
1               5                   10                  15

<210> SEQ ID NO 16
<211> LENGTH: 18
<212> TYPE: PRT
<213> ORGANISM: Artificial Sequence
<220> FEATURE:
<223> OTHER INFORMATION: peptide fragment of beta tubulin

<400> SEQUENCE: 16

Arg Met Ser Met Lys Glu Val Asp Glu Gln Met Leu Asn Val Gln Asn
1               5                   10                  15

Lys Asn

<210> SEQ ID NO 17
<211> LENGTH: 28
<212> TYPE: PRT
<213> ORGANISM: Artificial Sequence
<220> FEATURE:
<223> OTHER INFORMATION: peptide fragment of beta tubulin

<400> SEQUENCE: 17

Arg Ser Gly Pro Phe Gly Gln Ile Phe Arg Pro Asp Asn Phe Val Phe
1               5                   10                  15

Gly Gln Ser Gly Ala Gly Asn Asn Trp Ala Lys Gly
            20                  25

<210> SEQ ID NO 18
<211> LENGTH: 11
<212> TYPE: PRT
<213> ORGANISM: Artificial Sequence
<220> FEATURE:
<223> OTHER INFORMATION: peptide fragment of beta tubulin

<400> SEQUENCE: 18

Arg Tyr Leu Thr Val Ala Ala Val Phe Arg Gly
1               5                   10

<210> SEQ ID NO 19
<211> LENGTH: 29

```
<212> TYPE: PRT
<213> ORGANISM: Artificial Sequence
<220> FEATURE:
<223> OTHER INFORMATION: peptide fragment of beta tubulin

<400> SEQUENCE: 19

Lys Phe Trp Glu Val Ile Ser Asp Glu His Gly Ile Asp Pro Thr Gly
1               5                   10                  15

Thr Tyr His Gly Asp Ser Asp Leu Gln Leu Asp Arg Ile
            20                  25

<210> SEQ ID NO 20
<211> LENGTH: 19
<212> TYPE: PRT
<213> ORGANISM: Artificial Sequence
<220> FEATURE:
<223> OTHER INFORMATION: peptide fragment of beta tubulin

<400> SEQUENCE: 20

Lys Met Ala Val Thr Phe Ile Gly Asn Ser Thr Ala Ile Gln Glu Leu
1               5                   10                  15

Phe Lys Arg

<210> SEQ ID NO 21
<211> LENGTH: 17
<212> TYPE: PRT
<213> ORGANISM: Artificial Sequence
<220> FEATURE:
<223> OTHER INFORMATION: peptide fragment of beta tubulin

<400> SEQUENCE: 21

Arg Ala Ile Leu Val Asp Leu Glu Pro Gly Thr Met Asp Ser Val Arg
1               5                   10                  15

Ser

<210> SEQ ID NO 22
<211> LENGTH: 17
<212> TYPE: PRT
<213> ORGANISM: Artificial Sequence
<220> FEATURE:
<223> OTHER INFORMATION: peptide fragment of beta tubulin

<400> SEQUENCE: 22

Arg Ala Leu Thr Val Pro Glu Leu Thr Gln Gln Val Phe Asp Ala Lys
1               5                   10                  15

Asn

<210> SEQ ID NO 23
<211> LENGTH: 19
<212> TYPE: PRT
<213> ORGANISM: Artificial Sequence
<220> FEATURE:
<223> OTHER INFORMATION: peptide fragment of beta tubulin

<400> SEQUENCE: 23

Arg Glu Ile Val His Ile Gln Ala Gly Gln Cys Gly Asn Gln Ile Gly
1               5                   10                  15

Ala Lys Phe

<210> SEQ ID NO 24
<211> LENGTH: 14
<212> TYPE: PRT
<213> ORGANISM: Artificial Sequence
<220> FEATURE:
```

```
<223> OTHER INFORMATION: peptide fragment of beta tubulin

<400> SEQUENCE: 24

Arg Ile Ser Val Tyr Tyr Asn Glu Ala Thr Gly Gly Lys Tyr
1               5                   10

<210> SEQ ID NO 25
<211> LENGTH: 29
<212> TYPE: PRT
<213> ORGANISM: Artificial Sequence
<220> FEATURE:
<223> OTHER INFORMATION: peptide fragment of beta tubulin

<400> SEQUENCE: 25

Lys Phe Trp Glu Val Ile Ser Asp Glu His Gly Ile Asp Pro Ala Gly
1               5                   10                  15

Gly Tyr Val Gly Asp Ser Ala Leu Gln Leu Glu Arg Ile
            20                  25

<210> SEQ ID NO 26
<211> LENGTH: 27
<212> TYPE: PRT
<213> ORGANISM: Artificial Sequence
<220> FEATURE:
<223> OTHER INFORMATION: peptide fragment of beta tubulin

<400> SEQUENCE: 26

Lys Leu Thr Thr Pro Thr Tyr Gly Asp Leu Asn His Leu Val Ser Ala
1               5                   10                  15

Thr Met Ser Gly Val Thr Thr Ser Leu Arg Phe
            20                  25

<210> SEQ ID NO 27
<211> LENGTH: 17
<212> TYPE: PRT
<213> ORGANISM: Artificial Sequence
<220> FEATURE:
<223> OTHER INFORMATION: peptide fragment of beta tubulin

<400> SEQUENCE: 27

Arg Ala Leu Thr Val Pro Glu Leu Thr Gln Gln Met Phe Asp Ala Arg
1               5                   10                  15

Asn

<210> SEQ ID NO 28
<211> LENGTH: 12
<212> TYPE: PRT
<213> ORGANISM: Artificial Sequence
<220> FEATURE:
<223> OTHER INFORMATION: peptide fragment of beta tubulin

<400> SEQUENCE: 28

Arg Ile Ser Glu Gln Phe Ser Ala Met Phe Arg Arg
1               5                   10

<210> SEQ ID NO 29
<211> LENGTH: 14
<212> TYPE: PRT
<213> ORGANISM: Artificial Sequence
<220> FEATURE:
<223> OTHER INFORMATION: peptide fragment of beta tubulin

<400> SEQUENCE: 29

Lys Glu Val Asp Glu Gln Met Leu Ala Ile Gln Ser Lys Asn
1               5                   10
```

<210> SEQ ID NO 30
<211> LENGTH: 27
<212> TYPE: PRT
<213> ORGANISM: Artificial Sequence
<220> FEATURE:
<223> OTHER INFORMATION: peptide fragment of beta tubulin

<400> SEQUENCE: 30

Lys Leu Ala Thr Pro Thr Tyr Gly Asp Leu Asn His Leu Val Ser Ala
1               5                   10                  15

Thr Met Ser Gly Val Thr Thr Ser Leu Arg Phe
            20                  25

<210> SEQ ID NO 31
<211> LENGTH: 19
<212> TYPE: PRT
<213> ORGANISM: Artificial Sequence
<220> FEATURE:
<223> OTHER INFORMATION: peptide fragment of beta tubulin

<400> SEQUENCE: 31

Lys Met Ser Ser Thr Phe Ile Gly Asn Ser Thr Ala Ile Gln Glu Leu
1               5                   10                  15

Phe Lys Arg

<210> SEQ ID NO 32
<211> LENGTH: 14
<212> TYPE: PRT
<213> ORGANISM: Artificial Sequence
<220> FEATURE:
<223> OTHER INFORMATION: peptide fragment of beta tubulin

<400> SEQUENCE: 32

Arg Ile Ser Val Tyr Tyr Asn Glu Ala Ser Ser His Lys Tyr
1               5                   10

<210> SEQ ID NO 33
<211> LENGTH: 11
<212> TYPE: PRT
<213> ORGANISM: Artificial Sequence
<220> FEATURE:
<223> OTHER INFORMATION: peptide fragment of beta tubulin

<400> SEQUENCE: 33

Arg Tyr Leu Thr Val Ala Thr Val Phe Arg Gly
1               5                   10

<210> SEQ ID NO 34
<211> LENGTH: 10
<212> TYPE: PRT
<213> ORGANISM: Artificial Sequence
<220> FEATURE:
<223> OTHER INFORMATION: peptide fragment of beta tubulin

<400> SEQUENCE: 34

Lys Ile Arg Glu Glu Tyr Pro Asp Arg Ile
1               5                   10

<210> SEQ ID NO 35
<211> LENGTH: 12
<212> TYPE: PRT
<213> ORGANISM: Artificial Sequence
<220> FEATURE:
<223> OTHER INFORMATION: peptide fragment of beta tubulin

```
<400> SEQUENCE: 35

Lys Leu Ala Val Asn Met Val Pro Phe Pro Arg Leu
1               5                   10

<210> SEQ ID NO 36
<211> LENGTH: 12
<212> TYPE: PRT
<213> ORGANISM: Artificial Sequence
<220> FEATURE:
<223> OTHER INFORMATION: peptide fragment of beta tubulin

<400> SEQUENCE: 36

Arg Phe Pro Gly Gln Leu Asn Ala Asp Leu Arg Lys
1               5                   10

<210> SEQ ID NO 37
<211> LENGTH: 13
<212> TYPE: PRT
<213> ORGANISM: Artificial Sequence
<220> FEATURE:
<223> OTHER INFORMATION: peptide fragment of beta tubulin

<400> SEQUENCE: 37

Arg Phe Pro Gly Gln Leu Asn Ala Asp Leu Arg Lys Leu
1               5                   10

<210> SEQ ID NO 38
<211> LENGTH: 13
<212> TYPE: PRT
<213> ORGANISM: Artificial Sequence
<220> FEATURE:
<223> OTHER INFORMATION: peptide fragment of beta tubulin

<400> SEQUENCE: 38

Arg Lys Leu Ala Val Asn Met Val Pro Phe Pro Arg Leu
1               5                   10

<210> SEQ ID NO 39
<211> LENGTH: 17
<212> TYPE: PRT
<213> ORGANISM: Artificial Sequence
<220> FEATURE:
<223> OTHER INFORMATION: peptide fragment of beta tubulin

<400> SEQUENCE: 39

Arg Ala Ala Leu Val Asp Leu Glu Pro Gly Thr Met Asp Ser Val Arg
1               5                   10                  15

Ser

<210> SEQ ID NO 40
<211> LENGTH: 28
<212> TYPE: PRT
<213> ORGANISM: Artificial Sequence
<220> FEATURE:
<223> OTHER INFORMATION: peptide fragment of beta tubulin

<400> SEQUENCE: 40

Arg Ser Gly Pro Phe Gly Gln Leu Phe Arg Pro Asp Asn Phe Ile Phe
1               5                   10                  15

Gly Gln Thr Gly Ala Gly Asn Asn Trp Ala Lys Gly
            20                  25

<210> SEQ ID NO 41
<211> LENGTH: 17
<212> TYPE: PRT
```

```
<213> ORGANISM: Artificial Sequence
<220> FEATURE:
<223> OTHER INFORMATION: peptide fragment of beta tubulin

<400> SEQUENCE: 41

Arg Ala Leu Thr Val Pro Glu Leu Thr Gln Gln Met Phe Asp Ser Lys
1               5                   10                  15

Asn

<210> SEQ ID NO 42
<211> LENGTH: 13
<212> TYPE: PRT
<213> ORGANISM: Artificial Sequence
<220> FEATURE:
<223> OTHER INFORMATION: peptide fragment of beta tubulin

<400> SEQUENCE: 42

Arg Met Asn Thr Phe Ser Val Met Pro Ser Pro Lys Val
1               5                   10

<210> SEQ ID NO 43
<211> LENGTH: 14
<212> TYPE: PRT
<213> ORGANISM: Artificial Sequence
<220> FEATURE:
<223> OTHER INFORMATION: peptide fragment of beta tubulin

<400> SEQUENCE: 43

Arg Ile Asn Val Tyr Tyr Asn Glu Ala Ala Gly Asn Lys Tyr
1               5                   10

<210> SEQ ID NO 44
<211> LENGTH: 20
<212> TYPE: PRT
<213> ORGANISM: Artificial Sequence
<220> FEATURE:
<223> OTHER INFORMATION: peptide fragment of beta tubulin

<400> SEQUENCE: 44

Lys Gly His Tyr Thr Glu Gly Ala Glu Leu Val Asp Ala Val Leu Asp
1               5                   10                  15

Val Val Arg Lys
            20

<210> SEQ ID NO 45
<211> LENGTH: 26
<212> TYPE: PRT
<213> ORGANISM: Artificial Sequence
<220> FEATURE:
<223> OTHER INFORMATION: peptide fragment of alpha tubulin

<400> SEQUENCE: 45

Lys Ala Tyr His Glu Gln Leu Ser Val Ala Glu Ile Thr Asn Ala Cys
1               5                   10                  15

Phe Glu Pro Ala Asn Gln Met Val Lys Cys
            20                  25

<210> SEQ ID NO 46
<211> LENGTH: 12
<212> TYPE: PRT
<213> ORGANISM: Artificial Sequence
<220> FEATURE:
<223> OTHER INFORMATION: peptide fragment of alpha tubulin

<400> SEQUENCE: 46
```

```
Lys Asp Val Asn Ala Ala Ile Ala Ala Ile Lys Thr
1               5                   10
```

<210> SEQ ID NO 47
<211> LENGTH: 11
<212> TYPE: PRT
<213> ORGANISM: Artificial Sequence
<220> FEATURE:
<223> OTHER INFORMATION: peptide fragment of alpha tubulin

<400> SEQUENCE: 47

```
Lys Glu Ile Ile Asp Pro Val Leu Asp Arg Ile
1               5                   10
```

<210> SEQ ID NO 48
<211> LENGTH: 9
<212> TYPE: PRT
<213> ORGANISM: Artificial Sequence
<220> FEATURE:
<223> OTHER INFORMATION: peptide fragment of alpha tubulin

<400> SEQUENCE: 48

```
Lys Phe Asp Leu Met Tyr Ala Lys Arg
1               5
```

<210> SEQ ID NO 49
<211> LENGTH: 23
<212> TYPE: PRT
<213> ORGANISM: Artificial Sequence
<220> FEATURE:
<223> OTHER INFORMATION: peptide fragment of alpha tubulin

<400> SEQUENCE: 49

```
Lys Arg Ala Phe Val His Trp Tyr Val Gly Glu Gly Met Glu Glu Gly
1               5                   10                  15

Glu Phe Ser Glu Ala Arg Glu
            20
```

<210> SEQ ID NO 50
<211> LENGTH: 22
<212> TYPE: PRT
<213> ORGANISM: Artificial Sequence
<220> FEATURE:
<223> OTHER INFORMATION: peptide fragment of alpha tubulin

<400> SEQUENCE: 50

```
Lys Thr Ile Gly Gly Gly Asp Asp Ser Phe Thr Thr Phe Phe Cys Glu
1               5                   10                  15

Thr Gly Ala Gly Lys His
            20
```

<210> SEQ ID NO 51
<211> LENGTH: 20
<212> TYPE: PRT
<213> ORGANISM: Artificial Sequence
<220> FEATURE:
<223> OTHER INFORMATION: peptide fragment of alpha tubulin

<400> SEQUENCE: 51

```
Lys Val Gly Ile Asn Tyr Gln Pro Pro Thr Val Val Pro Gly Gly Asp
1               5                   10                  15

Leu Ala Lys Val
            20
```

<210> SEQ ID NO 52

```
<211> LENGTH: 22
<212> TYPE: PRT
<213> ORGANISM: Artificial Sequence
<220> FEATURE:
<223> OTHER INFORMATION: peptide fragment of alpha tubulin

<400> SEQUENCE: 52

Arg Ala Phe Val His Trp Tyr Val Gly Glu Gly Met Glu Glu Gly Glu
1               5                   10                  15

Phe Ser Glu Ala Arg Glu
            20

<210> SEQ ID NO 53
<211> LENGTH: 19
<212> TYPE: PRT
<213> ORGANISM: Artificial Sequence
<220> FEATURE:
<223> OTHER INFORMATION: peptide fragment of alpha tubulin

<400> SEQUENCE: 53

Arg Ala Val Cys Met Leu Ser Asn Thr Thr Ala Ile Ala Glu Ala Trp
1               5                   10                  15

Ala Arg Leu

<210> SEQ ID NO 54
<211> LENGTH: 17
<212> TYPE: PRT
<213> ORGANISM: Artificial Sequence
<220> FEATURE:
<223> OTHER INFORMATION: peptide fragment of alpha tubulin

<400> SEQUENCE: 54

Arg Ala Val Phe Val Asp Leu Glu Pro Thr Val Ile Asp Glu Ile Arg
1               5                   10                  15

Asn

<210> SEQ ID NO 55
<211> LENGTH: 10
<212> TYPE: PRT
<213> ORGANISM: Artificial Sequence
<220> FEATURE:
<223> OTHER INFORMATION: peptide fragment of alpha tubulin

<400> SEQUENCE: 55

Arg Glu Asp Met Ala Ala Leu Glu Lys Asp
1               5                   10

<210> SEQ ID NO 56
<211> LENGTH: 23
<212> TYPE: PRT
<213> ORGANISM: Artificial Sequence
<220> FEATURE:
<223> OTHER INFORMATION: peptide fragment of alpha tubulin

<400> SEQUENCE: 56

Arg Phe Asp Gly Ala Leu Asn Val Asp Leu Thr Glu Phe Gln Thr Asn
1               5                   10                  15

Leu Val Pro Tyr Pro Arg Ile
            20

<210> SEQ ID NO 57
<211> LENGTH: 9
<212> TYPE: PRT
<213> ORGANISM: Artificial Sequence
<220> FEATURE:
```

```
<223> OTHER INFORMATION: peptide fragment of alpha tubulin

<400> SEQUENCE: 57

Arg Gly His Tyr Thr Ile Gly Lys Glu
1               5

<210> SEQ ID NO 58
<211> LENGTH: 18
<212> TYPE: PRT
<213> ORGANISM: Artificial Sequence
<220> FEATURE:
<223> OTHER INFORMATION: peptide fragment of alpha tubulin

<400> SEQUENCE: 58

Arg Ile His Phe Pro Leu Ala Thr Tyr Ala Pro Val Ile Ser Ala Glu
1               5                   10                  15

Lys Ala

<210> SEQ ID NO 59
<211> LENGTH: 13
<212> TYPE: PRT
<213> ORGANISM: Artificial Sequence
<220> FEATURE:
<223> OTHER INFORMATION: peptide fragment of alpha tubulin

<400> SEQUENCE: 59

Arg Leu Asp His Lys Phe Asp Leu Met Tyr Ala Lys Arg
1               5                   10

<210> SEQ ID NO 60
<211> LENGTH: 16
<212> TYPE: PRT
<213> ORGANISM: Artificial Sequence
<220> FEATURE:
<223> OTHER INFORMATION: peptide fragment of alpha tubulin

<400> SEQUENCE: 60

Arg Leu Ile Ser Gln Ile Val Ser Ser Ile Thr Ala Ser Leu Arg Phe
1               5                   10                  15

<210> SEQ ID NO 61
<211> LENGTH: 9
<212> TYPE: PRT
<213> ORGANISM: Artificial Sequence
<220> FEATURE:
<223> OTHER INFORMATION: peptide fragment of alpha tubulin

<400> SEQUENCE: 61

Arg Leu Ser Val Asp Tyr Gly Lys Lys
1               5

<210> SEQ ID NO 62
<211> LENGTH: 10
<212> TYPE: PRT
<213> ORGANISM: Artificial Sequence
<220> FEATURE:
<223> OTHER INFORMATION: peptide fragment of alpha tubulin

<400> SEQUENCE: 62

Arg Leu Ser Val Asp Tyr Gly Lys Lys Ser
1               5                   10

<210> SEQ ID NO 63
<211> LENGTH: 16
<212> TYPE: PRT
<213> ORGANISM: Artificial Sequence
```

```
<220> FEATURE:
<223> OTHER INFORMATION: peptide fragment of alpha tubulin

<400> SEQUENCE: 63

Arg Asn Leu Asp Ile Glu Arg Pro Thr Tyr Thr Asn Leu Asn Arg Leu
1               5                   10                  15

<210> SEQ ID NO 64
<211> LENGTH: 14
<212> TYPE: PRT
<213> ORGANISM: Artificial Sequence
<220> FEATURE:
<223> OTHER INFORMATION: peptide fragment of alpha tubulin

<400> SEQUENCE: 64

Arg Gln Leu Phe His Pro Glu Gln Leu Ile Thr Gly Lys Glu
1               5                   10

<210> SEQ ID NO 65
<211> LENGTH: 23
<212> TYPE: PRT
<213> ORGANISM: Artificial Sequence
<220> FEATURE:
<223> OTHER INFORMATION: peptide fragment of alpha tubulin

<400> SEQUENCE: 65

Arg Gln Leu Phe His Pro Glu Gln Leu Ile Thr Gly Lys Glu Asp Ala
1               5                   10                  15

Ala Asn Asn Tyr Ala Arg Gly
            20

<210> SEQ ID NO 66
<211> LENGTH: 17
<212> TYPE: PRT
<213> ORGANISM: Artificial Sequence
<220> FEATURE:
<223> OTHER INFORMATION: peptide fragment of alpha tubulin

<400> SEQUENCE: 66

Arg Arg Asn Leu Asp Ile Glu Arg Pro Thr Tyr Thr Asn Leu Asn Arg
1               5                   10                  15

Leu

<210> SEQ ID NO 67
<211> LENGTH: 26
<212> TYPE: PRT
<213> ORGANISM: Artificial Sequence
<220> FEATURE:
<223> OTHER INFORMATION: peptide fragment of alpha tubulin

<400> SEQUENCE: 67

Lys Ala Tyr His Glu Gln Leu Thr Val Ala Glu Ile Thr Asn Ala Cys
1               5                   10                  15

Phe Glu Pro Ala Asn Gln Met Val Lys Cys
            20                  25

<210> SEQ ID NO 68
<211> LENGTH: 12
<212> TYPE: PRT
<213> ORGANISM: Artificial Sequence
<220> FEATURE:
<223> OTHER INFORMATION: peptide fragment of alpha tubulin

<400> SEQUENCE: 68

Lys Asp Val Asn Ala Ala Ile Ala Thr Ile Lys Thr
```

<210> SEQ ID NO 69
<211> LENGTH: 11
<212> TYPE: PRT
<213> ORGANISM: Artificial Sequence
<220> FEATURE:
<223> OTHER INFORMATION: peptide fragment of alpha tubulin

<400> SEQUENCE: 69

Lys Glu Ile Ile Asp Leu Val Leu Asp Arg Ile
1               5                   10

<210> SEQ ID NO 70
<211> LENGTH: 22
<212> TYPE: PRT
<213> ORGANISM: Artificial Sequence
<220> FEATURE:
<223> OTHER INFORMATION: peptide fragment of alpha tubulin

<400> SEQUENCE: 70

Lys Thr Ile Gly Gly Gly Asp Asp Ser Phe Asn Thr Phe Phe Ser Glu
1               5                   10                  15

Thr Gly Ala Gly Lys His
            20

<210> SEQ ID NO 71
<211> LENGTH: 17
<212> TYPE: PRT
<213> ORGANISM: Artificial Sequence
<220> FEATURE:
<223> OTHER INFORMATION: peptide fragment of alpha tubulin

<400> SEQUENCE: 71

Arg Ala Val Phe Val Asp Leu Glu Pro Thr Val Ile Asp Glu Val Arg
1               5                   10                  15

Thr

<210> SEQ ID NO 72
<211> LENGTH: 22
<212> TYPE: PRT
<213> ORGANISM: Artificial Sequence
<220> FEATURE:
<223> OTHER INFORMATION: peptide fragment of alpha tubulin

<400> SEQUENCE: 72

Lys Asp Tyr Glu Glu Val Gly Val Asp Ser Val Glu Gly Glu Gly Glu
1               5                   10                  15

Glu Glu Gly Glu Glu Tyr
            20

<210> SEQ ID NO 73
<211> LENGTH: 30
<212> TYPE: PRT
<213> ORGANISM: Artificial Sequence
<220> FEATURE:
<223> OTHER INFORMATION: peptide fragment of alpha tubulin

<400> SEQUENCE: 73

Arg Glu Asp Met Ala Ala Leu Glu Lys Asp Tyr Glu Glu Val Gly Val
1               5                   10                  15

Asp Ser Val Glu Gly Glu Gly Glu Glu Glu Gly Glu Glu Tyr
            20                  25                  30

<210> SEQ ID NO 74
<211> LENGTH: 20
<212> TYPE: PRT
<213> ORGANISM: Artificial Sequence
<220> FEATURE:
<223> OTHER INFORMATION: peptide fragment of alpha tubulin

<400> SEQUENCE: 74

Lys Asp Tyr Glu Glu Val Gly Ala Asp Ser Ala Asp Gly Glu Asp Glu
1               5                   10                  15

Gly Glu Glu Tyr
            20

<210> SEQ ID NO 75
<211> LENGTH: 28
<212> TYPE: PRT
<213> ORGANISM: Artificial Sequence
<220> FEATURE:
<223> OTHER INFORMATION: peptide fragment of alpha tubulin

<400> SEQUENCE: 75

Arg Glu Asp Met Ala Ala Leu Glu Lys Asp Tyr Glu Glu Val Gly Ala
1               5                   10                  15

Asp Ser Ala Asp Gly Glu Asp Glu Gly Glu Glu Tyr
            20                  25

<210> SEQ ID NO 76
<211> LENGTH: 16
<212> TYPE: PRT
<213> ORGANISM: Artificial Sequence
<220> FEATURE:
<223> OTHER INFORMATION: peptide fragment of alpha tubulin

<400> SEQUENCE: 76

Arg Leu Ile Gly Gln Ile Val Ser Ser Ile Thr Ala Ser Leu Arg Phe
1               5                   10                  15

<210> SEQ ID NO 77
<211> LENGTH: 14
<212> TYPE: PRT
<213> ORGANISM: Artificial Sequence
<220> FEATURE:
<223> OTHER INFORMATION: peptide fragment of alpha tubulin

<400> SEQUENCE: 77

Arg Gln Ile Phe His Pro Glu Gln Leu Ile Thr Gly Lys Glu
1               5                   10

<210> SEQ ID NO 78
<211> LENGTH: 12
<212> TYPE: PRT
<213> ORGANISM: Artificial Sequence
<220> FEATURE:
<223> OTHER INFORMATION: peptide fragment of T-complex protein 1 subunit
      beta

<400> SEQUENCE: 78

Lys Glu Ala Val Ala Met Glu Ser Tyr Ala Lys Ala
1               5                   10

<210> SEQ ID NO 79
<211> LENGTH: 16
<212> TYPE: PRT
<213> ORGANISM: Artificial Sequence
<220> FEATURE:
<223> OTHER INFORMATION: peptide fragment of T-complex protein 1 subunit
      beta

```
<400> SEQUENCE: 79

Lys Ile Leu Ile Ala Asn Thr Gly Met Asp Thr Asp Lys Ile Lys Ile
1               5                   10                  15

<210> SEQ ID NO 80
<211> LENGTH: 14
<212> TYPE: PRT
<213> ORGANISM: Artificial Sequence
<220> FEATURE:
<223> OTHER INFORMATION: peptide fragment of T-complex protein 1 subunit
      beta

<400> SEQUENCE: 80

Lys Lys Ile His Pro Gln Thr Ile Ile Ala Gly Trp Arg Glu
1               5                   10

<210> SEQ ID NO 81
<211> LENGTH: 21
<212> TYPE: PRT
<213> ORGANISM: Artificial Sequence
<220> FEATURE:
<223> OTHER INFORMATION: peptide fragment of T-complex protein 1 subunit
      beta

<400> SEQUENCE: 81

Lys Lys Leu Gly Gly Ser Leu Ala Asp Ser Tyr Leu Asp Glu Gly Phe
1               5                   10                  15

Leu Leu Asp Lys Lys
            20

<210> SEQ ID NO 82
<211> LENGTH: 22
<212> TYPE: PRT
<213> ORGANISM: Artificial Sequence
<220> FEATURE:
<223> OTHER INFORMATION: peptide fragment of T-complex protein 1 subunit
      beta

<400> SEQUENCE: 82

Lys Lys Leu Gly Gly Ser Leu Ala Asp Ser Tyr Leu Asp Glu Gly Phe
1               5                   10                  15

Leu Leu Asp Lys Lys Ile
            20

<210> SEQ ID NO 83
<211> LENGTH: 10
<212> TYPE: PRT
<213> ORGANISM: Artificial Sequence
<220> FEATURE:
<223> OTHER INFORMATION: peptide fragment of T-complex protein 1 subunit
      beta

<400> SEQUENCE: 83

Lys Leu Ala Val Glu Ala Val Leu Arg Leu
1               5                   10

<210> SEQ ID NO 84
<211> LENGTH: 20
<212> TYPE: PRT
<213> ORGANISM: Artificial Sequence
<220> FEATURE:
<223> OTHER INFORMATION: peptide fragment of T-complex protein 1 subunit
      beta

<400> SEQUENCE: 84
```

-continued

```
Lys Leu Gly Gly Ser Leu Ala Asp Ser Tyr Leu Asp Glu Gly Phe Leu
1               5                   10                  15

Leu Asp Lys Lys
            20
```

<210> SEQ ID NO 85
<211> LENGTH: 21
<212> TYPE: PRT
<213> ORGANISM: Artificial Sequence
<220> FEATURE:
<223> OTHER INFORMATION: peptide fragment of T-complex protein 1 subunit
      beta

<400> SEQUENCE: 85

```
Lys Leu Gly Gly Ser Leu Ala Asp Ser Tyr Leu Asp Glu Gly Phe Leu
1               5                   10                  15

Leu Asp Lys Lys Ile
            20
```

<210> SEQ ID NO 86
<211> LENGTH: 13
<212> TYPE: PRT
<213> ORGANISM: Artificial Sequence
<220> FEATURE:
<223> OTHER INFORMATION: peptide fragment of T-complex protein 1 subunit
      beta

<400> SEQUENCE: 86

```
Lys Leu Ile Glu Glu Val Met Ile Gly Glu Asp Lys Leu
1               5                   10
```

<210> SEQ ID NO 87
<211> LENGTH: 12
<212> TYPE: PRT
<213> ORGANISM: Artificial Sequence
<220> FEATURE:
<223> OTHER INFORMATION: peptide fragment of T-complex protein 1 subunit
      beta

<400> SEQUENCE: 87

```
Lys Asn Ile Gly Val Asp Asn Pro Ala Ala Lys Val
1               5                   10
```

<210> SEQ ID NO 88
<211> LENGTH: 13
<212> TYPE: PRT
<213> ORGANISM: Artificial Sequence
<220> FEATURE:
<223> OTHER INFORMATION: peptide fragment of T-complex protein 1 subunit
      beta

<400> SEQUENCE: 88

```
Lys Val Ala Glu Ile Glu His Ala Glu Lys Glu Lys Met
1               5                   10
```

<210> SEQ ID NO 89
<211> LENGTH: 9
<212> TYPE: PRT
<213> ORGANISM: Artificial Sequence
<220> FEATURE:
<223> OTHER INFORMATION: peptide fragment of T-complex protein 1 subunit
      beta

<400> SEQUENCE: 89

```
Lys Val Leu Val Asp Met Ser Arg Val
1               5
```

```
<210> SEQ ID NO 90
<211> LENGTH: 17
<212> TYPE: PRT
<213> ORGANISM: Artificial Sequence
<220> FEATURE:
<223> OTHER INFORMATION: peptide fragment of T-complex protein 1 subunit
      beta

<400> SEQUENCE: 90

Arg Ala Ala His Ser Glu Gly Asn Thr Thr Ala Gly Leu Asp Met Arg
1               5                   10                  15

Glu

<210> SEQ ID NO 91
<211> LENGTH: 17
<212> TYPE: PRT
<213> ORGANISM: Artificial Sequence
<220> FEATURE:
<223> OTHER INFORMATION: peptide fragment of T-complex protein 1 subunit
      beta

<400> SEQUENCE: 91

Arg Asp Ala Ser Leu Met Val Thr Asn Asp Gly Ala Thr Ile Leu Lys
1               5                   10                  15

Asn

<210> SEQ ID NO 92
<211> LENGTH: 10
<212> TYPE: PRT
<213> ORGANISM: Artificial Sequence
<220> FEATURE:
<223> OTHER INFORMATION: peptide fragment of T-complex protein 1 subunit
      beta

<400> SEQUENCE: 92

Arg Glu Ala Glu Ser Leu Ile Ala Lys Lys
1               5                   10

<210> SEQ ID NO 93
<211> LENGTH: 18
<212> TYPE: PRT
<213> ORGANISM: Artificial Sequence
<220> FEATURE:
<223> OTHER INFORMATION: peptide fragment of T-complex protein 1 subunit
      beta

<400> SEQUENCE: 93

Arg Glu Ala Leu Leu Ser Ser Ala Val Asp His Gly Ser Asp Glu Val
1               5                   10                  15

Lys Phe

<210> SEQ ID NO 94
<211> LENGTH: 21
<212> TYPE: PRT
<213> ORGANISM: Artificial Sequence
<220> FEATURE:
<223> OTHER INFORMATION: peptide fragment of T-complex protein 1 subunit
      beta

<400> SEQUENCE: 94

Arg Glu Gly Thr Ile Gly Asp Met Ala Ile Leu Gly Ile Thr Glu Ser
1               5                   10                  15

Phe Gln Val Lys Arg
            20
```

```
<210> SEQ ID NO 95
<211> LENGTH: 14
<212> TYPE: PRT
<213> ORGANISM: Artificial Sequence
<220> FEATURE:
<223> OTHER INFORMATION: peptide fragment of T-complex protein 1 subunit
      beta

<400> SEQUENCE: 95

Arg Gly Ala Thr Gln Gln Ile Leu Asp Glu Ala Glu Arg Ser
1               5                   10

<210> SEQ ID NO 96
<211> LENGTH: 22
<212> TYPE: PRT
<213> ORGANISM: Artificial Sequence
<220> FEATURE:
<223> OTHER INFORMATION: peptide fragment of T-complex protein 1 subunit
      beta

<400> SEQUENCE: 96

Arg Leu Ala Leu Val Thr Gly Gly Glu Ile Ala Ser Thr Phe Asp His
1               5                   10                  15

Pro Glu Leu Val Lys Leu
            20

<210> SEQ ID NO 97
<211> LENGTH: 16
<212> TYPE: PRT
<213> ORGANISM: Artificial Sequence
<220> FEATURE:
<223> OTHER INFORMATION: peptide fragment of T-complex protein 1 subunit
      beta

<400> SEQUENCE: 97

Arg Leu Lys Gly Ser Gly Asn Leu Glu Ala Ile His Ile Ile Lys Lys
1               5                   10                  15

<210> SEQ ID NO 98
<211> LENGTH: 17
<212> TYPE: PRT
<213> ORGANISM: Artificial Sequence
<220> FEATURE:
<223> OTHER INFORMATION: peptide fragment of T-complex protein 1 subunit
      beta

<400> SEQUENCE: 98

Arg Leu Thr Ser Phe Ile Gly Ala Ile Ala Ile Gly Asp Leu Val Lys
1               5                   10                  15

Ser

<210> SEQ ID NO 99
<211> LENGTH: 24
<212> TYPE: PRT
<213> ORGANISM: Artificial Sequence
<220> FEATURE:
<223> OTHER INFORMATION: peptide fragment of T-complex protein 1 subunit
      beta

<400> SEQUENCE: 99

Arg Met Leu Pro Thr Ile Ile Ala Asp Asn Ala Gly Tyr Asp Ser Ala
1               5                   10                  15

Asp Leu Val Ala Gln Leu Arg Ala
            20
```

-continued

```
<210> SEQ ID NO 100
<211> LENGTH: 16
<212> TYPE: PRT
<213> ORGANISM: Artificial Sequence
<220> FEATURE:
<223> OTHER INFORMATION: peptide fragment of T-complex protein 1 subunit
      beta

<400> SEQUENCE: 100

Arg Gln Asp Leu Met Asn Ile Ala Gly Thr Thr Leu Ser Ser Lys Leu
1               5                   10                  15

<210> SEQ ID NO 101
<211> LENGTH: 31
<212> TYPE: PRT
<213> ORGANISM: Artificial Sequence
<220> FEATURE:
<223> OTHER INFORMATION: peptide fragment of T-complex protein 1 subunit
      beta

<400> SEQUENCE: 101

Arg Gln Leu Ile Tyr Asn Tyr Pro Glu Gln Leu Phe Gly Ala Ala Gly
1               5                   10                  15

Val Met Ala Ile Glu His Ala Asp Phe Ala Gly Val Glu Arg Leu
            20                  25                  30

<210> SEQ ID NO 102
<211> LENGTH: 17
<212> TYPE: PRT
<213> ORGANISM: Artificial Sequence
<220> FEATURE:
<223> OTHER INFORMATION: peptide fragment of T-complex protein 1 subunit
      beta

<400> SEQUENCE: 102

Arg Gln Val Leu Leu Ser Ala Ala Glu Ala Ala Glu Val Ile Leu Arg
1               5                   10                  15

Val

<210> SEQ ID NO 103
<211> LENGTH: 24
<212> TYPE: PRT
<213> ORGANISM: Artificial Sequence
<220> FEATURE:
<223> OTHER INFORMATION: peptide fragment of T-complex protein 1 subunit
      beta

<400> SEQUENCE: 103

Arg Val Gln Asp Asp Glu Val Gly Asp Gly Thr Thr Ser Val Thr Val
1               5                   10                  15

Leu Ala Ala Glu Leu Leu Arg Glu
            20

<210> SEQ ID NO 104
<211> LENGTH: 23
<212> TYPE: PRT
<213> ORGANISM: Artificial Sequence
<220> FEATURE:
<223> OTHER INFORMATION: peptide fragment of beta actin

<400> SEQUENCE: 104

Lys Asp Leu Tyr Ala Asn Thr Val Leu Ser Gly Gly Thr Thr Met Tyr
1               5                   10                  15

Pro Gly Ile Ala Asp Arg Met
            20
```

<210> SEQ ID NO 105
<211> LENGTH: 25
<212> TYPE: PRT
<213> ORGANISM: Artificial Sequence
<220> FEATURE:
<223> OTHER INFORMATION: peptide fragment of beta actin

<400> SEQUENCE: 105

Lys Leu Cys Tyr Val Ala Leu Asp Phe Glu Gln Glu Met Ala Thr Ala
1               5                   10                  15

Ala Ser Ser Ser Ser Leu Glu Lys Ser
            20                  25

<210> SEQ ID NO 106
<211> LENGTH: 15
<212> TYPE: PRT
<213> ORGANISM: Artificial Sequence
<220> FEATURE:
<223> OTHER INFORMATION: peptide fragment of beta actin

<400> SEQUENCE: 106

Lys Gln Glu Tyr Asp Glu Ser Gly Pro Ser Ile Val His Arg Lys
1               5                   10                  15

<210> SEQ ID NO 107
<211> LENGTH: 18
<212> TYPE: PRT
<213> ORGANISM: Artificial Sequence
<220> FEATURE:
<223> OTHER INFORMATION: peptide fragment of beta actin

<400> SEQUENCE: 107

Lys Tyr Pro Ile Glu His Gly Ile Val Thr Asn Trp Asp Asp Met Glu
1               5                   10                  15

Lys Ile

<210> SEQ ID NO 108
<211> LENGTH: 30
<212> TYPE: PRT
<213> ORGANISM: Artificial Sequence
<220> FEATURE:
<223> OTHER INFORMATION: peptide fragment of beta actin

<400> SEQUENCE: 108

Arg Asp Ile Lys Glu Lys Leu Cys Tyr Val Ala Leu Asp Phe Glu Gln
1               5                   10                  15

Glu Met Ala Thr Ala Ala Ser Ser Ser Ser Leu Glu Lys Ser
            20                  25                  30

<210> SEQ ID NO 109
<211> LENGTH: 12
<212> TYPE: PRT
<213> ORGANISM: Artificial Sequence
<220> FEATURE:
<223> OTHER INFORMATION: peptide fragment of beta actin

<400> SEQUENCE: 109

Arg Gly Tyr Ser Phe Thr Thr Thr Ala Glu Arg Glu
1               5                   10

<210> SEQ ID NO 110
<211> LENGTH: 24
<212> TYPE: PRT
<213> ORGANISM: Artificial Sequence
<220> FEATURE:

```
<223> OTHER INFORMATION: peptide fragment of beta actin

<400> SEQUENCE: 110

Arg Lys Asp Leu Tyr Ala Asn Thr Val Leu Ser Gly Gly Thr Thr Met
1               5                   10                  15

Tyr Pro Gly Ile Ala Asp Arg Met
            20

<210> SEQ ID NO 111
<211> LENGTH: 32
<212> TYPE: PRT
<213> ORGANISM: Artificial Sequence
<220> FEATURE:
<223> OTHER INFORMATION: peptide fragment of beta actin

<400> SEQUENCE: 111

Arg Thr Thr Gly Ile Val Met Asp Ser Gly Asp Gly Val Thr His Thr
1               5                   10                  15

Val Pro Ile Tyr Glu Gly Tyr Ala Leu Pro His Ala Ile Leu Arg Leu
            20                  25                  30

<210> SEQ ID NO 112
<211> LENGTH: 20
<212> TYPE: PRT
<213> ORGANISM: Artificial Sequence
<220> FEATURE:
<223> OTHER INFORMATION: peptide fragment of beta actin

<400> SEQUENCE: 112

Arg Val Ala Pro Glu Glu His Pro Val Leu Leu Thr Glu Ala Pro Leu
1               5                   10                  15

Asn Pro Lys Ala
            20

<210> SEQ ID NO 113
<211> LENGTH: 12
<212> TYPE: PRT
<213> ORGANISM: Artificial Sequence
<220> FEATURE:
<223> OTHER INFORMATION: peptide fragment of vimentin

<400> SEQUENCE: 113

Lys Phe Ala Asp Leu Ser Glu Ala Ala Asn Arg Asn
1               5                   10

<210> SEQ ID NO 114
<211> LENGTH: 12
<212> TYPE: PRT
<213> ORGANISM: Artificial Sequence
<220> FEATURE:
<223> OTHER INFORMATION: peptide fragment of vimentin

<400> SEQUENCE: 114

Lys Ile Leu Leu Ala Glu Leu Glu Gln Leu Lys Gly
1               5                   10

<210> SEQ ID NO 115
<211> LENGTH: 16
<212> TYPE: PRT
<213> ORGANISM: Artificial Sequence
<220> FEATURE:
<223> OTHER INFORMATION: peptide fragment of vimentin

<400> SEQUENCE: 115

Lys Ile Leu Leu Ala Glu Leu Glu Gln Leu Lys Gly Gln Gly Lys Ser
```

```
<210> SEQ ID NO 116
<211> LENGTH: 10
<212> TYPE: PRT
<213> ORGANISM: Artificial Sequence
<220> FEATURE:
<223> OTHER INFORMATION: peptide fragment of vimentin

<400> SEQUENCE: 116

Lys Leu Gln Glu Glu Met Leu Gln Arg Glu
1               5                   10

<210> SEQ ID NO 117
<211> LENGTH: 21
<212> TYPE: PRT
<213> ORGANISM: Artificial Sequence
<220> FEATURE:
<223> OTHER INFORMATION: peptide fragment of vimentin

<400> SEQUENCE: 117

Lys Leu Gln Glu Glu Met Leu Gln Arg Glu Glu Ala Glu Asn Thr Leu
1               5                   10                  15

Gln Ser Phe Arg Gln
            20

<210> SEQ ID NO 118
<211> LENGTH: 11
<212> TYPE: PRT
<213> ORGANISM: Artificial Sequence
<220> FEATURE:
<223> OTHER INFORMATION: peptide fragment of vimentin

<400> SEQUENCE: 118

Lys Val Glu Leu Gln Glu Leu Asn Asp Arg Phe
1               5                   10

<210> SEQ ID NO 119
<211> LENGTH: 17
<212> TYPE: PRT
<213> ORGANISM: Artificial Sequence
<220> FEATURE:
<223> OTHER INFORMATION: peptide fragment of vimentin

<400> SEQUENCE: 119

Arg Asp Gly Gln Val Ile Asn Glu Thr Ser Gln His His Asp Asp Leu
1               5                   10                  15

Glu

<210> SEQ ID NO 120
<211> LENGTH: 11
<212> TYPE: PRT
<213> ORGANISM: Artificial Sequence
<220> FEATURE:
<223> OTHER INFORMATION: peptide fragment of vimentin

<400> SEQUENCE: 120

Arg Asp Asn Leu Ala Glu Asp Ile Met Arg Leu
1               5                   10

<210> SEQ ID NO 121
<211> LENGTH: 12
<212> TYPE: PRT
<213> ORGANISM: Artificial Sequence
<220> FEATURE:
<223> OTHER INFORMATION: peptide fragment of vimentin
```

<400> SEQUENCE: 121

Arg Glu Lys Leu Gln Glu Glu Met Leu Gln Arg Glu
1               5                   10

<210> SEQ ID NO 122
<211> LENGTH: 23
<212> TYPE: PRT
<213> ORGANISM: Artificial Sequence
<220> FEATURE:
<223> OTHER INFORMATION: peptide fragment of vimentin

<400> SEQUENCE: 122

Arg Glu Lys Leu Gln Glu Glu Met Leu Gln Arg Glu Glu Ala Glu Asn
1               5                   10                  15

Thr Leu Gln Ser Phe Arg Gln
            20

<210> SEQ ID NO 123
<211> LENGTH: 21
<212> TYPE: PRT
<213> ORGANISM: Artificial Sequence
<220> FEATURE:
<223> OTHER INFORMATION: peptide fragment of vimentin

<400> SEQUENCE: 123

Arg Glu Met Glu Glu Asn Phe Ala Val Glu Ala Ala Asn Tyr Gln Asp
1               5                   10                  15

Thr Ile Gly Arg Leu
            20

<210> SEQ ID NO 124
<211> LENGTH: 17
<212> TYPE: PRT
<213> ORGANISM: Artificial Sequence
<220> FEATURE:
<223> OTHER INFORMATION: peptide fragment of vimentin

<400> SEQUENCE: 124

Arg Glu Thr Asn Leu Asp Ser Leu Pro Leu Val Asp Thr His Ser Lys
1               5                   10                  15

Arg

<210> SEQ ID NO 125
<211> LENGTH: 9
<212> TYPE: PRT
<213> ORGANISM: Artificial Sequence
<220> FEATURE:
<223> OTHER INFORMATION: peptide fragment of vimentin

<400> SEQUENCE: 125

Arg Phe Ala Asn Tyr Ile Asp Lys Val
1               5

<210> SEQ ID NO 126
<211> LENGTH: 16
<212> TYPE: PRT
<213> ORGANISM: Artificial Sequence
<220> FEATURE:
<223> OTHER INFORMATION: peptide fragment of vimentin

<400> SEQUENCE: 126

Arg Ile Ser Leu Pro Leu Pro Asn Phe Ser Ser Leu Asn Leu Arg Glu
1               5                   10                  15

<210> SEQ ID NO 127
<211> LENGTH: 15
<212> TYPE: PRT
<213> ORGANISM: Artificial Sequence
<220> FEATURE:
<223> OTHER INFORMATION: peptide fragment of vimentin

<400> SEQUENCE: 127

Arg Lys Val Glu Ser Leu Gln Glu Glu Ile Ala Phe Leu Lys Lys
1               5                   10                  15

<210> SEQ ID NO 128
<211> LENGTH: 16
<212> TYPE: PRT
<213> ORGANISM: Artificial Sequence
<220> FEATURE:
<223> OTHER INFORMATION: peptide fragment of vimentin

<400> SEQUENCE: 128

Arg Lys Val Glu Ser Leu Gln Glu Glu Ile Ala Phe Leu Lys Lys Leu
1               5                   10                  15

<210> SEQ ID NO 129
<211> LENGTH: 12
<212> TYPE: PRT
<213> ORGANISM: Artificial Sequence
<220> FEATURE:
<223> OTHER INFORMATION: peptide fragment of vimentin

<400> SEQUENCE: 129

Arg Leu Gly Asp Leu Tyr Glu Glu Glu Met Arg Glu
1               5                   10

<210> SEQ ID NO 130
<211> LENGTH: 21
<212> TYPE: PRT
<213> ORGANISM: Artificial Sequence
<220> FEATURE:
<223> OTHER INFORMATION: peptide fragment of vimentin

<400> SEQUENCE: 130

Arg Leu Leu Gln Asp Ser Val Asp Phe Ser Leu Ala Asp Ala Ile Asn
1               5                   10                  15

Thr Glu Phe Lys Asn
            20

<210> SEQ ID NO 131
<211> LENGTH: 11
<212> TYPE: PRT
<213> ORGANISM: Artificial Sequence
<220> FEATURE:
<223> OTHER INFORMATION: peptide fragment of vimentin

<400> SEQUENCE: 131

Arg Leu Gln Asp Glu Ile Gln Asn Met Lys Glu
1               5                   10

<210> SEQ ID NO 132
<211> LENGTH: 16
<212> TYPE: PRT
<213> ORGANISM: Artificial Sequence
<220> FEATURE:
<223> OTHER INFORMATION: peptide fragment of vimentin

<400> SEQUENCE: 132

Arg Leu Gln Asp Glu Ile Gln Asn Met Lys Glu Glu Met Ala Arg His
1               5                   10                  15

```
1               5                  10                  15
```

<210> SEQ ID NO 133
<211> LENGTH: 11
<212> TYPE: PRT
<213> ORGANISM: Artificial Sequence
<220> FEATURE:
<223> OTHER INFORMATION: peptide fragment of vimentin

<400> SEQUENCE: 133

```
Arg Gln Val Asp Gln Leu Thr Asn Asp Lys Ala
1               5                  10
```

<210> SEQ ID NO 134
<211> LENGTH: 12
<212> TYPE: PRT
<213> ORGANISM: Artificial Sequence
<220> FEATURE:
<223> OTHER INFORMATION: peptide fragment of vimentin

<400> SEQUENCE: 134

```
Arg Arg Gln Val Asp Gln Leu Thr Asn Asp Lys Ala
1               5                  10
```

<210> SEQ ID NO 135
<211> LENGTH: 16
<212> TYPE: PRT
<213> ORGANISM: Artificial Sequence
<220> FEATURE:
<223> OTHER INFORMATION: peptide fragment of vimentin

<400> SEQUENCE: 135

```
Arg Ser Leu Tyr Ala Ser Ser Pro Gly Gly Val Tyr Ala Thr Arg Ser
1               5                  10                  15
```

<210> SEQ ID NO 136
<211> LENGTH: 15
<212> TYPE: PRT
<213> ORGANISM: Artificial Sequence
<220> FEATURE:
<223> OTHER INFORMATION: peptide fragment of vimentin

<400> SEQUENCE: 136

```
Arg Thr Asn Glu Lys Val Glu Leu Gln Glu Leu Asn Asp Arg Phe
1               5                  10                  15
```

<210> SEQ ID NO 137
<211> LENGTH: 16
<212> TYPE: PRT
<213> ORGANISM: Artificial Sequence
<220> FEATURE:
<223> OTHER INFORMATION: peptide fragment of vimentin

<400> SEQUENCE: 137

```
Arg Thr Tyr Ser Leu Gly Ser Ala Leu Arg Pro Ser Thr Ser Arg Ser
1               5                  10                  15
```

<210> SEQ ID NO 138
<211> LENGTH: 16
<212> TYPE: PRT
<213> ORGANISM: Artificial Sequence
<220> FEATURE:
<223> OTHER INFORMATION: peptide fragment of vimentin

<400> SEQUENCE: 138

```
Arg Val Glu Val Glu Arg Asp Asn Leu Ala Glu Asp Ile Met Arg Leu
1               5                  10                  15
```

<210> SEQ ID NO 139
<211> LENGTH: 23
<212> TYPE: PRT
<213> ORGANISM: Artificial Sequence
<220> FEATURE:
<223> OTHER INFORMATION: peptide fragment of protein disulfide isomerase
      family A, member 3

<400> SEQUENCE: 139

Lys Asp Ala Ser Ile Val Gly Phe Phe Asp Asp Ser Phe Ser Glu Ala
1               5                   10                  15

His Ser Glu Phe Leu Lys Ala
            20

<210> SEQ ID NO 140
<211> LENGTH: 15
<212> TYPE: PRT
<213> ORGANISM: Artificial Sequence
<220> FEATURE:
<223> OTHER INFORMATION: peptide fragment of protein disulfide isomerase
      family A, member 3

<400> SEQUENCE: 140

Lys Asp Leu Leu Ile Ala Tyr Tyr Asp Val Asp Tyr Glu Lys Asn
1               5                   10                  15

<210> SEQ ID NO 141
<211> LENGTH: 10
<212> TYPE: PRT
<213> ORGANISM: Artificial Sequence
<220> FEATURE:
<223> OTHER INFORMATION: peptide fragment of protein disulfide isomerase
      family A, member 3

<400> SEQUENCE: 141

Lys Asp Pro Asn Ile Val Ile Ala Lys Met
1               5                   10

<210> SEQ ID NO 142
<211> LENGTH: 14
<212> TYPE: PRT
<213> ORGANISM: Artificial Sequence
<220> FEATURE:
<223> OTHER INFORMATION: peptide fragment of protein disulfide isomerase
      family A, member 3

<400> SEQUENCE: 142

Lys Phe Glu Asp Lys Thr Val Ala Tyr Thr Glu Gln Lys Met
1               5                   10

<210> SEQ ID NO 143
<211> LENGTH: 11
<212> TYPE: PRT
<213> ORGANISM: Artificial Sequence
<220> FEATURE:
<223> OTHER INFORMATION: peptide fragment of protein disulfide isomerase
      family A, member 3

<400> SEQUENCE: 143

Lys Phe Val Met Gln Glu Glu Phe Ser Arg Asp
1               5                   10

<210> SEQ ID NO 144
<211> LENGTH: 8
<212> TYPE: PRT
<213> ORGANISM: Artificial Sequence

```
<220> FEATURE:
<223> OTHER INFORMATION: peptide fragment of protein disulfide isomerase
      family A, member 3

<400> SEQUENCE: 144

Lys Gly Ser Asn Tyr Trp Arg Asn
1               5

<210> SEQ ID NO 145
<211> LENGTH: 17
<212> TYPE: PRT
<213> ORGANISM: Artificial Sequence
<220> FEATURE:
<223> OTHER INFORMATION: peptide fragment of protein disulfide isomerase
      family A, member 3

<400> SEQUENCE: 145

Lys Ile Phe Arg Asp Gly Glu Glu Ala Gly Ala Tyr Asp Gly Pro Arg
1               5                   10                  15

Thr

<210> SEQ ID NO 146
<211> LENGTH: 10
<212> TYPE: PRT
<213> ORGANISM: Artificial Sequence
<220> FEATURE:
<223> OTHER INFORMATION: peptide fragment of protein disulfide isomerase
      family A, member 3

<400> SEQUENCE: 146

Lys Leu Asn Phe Ala Val Ala Ser Arg Lys
1               5                   10

<210> SEQ ID NO 147
<211> LENGTH: 13
<212> TYPE: PRT
<213> ORGANISM: Artificial Sequence
<220> FEATURE:
<223> OTHER INFORMATION: peptide fragment of protein disulfide isomerase
      family A, member 3

<400> SEQUENCE: 147

Lys Leu Ser Lys Asp Pro Asn Ile Val Ile Ala Lys Met
1               5                   10

<210> SEQ ID NO 148
<211> LENGTH: 17
<212> TYPE: PRT
<213> ORGANISM: Artificial Sequence
<220> FEATURE:
<223> OTHER INFORMATION: peptide fragment of protein disulfide isomerase
      family A, member 3

<400> SEQUENCE: 148

Lys Met Asp Ala Thr Ala Asn Asp Val Pro Ser Pro Tyr Glu Val Arg
1               5                   10                  15

Gly

<210> SEQ ID NO 149
<211> LENGTH: 12
<212> TYPE: PRT
<213> ORGANISM: Artificial Sequence
<220> FEATURE:
<223> OTHER INFORMATION: peptide fragment of protein disulfide isomerase
      family A, member 3

<400> SEQUENCE: 149
```

-continued

```
Lys Gln Ala Gly Pro Ala Ser Val Pro Leu Arg Thr
1               5                   10

<210> SEQ ID NO 150
<211> LENGTH: 14
<212> TYPE: PRT
<213> ORGANISM: Artificial Sequence
<220> FEATURE:
<223> OTHER INFORMATION: peptide fragment of protein disulfide isomerase
      family A, member 3

<400> SEQUENCE: 150

Lys Arg Leu Ala Pro Glu Tyr Glu Ala Ala Ala Thr Arg Leu
1               5                   10

<210> SEQ ID NO 151
<211> LENGTH: 15
<212> TYPE: PRT
<213> ORGANISM: Artificial Sequence
<220> FEATURE:
<223> OTHER INFORMATION: peptide fragment of protein disulfide isomerase
      family A, member 3

<400> SEQUENCE: 151

Lys Ser Glu Pro Ile Pro Glu Ser Asn Asp Gly Pro Val Lys Val
1               5                   10                  15

<210> SEQ ID NO 152
<211> LENGTH: 26
<212> TYPE: PRT
<213> ORGANISM: Artificial Sequence
<220> FEATURE:
<223> OTHER INFORMATION: peptide fragment of protein disulfide isomerase
      family A, member 3

<400> SEQUENCE: 152

Lys Thr Phe Ser His Glu Leu Ser Asp Phe Gly Leu Glu Ser Thr Ala
1               5                   10                  15

Gly Glu Ile Pro Val Val Ala Ile Arg Thr
            20                  25

<210> SEQ ID NO 153
<211> LENGTH: 10
<212> TYPE: PRT
<213> ORGANISM: Artificial Sequence
<220> FEATURE:
<223> OTHER INFORMATION: peptide fragment of protein disulfide isomerase
      family A, member 3

<400> SEQUENCE: 153

Lys Thr Val Ala Tyr Thr Glu Gln Lys Met
1               5                   10

<210> SEQ ID NO 154
<211> LENGTH: 12
<212> TYPE: PRT
<213> ORGANISM: Artificial Sequence
<220> FEATURE:
<223> OTHER INFORMATION: peptide fragment of protein disulfide isomerase
      family A, member 3

<400> SEQUENCE: 154

Lys Tyr Gly Val Ser Gly Tyr Pro Thr Leu Lys Ile
1               5                   10

<210> SEQ ID NO 155
```

-continued

```
<211> LENGTH: 14
<212> TYPE: PRT
<213> ORGANISM: Artificial Sequence
<220> FEATURE:
<223> OTHER INFORMATION: peptide fragment of protein disulfide isomerase
      family A, member 3

<400> SEQUENCE: 155

Arg Asp Gly Glu Glu Ala Gly Ala Tyr Asp Gly Pro Arg Thr
1               5                   10

<210> SEQ ID NO 156
<211> LENGTH: 16
<212> TYPE: PRT
<213> ORGANISM: Artificial Sequence
<220> FEATURE:
<223> OTHER INFORMATION: peptide fragment of protein disulfide isomerase
      family A, member 3

<400> SEQUENCE: 156

Arg Glu Ala Thr Asn Pro Pro Val Ile Gln Glu Glu Lys Pro Lys Lys
1               5                   10                  15

<210> SEQ ID NO 157
<211> LENGTH: 13
<212> TYPE: PRT
<213> ORGANISM: Artificial Sequence
<220> FEATURE:
<223> OTHER INFORMATION: peptide fragment of protein disulfide isomerase
      family A, member 3

<400> SEQUENCE: 157

Arg Glu Leu Ser Asp Phe Ile Ser Tyr Leu Gln Arg Glu
1               5                   10

<210> SEQ ID NO 158
<211> LENGTH: 13
<212> TYPE: PRT
<213> ORGANISM: Artificial Sequence
<220> FEATURE:
<223> OTHER INFORMATION: peptide fragment of protein disulfide isomerase
      family A, member 3

<400> SEQUENCE: 158

Arg Phe Leu Gln Asp Tyr Phe Asp Gly Asn Leu Lys Arg
1               5                   10

<210> SEQ ID NO 159
<211> LENGTH: 14
<212> TYPE: PRT
<213> ORGANISM: Artificial Sequence
<220> FEATURE:
<223> OTHER INFORMATION: peptide fragment of protein disulfide isomerase
      family A, member 3

<400> SEQUENCE: 159

Arg Phe Leu Gln Asp Tyr Phe Asp Gly Asn Leu Lys Arg Tyr
1               5                   10

<210> SEQ ID NO 160
<211> LENGTH: 14
<212> TYPE: PRT
<213> ORGANISM: Artificial Sequence
<220> FEATURE:
<223> OTHER INFORMATION: peptide fragment of protein disulfide isomerase
      family A, member 3

<400> SEQUENCE: 160
```

Arg Gly Phe Pro Thr Ile Tyr Phe Ser Pro Ala Asn Lys Lys
1               5                   10

<210> SEQ ID NO 161
<211> LENGTH: 27
<212> TYPE: PRT
<213> ORGANISM: Artificial Sequence
<220> FEATURE:
<223> OTHER INFORMATION: peptide fragment of protein disulfide isomerase
      family A, member 3

<400> SEQUENCE: 161

Arg Lys Thr Phe Ser His Glu Leu Ser Asp Phe Gly Leu Glu Ser Thr
1               5                   10                  15

Ala Gly Glu Ile Pro Val Val Ala Ile Arg Thr
            20                  25

<210> SEQ ID NO 162
<211> LENGTH: 13
<212> TYPE: PRT
<213> ORGANISM: Artificial Sequence
<220> FEATURE:
<223> OTHER INFORMATION: peptide fragment of protein disulfide isomerase
      family A, member 3

<400> SEQUENCE: 162

Arg Leu Ala Pro Glu Tyr Glu Ala Ala Ala Thr Arg Leu
1               5                   10

<210> SEQ ID NO 163
<211> LENGTH: 12
<212> TYPE: PRT
<213> ORGANISM: Artificial Sequence
<220> FEATURE:
<223> OTHER INFORMATION: peptide fragment of protein disulfide isomerase
      family A, member 3

<400> SEQUENCE: 163

Arg Thr Ala Asp Gly Ile Val Ser His Leu Lys Lys
1               5                   10

<210> SEQ ID NO 164
<211> LENGTH: 13
<212> TYPE: PRT
<213> ORGANISM: Artificial Sequence
<220> FEATURE:
<223> OTHER INFORMATION: peptide fragment of protein disulfide isomerase
      family A, member 3

<400> SEQUENCE: 164

Arg Thr Ala Asp Gly Ile Val Ser His Leu Lys Lys Gln
1               5                   10

<210> SEQ ID NO 165
<211> LENGTH: 22
<212> TYPE: PRT
<213> ORGANISM: Artificial Sequence
<220> FEATURE:
<223> OTHER INFORMATION: peptide fragment of alpha enolase 1

<400> SEQUENCE: 165

Lys Ala Gly Tyr Thr Asp Lys Val Val Ile Gly Met Asp Val Ala Ala
1               5                   10                  15

Ser Glu Phe Phe Arg Ser
            20

```
<210> SEQ ID NO 166
<211> LENGTH: 21
<212> TYPE: PRT
<213> ORGANISM: Artificial Sequence
<220> FEATURE:
<223> OTHER INFORMATION: peptide fragment of alpha enolase 1

<400> SEQUENCE: 166

Lys Asp Ala Thr Asn Val Gly Asp Glu Gly Gly Phe Ala Pro Asn Ile
1               5                   10                  15

Leu Glu Asn Lys Glu
            20

<210> SEQ ID NO 167
<211> LENGTH: 28
<212> TYPE: PRT
<213> ORGANISM: Artificial Sequence
<220> FEATURE:
<223> OTHER INFORMATION: peptide fragment of alpha enolase 1

<400> SEQUENCE: 167

Lys Asp Ala Thr Asn Val Gly Asp Glu Gly Gly Phe Ala Pro Asn Ile
1               5                   10                  15

Leu Glu Asn Lys Glu Gly Leu Glu Leu Leu Lys Thr
            20                  25

<210> SEQ ID NO 168
<211> LENGTH: 23
<212> TYPE: PRT
<213> ORGANISM: Artificial Sequence
<220> FEATURE:
<223> OTHER INFORMATION: peptide fragment of alpha enolase 1

<400> SEQUENCE: 168

Lys Asp Tyr Pro Val Val Ser Ile Glu Asp Pro Phe Asp Gln Asp Asp
1               5                   10                  15

Trp Gly Ala Trp Gln Lys Phe
            20

<210> SEQ ID NO 169
<211> LENGTH: 22
<212> TYPE: PRT
<213> ORGANISM: Artificial Sequence
<220> FEATURE:
<223> OTHER INFORMATION: peptide fragment of alpha enolase 1

<400> SEQUENCE: 169

Lys Phe Thr Ala Ser Ala Gly Ile Gln Val Val Gly Asp Asp Leu Thr
1               5                   10                  15

Val Thr Asn Pro Lys Arg
            20

<210> SEQ ID NO 170
<211> LENGTH: 19
<212> TYPE: PRT
<213> ORGANISM: Artificial Sequence
<220> FEATURE:
<223> OTHER INFORMATION: peptide fragment of alpha enolase 1

<400> SEQUENCE: 170

Lys Leu Ala Met Gln Glu Phe Met Ile Leu Pro Val Gly Ala Ala Asn
1               5                   10                  15

Phe Arg Glu
```

```
<210> SEQ ID NO 171
<211> LENGTH: 16
<212> TYPE: PRT
<213> ORGANISM: Artificial Sequence
<220> FEATURE:
<223> OTHER INFORMATION: peptide fragment of alpha enolase 1

<400> SEQUENCE: 171

Lys Leu Ala Gln Ala Asn Gly Trp Gly Val Met Val Ser His Arg Ser
1               5                   10                  15

<210> SEQ ID NO 172
<211> LENGTH: 27
<212> TYPE: PRT
<213> ORGANISM: Artificial Sequence
<220> FEATURE:
<223> OTHER INFORMATION: peptide fragment of alpha enolase 1

<400> SEQUENCE: 172

Lys Ser Phe Ile Lys Asp Tyr Pro Val Val Ser Ile Glu Asp Pro Phe
1               5                   10                  15

Asp Gln Asp Asp Trp Gly Ala Trp Gln Lys Phe
            20                  25

<210> SEQ ID NO 173
<211> LENGTH: 11
<212> TYPE: PRT
<213> ORGANISM: Artificial Sequence
<220> FEATURE:
<223> OTHER INFORMATION: peptide fragment of alpha enolase 1

<400> SEQUENCE: 173

Lys Thr Ile Ala Pro Ala Leu Val Ser Lys Lys
1               5                   10

<210> SEQ ID NO 174
<211> LENGTH: 16
<212> TYPE: PRT
<213> ORGANISM: Artificial Sequence
<220> FEATURE:
<223> OTHER INFORMATION: peptide fragment of alpha enolase 1

<400> SEQUENCE: 174

Lys Val Val Ile Gly Met Asp Val Ala Ala Ser Glu Phe Phe Arg Ser
1               5                   10                  15

<210> SEQ ID NO 175
<211> LENGTH: 15
<212> TYPE: PRT
<213> ORGANISM: Artificial Sequence
<220> FEATURE:
<223> OTHER INFORMATION: peptide fragment of alpha enolase 1

<400> SEQUENCE: 175

Arg Gly Asn Pro Thr Val Glu Val Asp Leu Phe Thr Ser Lys Gly
1               5                   10                  15

<210> SEQ ID NO 176
<211> LENGTH: 32
<212> TYPE: PRT
<213> ORGANISM: Artificial Sequence
<220> FEATURE:
<223> OTHER INFORMATION: peptide fragment of alpha enolase 1

<400> SEQUENCE: 176

Arg His Ile Ala Asp Leu Ala Gly Asn Ser Glu Val Ile Leu Pro Val
1               5                   10                  15
```

Pro Ala Phe Asn Val Ile Asn Gly Gly Ser His Ala Gly Asn Lys Leu
            20                  25                  30

<210> SEQ ID NO 177
<211> LENGTH: 10
<212> TYPE: PRT
<213> ORGANISM: Artificial Sequence
<220> FEATURE:
<223> OTHER INFORMATION: peptide fragment of alpha enolase 1

<400> SEQUENCE: 177

Arg Ile Glu Glu Glu Leu Gly Ser Lys Ala
1               5                   10

<210> SEQ ID NO 178
<211> LENGTH: 12
<212> TYPE: PRT
<213> ORGANISM: Artificial Sequence
<220> FEATURE:
<223> OTHER INFORMATION: peptide fragment of alpha enolase 1

<400> SEQUENCE: 178

Arg Ile Gly Ala Glu Val Tyr His Asn Leu Lys Asn
1               5                   10

<210> SEQ ID NO 179
<211> LENGTH: 11
<212> TYPE: PRT
<213> ORGANISM: Artificial Sequence
<220> FEATURE:
<223> OTHER INFORMATION: peptide fragment of alpha enolase 1

<400> SEQUENCE: 179

Arg Ser Gly Lys Tyr Asp Leu Asp Phe Lys Ser
1               5                   10

<210> SEQ ID NO 180
<211> LENGTH: 18
<212> TYPE: PRT
<213> ORGANISM: Artificial Sequence
<220> FEATURE:
<223> OTHER INFORMATION: peptide fragment of alpha enolase 1

<400> SEQUENCE: 180

Arg Ser Gly Lys Tyr Asp Leu Asp Phe Lys Ser Pro Asp Asp Pro Ser
1               5                   10                  15

Arg Tyr

<210> SEQ ID NO 181
<211> LENGTH: 14
<212> TYPE: PRT
<213> ORGANISM: Artificial Sequence
<220> FEATURE:
<223> OTHER INFORMATION: peptide fragment of alpha enolase 1

<400> SEQUENCE: 181

Arg Tyr Ile Ser Pro Asp Gln Leu Ala Asp Leu Tyr Lys Ser
1               5                   10

<210> SEQ ID NO 182
<211> LENGTH: 21
<212> TYPE: PRT
<213> ORGANISM: Artificial Sequence
<220> FEATURE:
<223> OTHER INFORMATION: peptide fragment of FK506 binding protein 4

```
<400> SEQUENCE: 182

Lys Ala Glu Ala Ser Ser Gly Asp His Pro Thr Asp Thr Glu Met Lys
1               5                   10                  15

Glu Glu Gln Lys Ser
            20

<210> SEQ ID NO 183
<211> LENGTH: 23
<212> TYPE: PRT
<213> ORGANISM: Artificial Sequence
<220> FEATURE:
<223> OTHER INFORMATION: peptide fragment of FK506 binding protein 4

<400> SEQUENCE: 183

Lys Ala Thr Glu Ser Gly Ala Gln Ser Ala Pro Leu Pro Met Glu Gly
1               5                   10                  15

Val Asp Ile Ser Pro Lys Gln
            20

<210> SEQ ID NO 184
<211> LENGTH: 12
<212> TYPE: PRT
<213> ORGANISM: Artificial Sequence
<220> FEATURE:
<223> OTHER INFORMATION: peptide fragment of FK506 binding protein 4

<400> SEQUENCE: 184

Lys Ala Trp Asp Ile Ala Ile Ala Thr Met Lys Val
1               5                   10

<210> SEQ ID NO 185
<211> LENGTH: 16
<212> TYPE: PRT
<213> ORGANISM: Artificial Sequence
<220> FEATURE:
<223> OTHER INFORMATION: peptide fragment of FK506 binding protein 4

<400> SEQUENCE: 185

Lys Asp Lys Phe Ser Phe Asp Leu Gly Lys Gly Glu Val Ile Lys Ala
1               5                   10                  15

<210> SEQ ID NO 186
<211> LENGTH: 12
<212> TYPE: PRT
<213> ORGANISM: Artificial Sequence
<220> FEATURE:
<223> OTHER INFORMATION: peptide fragment of FK506 binding protein 4

<400> SEQUENCE: 186

Lys Glu Ser Trp Glu Met Asn Ser Glu Glu Lys Leu
1               5                   10

<210> SEQ ID NO 187
<211> LENGTH: 9
<212> TYPE: PRT
<213> ORGANISM: Artificial Sequence
<220> FEATURE:
<223> OTHER INFORMATION: peptide fragment of FK506 binding protein 4

<400> SEQUENCE: 187

Lys Phe Asp Ser Ser Leu Asp Arg Lys
1               5

<210> SEQ ID NO 188
<211> LENGTH: 10
```

```
<212> TYPE: PRT
<213> ORGANISM: Artificial Sequence
<220> FEATURE:
<223> OTHER INFORMATION: peptide fragment of FK506 binding protein 4

<400> SEQUENCE: 188

Lys Phe Asp Ser Ser Leu Asp Arg Lys Asp
1               5                   10

<210> SEQ ID NO 189
<211> LENGTH: 16
<212> TYPE: PRT
<213> ORGANISM: Artificial Sequence
<220> FEATURE:
<223> OTHER INFORMATION: peptide fragment of FK506 binding protein 4

<400> SEQUENCE: 189

Lys Gly Glu Asp Leu Thr Glu Glu Glu Asp Gly Gly Ile Ile Arg Arg
1               5                   10                  15

<210> SEQ ID NO 190
<211> LENGTH: 21
<212> TYPE: PRT
<213> ORGANISM: Artificial Sequence
<220> FEATURE:
<223> OTHER INFORMATION: peptide fragment of FK506 binding protein 4

<400> SEQUENCE: 190

Lys Gly Glu His Ser Ile Val Tyr Leu Lys Pro Ser Tyr Ala Phe Gly
1               5                   10                  15

Ser Val Gly Lys Glu
            20

<210> SEQ ID NO 191
<211> LENGTH: 20
<212> TYPE: PRT
<213> ORGANISM: Artificial Sequence
<220> FEATURE:
<223> OTHER INFORMATION: peptide fragment of FK506 binding protein 4

<400> SEQUENCE: 191

Lys Ile Val Ser Trp Leu Glu Tyr Glu Ser Ser Phe Ser Asn Glu Glu
1               5                   10                  15

Ala Gln Lys Ala
            20

<210> SEQ ID NO 192
<211> LENGTH: 21
<212> TYPE: PRT
<213> ORGANISM: Artificial Sequence
<220> FEATURE:
<223> OTHER INFORMATION: peptide fragment of FK506 binding protein 4

<400> SEQUENCE: 192

Lys Lys Ile Val Ser Trp Leu Glu Tyr Glu Ser Ser Phe Ser Asn Glu
1               5                   10                  15

Glu Ala Gln Lys Ala
            20

<210> SEQ ID NO 193
<211> LENGTH: 10
<212> TYPE: PRT
<213> ORGANISM: Artificial Sequence
<220> FEATURE:
<223> OTHER INFORMATION: peptide fragment of FK506 binding protein 4
```

<400> SEQUENCE: 193

Lys Leu Glu Gln Ser Thr Ile Val Lys Glu
1               5                   10

<210> SEQ ID NO 194
<211> LENGTH: 10
<212> TYPE: PRT
<213> ORGANISM: Artificial Sequence
<220> FEATURE:
<223> OTHER INFORMATION: peptide fragment of FK506 binding protein 4

<400> SEQUENCE: 194

Lys Leu Tyr Ala Asn Met Phe Glu Arg Leu
1               5                   10

<210> SEQ ID NO 195
<211> LENGTH: 11
<212> TYPE: PRT
<213> ORGANISM: Artificial Sequence
<220> FEATURE:
<223> OTHER INFORMATION: peptide fragment of FK506 binding protein 4

<400> SEQUENCE: 195

Lys Val Leu Gln Leu Tyr Pro Asn Asn Lys Ala
1               5                   10

<210> SEQ ID NO 196
<211> LENGTH: 15
<212> TYPE: PRT
<213> ORGANISM: Artificial Sequence
<220> FEATURE:
<223> OTHER INFORMATION: peptide fragment of FK506 binding protein 4

<400> SEQUENCE: 196

Arg Glu Gly Thr Gly Thr Glu Met Pro Met Ile Gly Asp Arg Val
1               5                   10                  15

<210> SEQ ID NO 197
<211> LENGTH: 19
<212> TYPE: PRT
<213> ORGANISM: Artificial Sequence
<220> FEATURE:
<223> OTHER INFORMATION: peptide fragment of FK506 binding protein 4

<400> SEQUENCE: 197

Arg Phe Glu Ile Gly Glu Gly Glu Asn Leu Asp Leu Pro Tyr Gly Leu
1               5                   10                  15

Glu Arg Ala

<210> SEQ ID NO 198
<211> LENGTH: 16
<212> TYPE: PRT
<213> ORGANISM: Artificial Sequence
<220> FEATURE:
<223> OTHER INFORMATION: peptide fragment of FK506 binding protein 4

<400> SEQUENCE: 198

Arg Gly Glu Ala His Leu Ala Val Asn Asp Phe Glu Leu Ala Arg Ala
1               5                   10                  15

<210> SEQ ID NO 199
<211> LENGTH: 24
<212> TYPE: PRT
<213> ORGANISM: Artificial Sequence
<220> FEATURE:
<223> OTHER INFORMATION: peptide fragment of FK506 binding protein 4

-continued

<400> SEQUENCE: 199

Arg Gly Glu Gly Tyr Ala Lys Pro Asn Glu Gly Ala Ile Val Glu Val
1               5                   10                  15

Ala Leu Glu Gly Tyr Tyr Lys Asp
            20

<210> SEQ ID NO 200
<211> LENGTH: 26
<212> TYPE: PRT
<213> ORGANISM: Artificial Sequence
<220> FEATURE:
<223> OTHER INFORMATION: peptide fragment of FK506 binding protein 4

<400> SEQUENCE: 200

Arg Gly Glu Gly Tyr Ala Lys Pro Asn Glu Gly Ala Ile Val Glu Val
1               5                   10                  15

Ala Leu Glu Gly Tyr Tyr Lys Asp Lys Leu
            20                  25

<210> SEQ ID NO 201
<211> LENGTH: 17
<212> TYPE: PRT
<213> ORGANISM: Artificial Sequence
<220> FEATURE:
<223> OTHER INFORMATION: peptide fragment of FK506 binding protein 4

<400> SEQUENCE: 201

Arg Arg Gly Glu Ala His Leu Ala Val Asn Asp Phe Glu Leu Ala Arg
1               5                   10                  15

Ala

<210> SEQ ID NO 202
<211> LENGTH: 16
<212> TYPE: PRT
<213> ORGANISM: Artificial Sequence
<220> FEATURE:
<223> OTHER INFORMATION: peptide fragment of FK506 binding protein 4

<400> SEQUENCE: 202

Arg Val Phe Val His Tyr Thr Gly Trp Leu Leu Asp Gly Thr Lys Phe
1               5                   10                  15

<210> SEQ ID NO 203
<211> LENGTH: 12
<212> TYPE: PRT
<213> ORGANISM: Artificial Sequence
<220> FEATURE:
<223> OTHER INFORMATION: peptide fragment of glucose-6-phosphate
      dehydrogenase

<400> SEQUENCE: 203

Lys Glu Met Val Gln Asn Leu Met Val Leu Arg Phe
1               5                   10

<210> SEQ ID NO 204
<211> LENGTH: 12
<212> TYPE: PRT
<213> ORGANISM: Artificial Sequence
<220> FEATURE:
<223> OTHER INFORMATION: peptide fragment of glucose-6-phosphate
      dehydrogenase

<400> SEQUENCE: 204

Lys Gly Tyr Leu Asp Asp Pro Thr Val Pro Arg Gly

<210> SEQ ID NO 205
<211> LENGTH: 22
<212> TYPE: PRT
<213> ORGANISM: Artificial Sequence
<220> FEATURE:
<223> OTHER INFORMATION: peptide fragment of glucose-6-phosphate
      dehydrogenase

<400> SEQUENCE: 205

Lys Lys Pro Gly Met Phe Phe Asn Pro Glu Glu Ser Glu Leu Asp Leu
1               5                   10                  15

Thr Tyr Gly Asn Arg Tyr
            20

<210> SEQ ID NO 206
<211> LENGTH: 11
<212> TYPE: PRT
<213> ORGANISM: Artificial Sequence
<220> FEATURE:
<223> OTHER INFORMATION: peptide fragment of glucose-6-phosphate
      dehydrogenase

<400> SEQUENCE: 206

Lys Leu Lys Leu Glu Asp Phe Phe Ala Arg Asn
1               5                   10

<210> SEQ ID NO 207
<211> LENGTH: 9
<212> TYPE: PRT
<213> ORGANISM: Artificial Sequence
<220> FEATURE:
<223> OTHER INFORMATION: peptide fragment of glucose-6-phosphate
      dehydrogenase

<400> SEQUENCE: 207

Lys Leu Pro Asp Ala Tyr Glu Arg Leu
1               5

<210> SEQ ID NO 208
<211> LENGTH: 9
<212> TYPE: PRT
<213> ORGANISM: Artificial Sequence
<220> FEATURE:
<223> OTHER INFORMATION: peptide fragment of glucose-6-phosphate
      dehydrogenase

<400> SEQUENCE: 208

Lys Arg Asn Glu Leu Val Ile Arg Val
1               5

<210> SEQ ID NO 209
<211> LENGTH: 17
<212> TYPE: PRT
<213> ORGANISM: Artificial Sequence
<220> FEATURE:
<223> OTHER INFORMATION: peptide fragment of glucose-6-phosphate
      dehydrogenase

<400> SEQUENCE: 209

Arg Asp Gly Leu Leu Pro Glu Asn Thr Phe Ile Val Gly Tyr Ala Arg
1               5                   10                  15

Ser

<210> SEQ ID NO 210

```
<211> LENGTH: 30
<212> TYPE: PRT
<213> ORGANISM: Artificial Sequence
<220> FEATURE:
<223> OTHER INFORMATION: peptide fragment of glucose-6-phosphate
      dehydrogenase

<400> SEQUENCE: 210

Arg Glu Glu Leu Phe Gln Gly Asp Ala Phe His Gln Ser Asp Thr His
1               5                   10                  15

Ile Phe Ile Ile Met Gly Ala Ser Gly Asp Leu Ala Lys Lys
            20                  25                  30

<210> SEQ ID NO 211
<211> LENGTH: 13
<212> TYPE: PRT
<213> ORGANISM: Artificial Sequence
<220> FEATURE:
<223> OTHER INFORMATION: peptide fragment of glucose-6-phosphate
      dehydrogenase

<400> SEQUENCE: 211

Arg Gly Gly Tyr Phe Asp Glu Phe Gly Ile Ile Arg Gly
1               5                   10

<210> SEQ ID NO 212
<211> LENGTH: 12
<212> TYPE: PRT
<213> ORGANISM: Artificial Sequence
<220> FEATURE:
<223> OTHER INFORMATION: peptide fragment of glucose-6-phosphate
      dehydrogenase

<400> SEQUENCE: 212

Arg Gly Pro Thr Glu Ala Asp Glu Leu Met Lys Arg
1               5                   10

<210> SEQ ID NO 213
<211> LENGTH: 13
<212> TYPE: PRT
<213> ORGANISM: Artificial Sequence
<220> FEATURE:
<223> OTHER INFORMATION: peptide fragment of glucose-6-phosphate
      dehydrogenase

<400> SEQUENCE: 213

Arg Gly Pro Thr Glu Ala Asp Glu Leu Met Lys Arg Val
1               5                   10

<210> SEQ ID NO 214
<211> LENGTH: 20
<212> TYPE: PRT
<213> ORGANISM: Artificial Sequence
<220> FEATURE:
<223> OTHER INFORMATION: peptide fragment of glucose-6-phosphate
      dehydrogenase

<400> SEQUENCE: 214

Arg Gly Ser Thr Thr Ala Thr Phe Ala Ala Val Val Leu Tyr Val Glu
1               5                   10                  15

Asn Glu Arg Trp
            20

<210> SEQ ID NO 215
<211> LENGTH: 10
<212> TYPE: PRT
<213> ORGANISM: Artificial Sequence
```

```
<220> FEATURE:
<223> OTHER INFORMATION: peptide fragment of glucose-6-phosphate
      dehydrogenase

<400> SEQUENCE: 215

Arg Ile Phe Gly Pro Ile Trp Asn Arg Asp
1               5                   10

<210> SEQ ID NO 216
<211> LENGTH: 11
<212> TYPE: PRT
<213> ORGANISM: Artificial Sequence
<220> FEATURE:
<223> OTHER INFORMATION: peptide fragment of glucose-6-phosphate
      dehydrogenase

<400> SEQUENCE: 216

Arg Ile Ile Val Glu Lys Pro Phe Gly Arg Asp
1               5                   10

<210> SEQ ID NO 217
<211> LENGTH: 18
<212> TYPE: PRT
<213> ORGANISM: Artificial Sequence
<220> FEATURE:
<223> OTHER INFORMATION: peptide fragment of glucose-6-phosphate
      dehydrogenase

<400> SEQUENCE: 217

Arg Leu Phe Tyr Leu Ala Leu Pro Pro Thr Val Tyr Glu Ala Val Thr
1               5                   10                  15

Lys Asn

<210> SEQ ID NO 218
<211> LENGTH: 18
<212> TYPE: PRT
<213> ORGANISM: Artificial Sequence
<220> FEATURE:
<223> OTHER INFORMATION: peptide fragment of glucose-6-phosphate
      dehydrogenase

<400> SEQUENCE: 218

Arg Leu Asn Ser His Met Asn Ala Leu His Leu Gly Ser Gln Ala Asn
1               5                   10                  15

Arg Leu

<210> SEQ ID NO 219
<211> LENGTH: 12
<212> TYPE: PRT
<213> ORGANISM: Artificial Sequence
<220> FEATURE:
<223> OTHER INFORMATION: peptide fragment of glucose-6-phosphate
      dehydrogenase

<400> SEQUENCE: 219

Arg Leu Ser Asn His Ile Ser Ser Leu Phe Arg Glu
1               5                   10

<210> SEQ ID NO 220
<211> LENGTH: 9
<212> TYPE: PRT
<213> ORGANISM: Artificial Sequence
<220> FEATURE:
<223> OTHER INFORMATION: peptide fragment of glucose-6-phosphate
      dehydrogenase

<400> SEQUENCE: 220
```

```
Arg Leu Thr Val Ala Asp Ile Arg Lys
1               5
```

```
<210> SEQ ID NO 221
<211> LENGTH: 18
<212> TYPE: PRT
<213> ORGANISM: Artificial Sequence
<220> FEATURE:
<223> OTHER INFORMATION: peptide fragment of glucose-6-phosphate
      dehydrogenase

<400> SEQUENCE: 221

Arg Asn Ser Tyr Val Ala Gly Gln Tyr Asp Asp Ala Ala Ser Tyr Gln
1               5                   10                  15

Arg Leu
```

```
<210> SEQ ID NO 222
<211> LENGTH: 12
<212> TYPE: PRT
<213> ORGANISM: Artificial Sequence
<220> FEATURE:
<223> OTHER INFORMATION: peptide fragment of glucose-6-phosphate
      dehydrogenase

<400> SEQUENCE: 222

Arg Val Gly Phe Gln Tyr Glu Gly Thr Tyr Lys Trp
1               5                   10
```

```
<210> SEQ ID NO 223
<211> LENGTH: 12
<212> TYPE: PRT
<213> ORGANISM: Artificial Sequence
<220> FEATURE:
<223> OTHER INFORMATION: peptide fragment of glucose-6-phosphate
      dehydrogenase

<400> SEQUENCE: 223

Arg Val Gln Pro Asn Glu Ala Val Tyr Thr Lys Met
1               5                   10
```

```
<210> SEQ ID NO 224
<211> LENGTH: 11
<212> TYPE: PRT
<213> ORGANISM: Artificial Sequence
<220> FEATURE:
<223> OTHER INFORMATION: peptide fragment of glucose-6-phosphate
      dehydrogenase

<400> SEQUENCE: 224

Arg Trp Asp Gly Val Pro Phe Ile Leu Arg Cys
1               5                   10
```

```
<210> SEQ ID NO 225
<211> LENGTH: 9
<212> TYPE: PRT
<213> ORGANISM: Artificial Sequence
<220> FEATURE:
<223> OTHER INFORMATION: peptide fragment of serpin peptidase inhibitor,
      clade H

<400> SEQUENCE: 225

Lys Ala Ala Thr Leu Ala Glu Arg Ser
1               5
```

```
<210> SEQ ID NO 226
<211> LENGTH: 10
```

```
<212> TYPE: PRT
<213> ORGANISM: Artificial Sequence
<220> FEATURE:
<223> OTHER INFORMATION: peptide fragment of serpin peptidase inhibitor,
      clade H

<400> SEQUENCE: 226

Lys Ala Val Ala Ile Ser Leu Pro Lys Gly
1               5                   10

<210> SEQ ID NO 227
<211> LENGTH: 11
<212> TYPE: PRT
<213> ORGANISM: Artificial Sequence
<220> FEATURE:
<223> OTHER INFORMATION: peptide fragment of serpin peptidase inhibitor,
      clade H

<400> SEQUENCE: 227

Lys Ala Val Leu Ser Ala Glu Gln Leu Arg Asp
1               5                   10

<210> SEQ ID NO 228
<211> LENGTH: 13
<212> TYPE: PRT
<213> ORGANISM: Artificial Sequence
<220> FEATURE:
<223> OTHER INFORMATION: peptide fragment of serpin peptidase inhibitor,
      clade H

<400> SEQUENCE: 228

Lys Gly Val Val Glu Val Thr His Asp Leu Gln Lys His
1               5                   10

<210> SEQ ID NO 229
<211> LENGTH: 15
<212> TYPE: PRT
<213> ORGANISM: Artificial Sequence
<220> FEATURE:
<223> OTHER INFORMATION: peptide fragment of serpin peptidase inhibitor,
      clade H

<400> SEQUENCE: 229

Lys His Leu Ala Gly Leu Gly Leu Thr Glu Ala Ile Asp Lys Asn
1               5                   10                  15

<210> SEQ ID NO 230
<211> LENGTH: 17
<212> TYPE: PRT
<213> ORGANISM: Artificial Sequence
<220> FEATURE:
<223> OTHER INFORMATION: peptide fragment of serpin peptidase inhibitor,
      clade H

<400> SEQUENCE: 230

Lys His Leu Ala Gly Leu Gly Leu Thr Glu Ala Ile Asp Lys Asn Lys
1               5                   10                  15

Ala

<210> SEQ ID NO 231
<211> LENGTH: 11
<212> TYPE: PRT
<213> ORGANISM: Artificial Sequence
<220> FEATURE:
<223> OTHER INFORMATION: peptide fragment of serpin peptidase inhibitor,
      clade H

<400> SEQUENCE: 231
```

Lys Lys Ala Val Ala Ile Ser Leu Pro Lys Gly
1               5                   10

<210> SEQ ID NO 232
<211> LENGTH: 15
<212> TYPE: PRT
<213> ORGANISM: Artificial Sequence
<220> FEATURE:
<223> OTHER INFORMATION: peptide fragment of serpin peptidase inhibitor,
      clade H

<400> SEQUENCE: 232

Lys Lys Pro Ala Ala Ala Ala Pro Gly Thr Ala Glu Lys Leu
1               5                   10                  15

<210> SEQ ID NO 233
<211> LENGTH: 15
<212> TYPE: PRT
<213> ORGANISM: Artificial Sequence
<220> FEATURE:
<223> OTHER INFORMATION: peptide fragment of serpin peptidase inhibitor,
      clade H

<400> SEQUENCE: 233

Lys Leu Phe Tyr Ala Asp His Pro Phe Ile Phe Leu Val Arg Asp
1               5                   10                  15

<210> SEQ ID NO 234
<211> LENGTH: 13
<212> TYPE: PRT
<213> ORGANISM: Artificial Sequence
<220> FEATURE:
<223> OTHER INFORMATION: peptide fragment of serpin peptidase inhibitor,
      clade H

<400> SEQUENCE: 234

Lys Leu Gln Ile Val Glu Met Pro Leu Ala His Lys Leu
1               5                   10

<210> SEQ ID NO 235
<211> LENGTH: 19
<212> TYPE: PRT
<213> ORGANISM: Artificial Sequence
<220> FEATURE:
<223> OTHER INFORMATION: peptide fragment of serpin peptidase inhibitor,
      clade H

<400> SEQUENCE: 235

Lys Leu Ser Ser Leu Ile Ile Leu Met Pro His His Val Glu Pro Leu
1               5                   10                  15

Glu Arg Leu

<210> SEQ ID NO 236
<211> LENGTH: 15
<212> TYPE: PRT
<213> ORGANISM: Artificial Sequence
<220> FEATURE:
<223> OTHER INFORMATION: peptide fragment of serpin peptidase inhibitor,
      clade H

<400> SEQUENCE: 236

Arg Asp Glu Glu Val His Ala Gly Leu Gly Glu Leu Leu Arg Ser
1               5                   10                  15

<210> SEQ ID NO 237
<211> LENGTH: 14

-continued

```
<212> TYPE: PRT
<213> ORGANISM: Artificial Sequence
<220> FEATURE:
<223> OTHER INFORMATION: peptide fragment of serpin peptidase inhibitor,
      clade H

<400> SEQUENCE: 237

Arg Asp Thr Gln Ser Gly Ser Leu Leu Phe Ile Gly Arg Leu
1               5                   10

<210> SEQ ID NO 238
<211> LENGTH: 17
<212> TYPE: PRT
<213> ORGANISM: Artificial Sequence
<220> FEATURE:
<223> OTHER INFORMATION: peptide fragment of serpin peptidase inhibitor,
      clade H

<400> SEQUENCE: 238

Arg Leu Tyr Gly Pro Ser Ser Val Ser Phe Ala Asp Asp Phe Val Arg
1               5                   10                  15

Ser

<210> SEQ ID NO 239
<211> LENGTH: 16
<212> TYPE: PRT
<213> ORGANISM: Artificial Sequence
<220> FEATURE:
<223> OTHER INFORMATION: peptide fragment of serpin peptidase inhibitor,
      clade H

<400> SEQUENCE: 239

Arg Ser Ala Gly Leu Ala Phe Ser Leu Tyr Gln Ala Met Ala Lys Asp
1               5                   10                  15

<210> SEQ ID NO 240
<211> LENGTH: 19
<212> TYPE: PRT
<213> ORGANISM: Artificial Sequence
<220> FEATURE:
<223> OTHER INFORMATION: peptide fragment of serpin peptidase inhibitor,
      clade H

<400> SEQUENCE: 240

Arg Ser Ala Leu Gln Ser Ile Asn Glu Trp Ala Ala Gln Thr Thr Asp
1               5                   10                  15

Gly Lys Leu

<210> SEQ ID NO 241
<211> LENGTH: 25
<212> TYPE: PRT
<213> ORGANISM: Artificial Sequence
<220> FEATURE:
<223> OTHER INFORMATION: peptide fragment of serpin peptidase inhibitor,
      clade H

<400> SEQUENCE: 241

Arg Ser Ala Leu Gln Ser Ile Asn Glu Trp Ala Ala Gln Thr Thr Asp
1               5                   10                  15

Gly Lys Leu Pro Glu Val Thr Lys Asp
                20                  25

<210> SEQ ID NO 242
<211> LENGTH: 29
<212> TYPE: PRT
<213> ORGANISM: Artificial Sequence
```

```
<220> FEATURE:
<223> OTHER INFORMATION: peptide fragment of serpin peptidase inhibitor,
      clade H

<400> SEQUENCE: 242

Arg Ser Ala Leu Gln Ser Ile Asn Glu Trp Ala Ala Gln Thr Thr Asp
1               5                   10                  15

Gly Lys Leu Pro Glu Val Thr Lys Asp Val Glu Arg Thr
            20                  25

<210> SEQ ID NO 243
<211> LENGTH: 13
<212> TYPE: PRT
<213> ORGANISM: Artificial Sequence
<220> FEATURE:
<223> OTHER INFORMATION: peptide fragment of serpin peptidase inhibitor,
      clade H

<400> SEQUENCE: 243

Arg Ser Tyr Thr Val Gly Val Met Met Met His Arg Thr
1               5                   10

<210> SEQ ID NO 244
<211> LENGTH: 21
<212> TYPE: PRT
<213> ORGANISM: Artificial Sequence
<220> FEATURE:
<223> OTHER INFORMATION: peptide fragment of serpin peptidase inhibitor,
      clade H

<400> SEQUENCE: 244

Arg Thr Asp Gly Ala Leu Leu Val Asn Ala Met Phe Phe Lys Pro His
1               5                   10                  15

Trp Asp Glu Lys Phe
            20

<210> SEQ ID NO 245
<211> LENGTH: 13
<212> TYPE: PRT
<213> ORGANISM: Artificial Sequence
<220> FEATURE:
<223> OTHER INFORMATION: peptide fragment of serpin peptidase inhibitor,
      clade H

<400> SEQUENCE: 245

Arg Thr Gly Leu Tyr Asn Tyr Tyr Asp Asp Glu Lys Glu
1               5                   10

<210> SEQ ID NO 246
<211> LENGTH: 15
<212> TYPE: PRT
<213> ORGANISM: Artificial Sequence
<220> FEATURE:
<223> OTHER INFORMATION: peptide fragment of serpin peptidase inhibitor,
      clade H

<400> SEQUENCE: 246

Arg Thr Gly Leu Tyr Asn Tyr Tyr Asp Asp Glu Lys Glu Lys Leu
1               5                   10                  15

<210> SEQ ID NO 247
<211> LENGTH: 30
<212> TYPE: PRT
<213> ORGANISM: Artificial Sequence
<220> FEATURE:
<223> OTHER INFORMATION: peptide fragment of eukaryotic translation
      elongation factor 1 alpha 2
```

```
<400> SEQUENCE: 247

Lys Glu Gly Asn Ala Ser Gly Val Ser Leu Leu Glu Ala Leu Asp Thr
1               5                   10                  15

Ile Leu Pro Pro Thr Arg Pro Thr Asp Lys Pro Leu Arg Leu
            20                  25                  30

<210> SEQ ID NO 248
<211> LENGTH: 9
<212> TYPE: PRT
<213> ORGANISM: Artificial Sequence
<220> FEATURE:
<223> OTHER INFORMATION: peptide fragment of eukaryotic translation
      elongation factor 1 alpha 2

<400> SEQUENCE: 248

Lys Glu Val Ser Ala Tyr Ile Lys Lys
1               5

<210> SEQ ID NO 249
<211> LENGTH: 12
<212> TYPE: PRT
<213> ORGANISM: Artificial Sequence
<220> FEATURE:
<223> OTHER INFORMATION: peptide fragment of eukaryotic translation
      elongation factor 1 alpha 2

<400> SEQUENCE: 249

Lys Phe Glu Lys Glu Ala Ala Glu Met Gly Lys Gly
1               5                   10

<210> SEQ ID NO 250
<211> LENGTH: 13
<212> TYPE: PRT
<213> ORGANISM: Artificial Sequence
<220> FEATURE:
<223> OTHER INFORMATION: peptide fragment of eukaryotic translation
      elongation factor 1 alpha 2

<400> SEQUENCE: 250

Lys Ile Gly Gly Ile Gly Thr Val Pro Val Gly Arg Val
1               5                   10

<210> SEQ ID NO 251
<211> LENGTH: 10
<212> TYPE: PRT
<213> ORGANISM: Artificial Sequence
<220> FEATURE:
<223> OTHER INFORMATION: peptide fragment of eukaryotic translation
      elongation factor 1 alpha 2

<400> SEQUENCE: 251

Lys Gln Leu Ile Val Gly Val Asn Lys Met
1               5                   10

<210> SEQ ID NO 252
<211> LENGTH: 12
<212> TYPE: PRT
<213> ORGANISM: Artificial Sequence
<220> FEATURE:
<223> OTHER INFORMATION: peptide fragment of eukaryotic translation
      elongation factor 1 alpha 2

<400> SEQUENCE: 252

Lys Ser Thr Thr Thr Gly His Leu Ile Tyr Lys Cys
1               5                   10
```

<210> SEQ ID NO 253
<211> LENGTH: 25
<212> TYPE: PRT
<213> ORGANISM: Artificial Sequence
<220> FEATURE:
<223> OTHER INFORMATION: peptide fragment of eukaryotic translation elongation factor 1 alpha 2

<400> SEQUENCE: 253

Lys Ser Val Glu Met His His Glu Ala Leu Ser Glu Ala Leu Pro Gly
1               5                   10                  15

Asp Asn Val Gly Phe Asn Val Lys Asn
            20                  25

<210> SEQ ID NO 254
<211> LENGTH: 17
<212> TYPE: PRT
<213> ORGANISM: Artificial Sequence
<220> FEATURE:
<223> OTHER INFORMATION: peptide fragment of eukaryotic translation elongation factor 1 alpha 2

<400> SEQUENCE: 254

Lys Thr His Ile Asn Ile Val Val Ile Gly His Val Asp Ser Gly Lys
1               5                   10                  15

Ser

<210> SEQ ID NO 255
<211> LENGTH: 9
<212> TYPE: PRT
<213> ORGANISM: Artificial Sequence
<220> FEATURE:
<223> OTHER INFORMATION: peptide fragment of eukaryotic translation elongation factor 1 alpha 2

<400> SEQUENCE: 255

Lys Tyr Ala Trp Val Leu Asp Lys Leu
1               5

<210> SEQ ID NO 256
<211> LENGTH: 14
<212> TYPE: PRT
<213> ORGANISM: Artificial Sequence
<220> FEATURE:
<223> OTHER INFORMATION: peptide fragment of eukaryotic translation elongation factor 1 alpha 2

<400> SEQUENCE: 256

Arg Glu His Ala Leu Leu Ala Tyr Thr Leu Gly Val Lys Gln
1               5                   10

<210> SEQ ID NO 257
<211> LENGTH: 11
<212> TYPE: PRT
<213> ORGANISM: Artificial Sequence
<220> FEATURE:
<223> OTHER INFORMATION: peptide fragment of eukaryotic translation elongation factor 1 alpha 2

<400> SEQUENCE: 257

Arg Gln Thr Val Ala Val Gly Val Ile Lys Asn
1               5                   10

<210> SEQ ID NO 258
<211> LENGTH: 13
<212> TYPE: PRT

```
<213> ORGANISM: Artificial Sequence
<220> FEATURE:
<223> OTHER INFORMATION: peptide fragment of eukaryotic translation
      initiation factor 4A1

<400> SEQUENCE: 258

Lys Ala Thr Gln Ala Leu Val Leu Ala Pro Thr Arg Glu
1               5                   10

<210> SEQ ID NO 259
<211> LENGTH: 11
<212> TYPE: PRT
<213> ORGANISM: Artificial Sequence
<220> FEATURE:
<223> OTHER INFORMATION: peptide fragment of eukaryotic translation
      initiation factor 4A1

<400> SEQUENCE: 259

Lys Asp Gln Ile Tyr Asp Ile Phe Gln Lys Leu
1               5                   10

<210> SEQ ID NO 260
<211> LENGTH: 11
<212> TYPE: PRT
<213> ORGANISM: Artificial Sequence
<220> FEATURE:
<223> OTHER INFORMATION: peptide fragment of eukaryotic translation
      initiation factor 4A1

<400> SEQUENCE: 260

Lys Glu Glu Leu Thr Leu Glu Gly Ile Arg Gln
1               5                   10

<210> SEQ ID NO 261
<211> LENGTH: 15
<212> TYPE: PRT
<213> ORGANISM: Artificial Sequence
<220> FEATURE:
<223> OTHER INFORMATION: peptide fragment of eukaryotic translation
      initiation factor 4A1

<400> SEQUENCE: 261

Lys Gly Val Ala Ile Asn Met Val Thr Glu Glu Asp Lys Arg Thr
1               5                   10                  15

<210> SEQ ID NO 262
<211> LENGTH: 16
<212> TYPE: PRT
<213> ORGANISM: Artificial Sequence
<220> FEATURE:
<223> OTHER INFORMATION: peptide fragment of eukaryotic translation
      initiation factor 4A1

<400> SEQUENCE: 262

Lys Gly Tyr Asp Val Ile Ala Gln Ala Gln Ser Gly Thr Gly Lys Thr
1               5                   10                  15

<210> SEQ ID NO 263
<211> LENGTH: 12
<212> TYPE: PRT
<213> ORGANISM: Artificial Sequence
<220> FEATURE:
<223> OTHER INFORMATION: peptide fragment of eukaryotic translation
      initiation factor 4A1

<400> SEQUENCE: 263

Lys Lys Glu Glu Leu Thr Leu Glu Gly Ile Arg Gln
1               5                   10
```

<210> SEQ ID NO 264
<211> LENGTH: 25
<212> TYPE: PRT
<213> ORGANISM: Artificial Sequence
<220> FEATURE:
<223> OTHER INFORMATION: peptide fragment of eukaryotic translation
      initiation factor 4A1

<400> SEQUENCE: 264

Lys Leu Asn Ser Asn Thr Gln Val Val Leu Leu Ser Ala Thr Met Pro
1               5                   10                  15

Ser Asp Val Leu Glu Val Thr Lys Lys
            20                  25

<210> SEQ ID NO 265
<211> LENGTH: 26
<212> TYPE: PRT
<213> ORGANISM: Artificial Sequence
<220> FEATURE:
<223> OTHER INFORMATION: peptide fragment of eukaryotic translation
      initiation factor 4A1

<400> SEQUENCE: 265

Lys Leu Asn Ser Asn Thr Gln Val Val Leu Leu Ser Ala Thr Met Pro
1               5                   10                  15

Ser Asp Val Leu Glu Val Thr Lys Lys Phe
            20                  25

<210> SEQ ID NO 266
<211> LENGTH: 17
<212> TYPE: PRT
<213> ORGANISM: Artificial Sequence
<220> FEATURE:
<223> OTHER INFORMATION: peptide fragment of eukaryotic translation
      initiation factor 4A1

<400> SEQUENCE: 266

Lys Leu Gln Met Glu Ala Pro His Ile Ile Val Gly Thr Pro Gly Arg
1               5                   10                  15

Val

<210> SEQ ID NO 267
<211> LENGTH: 15
<212> TYPE: PRT
<213> ORGANISM: Artificial Sequence
<220> FEATURE:
<223> OTHER INFORMATION: peptide fragment of eukaryotic translation
      initiation factor 4A1

<400> SEQUENCE: 267

Lys Met Phe Val Leu Asp Glu Ala Asp Glu Met Leu Ser Arg Gly
1               5                   10                  15

<210> SEQ ID NO 268
<211> LENGTH: 16
<212> TYPE: PRT
<213> ORGANISM: Artificial Sequence
<220> FEATURE:
<223> OTHER INFORMATION: peptide fragment of eukaryotic translation
      initiation factor 4A1

<400> SEQUENCE: 268

Arg Asp Phe Thr Val Ser Ala Met His Gly Asp Met Asp Gln Lys Glu
1               5                   10                  15

<210> SEQ ID NO 269
<211> LENGTH: 10
<212> TYPE: PRT
<213> ORGANISM: Artificial Sequence
<220> FEATURE:
<223> OTHER INFORMATION: peptide fragment of eukaryotic translation
      initiation factor 4A1

<400> SEQUENCE: 269

Arg Glu Leu Ala Gln Gln Ile Gln Lys Val
1               5                   10

<210> SEQ ID NO 270
<211> LENGTH: 8
<212> TYPE: PRT
<213> ORGANISM: Artificial Sequence
<220> FEATURE:
<223> OTHER INFORMATION: peptide fragment of eukaryotic translation
      initiation factor 4A1

<400> SEQUENCE: 270

Arg Glu Asn Tyr Ile His Arg Ile
1               5

<210> SEQ ID NO 271
<211> LENGTH: 14
<212> TYPE: PRT
<213> ORGANISM: Artificial Sequence
<220> FEATURE:
<223> OTHER INFORMATION: peptide fragment of eukaryotic translation
      initiation factor 4A1

<400> SEQUENCE: 271

Arg Gly Phe Lys Asp Gln Ile Tyr Asp Ile Phe Gln Lys Leu
1               5                   10

<210> SEQ ID NO 272
<211> LENGTH: 21
<212> TYPE: PRT
<213> ORGANISM: Artificial Sequence
<220> FEATURE:
<223> OTHER INFORMATION: peptide fragment of eukaryotic translation
      initiation factor 4A1

<400> SEQUENCE: 272

Arg Gly Ile Asp Val Gln Gln Val Ser Leu Val Ile Asn Tyr Asp Leu
1               5                   10                  15

Pro Thr Asn Arg Glu
            20

<210> SEQ ID NO 273
<211> LENGTH: 16
<212> TYPE: PRT
<213> ORGANISM: Artificial Sequence
<220> FEATURE:
<223> OTHER INFORMATION: peptide fragment of eukaryotic translation
      initiation factor 4A1

<400> SEQUENCE: 273

Arg Lys Gly Val Ala Ile Asn Met Val Thr Glu Glu Asp Lys Arg Thr
1               5                   10                  15

<210> SEQ ID NO 274
<211> LENGTH: 10
<212> TYPE: PRT
<213> ORGANISM: Artificial Sequence
<220> FEATURE:

<223> OTHER INFORMATION: peptide fragment of eukaryotic translation
      initiation factor 4A1

<400> SEQUENCE: 274

Arg Gln Phe Tyr Ile Asn Val Glu Arg Glu
1               5                   10

<210> SEQ ID NO 275
<211> LENGTH: 9
<212> TYPE: PRT
<213> ORGANISM: Artificial Sequence
<220> FEATURE:
<223> OTHER INFORMATION: peptide fragment of eukaryotic translation
      initiation factor 4A1

<400> SEQUENCE: 275

Arg Val Phe Asp Met Leu Asn Arg Arg
1               5

<210> SEQ ID NO 276
<211> LENGTH: 12
<212> TYPE: PRT
<213> ORGANISM: Artificial Sequence
<220> FEATURE:
<223> OTHER INFORMATION: peptide fragment of eukaryotic translation
      initiation factor 4A1

<400> SEQUENCE: 276

Arg Val Leu Ile Thr Thr Asp Leu Leu Ala Arg Gly
1               5                   10

<210> SEQ ID NO 277
<211> LENGTH: 23
<212> TYPE: PRT
<213> ORGANISM: Artificial Sequence
<220> FEATURE:
<223> OTHER INFORMATION: peptide fragment of kappa-actin

<400> SEQUENCE: 277

Lys Asp Leu Tyr Ala Asn Thr Val Leu Ser Gly Gly Ser Thr Met Tyr
1               5                   10                  15

Pro Gly Ile Ala Asp Arg Met
            20

<210> SEQ ID NO 278
<211> LENGTH: 10
<212> TYPE: PRT
<213> ORGANISM: Artificial Sequence
<220> FEATURE:
<223> OTHER INFORMATION: peptide fragment of kappa-actin

<400> SEQUENCE: 278

Lys Ile Ile Ala Pro Pro Glu Arg Lys Tyr
1               5                   10

<210> SEQ ID NO 279
<211> LENGTH: 10
<212> TYPE: PRT
<213> ORGANISM: Artificial Sequence
<220> FEATURE:
<223> OTHER INFORMATION: peptide fragment of kappa-actin

<400> SEQUENCE: 279

Arg Asp Leu Thr Asp Tyr Leu Met Lys Ile
1               5                   10

<210> SEQ ID NO 280
<211> LENGTH: 13
<212> TYPE: PRT
<213> ORGANISM: Artificial Sequence
<220> FEATURE:
<223> OTHER INFORMATION: peptide fragment of kappa-actin

<400> SEQUENCE: 280

```
Arg His Gln Gly Val Met Val Gly Met Gly Gln Lys Asp
1               5                   10
```

<210> SEQ ID NO 281
<211> LENGTH: 18
<212> TYPE: PRT
<213> ORGANISM: Artificial Sequence
<220> FEATURE:
<223> OTHER INFORMATION: peptide fragment of kappa-actin

<400> SEQUENCE: 281

```
Arg Ser Tyr Glu Leu Pro Asp Gly Gln Val Ile Thr Ile Gly Asn Glu
1               5                   10                  15

Arg Phe
```

<210> SEQ ID NO 282
<211> LENGTH: 32
<212> TYPE: PRT
<213> ORGANISM: Artificial Sequence
<220> FEATURE:
<223> OTHER INFORMATION: peptide fragment of kappa-actin

<400> SEQUENCE: 282

```
Arg Thr Thr Gly Ile Val Met Asp Ser Gly Asp Gly Val Thr His Ile
1               5                   10                  15

Val Pro Ile Tyr Glu Gly Tyr Ala Leu Pro His Ala Ile Leu Arg Leu
            20                  25                  30
```

<210> SEQ ID NO 283
<211> LENGTH: 21
<212> TYPE: PRT
<213> ORGANISM: Artificial Sequence
<220> FEATURE:
<223> OTHER INFORMATION: peptide fragment of glucose-6-phosphate
      isomerase

<400> SEQUENCE: 283

```
Lys Glu Phe Gly Ile Asp Pro Gln Asn Met Phe Glu Phe Trp Asp Trp
1               5                   10                  15

Val Gly Gly Arg Tyr
            20
```

<210> SEQ ID NO 284
<211> LENGTH: 10
<212> TYPE: PRT
<213> ORGANISM: Artificial Sequence
<220> FEATURE:
<223> OTHER INFORMATION: peptide fragment of glucose-6-phosphate
      isomerase

<400> SEQUENCE: 284

```
Lys Glu Trp Phe Leu Gln Ala Ala Lys Asp
1               5                   10
```

<210> SEQ ID NO 285
<211> LENGTH: 13
<212> TYPE: PRT
<213> ORGANISM: Artificial Sequence
<220> FEATURE:
<223> OTHER INFORMATION: peptide fragment of glucose-6-phosphate
      isomerase

<400> SEQUENCE: 285

Lys His Phe Val Ala Leu Ser Thr Asn Thr Thr Lys Val
1               5                   10

<210> SEQ ID NO 286
<211> LENGTH: 17
<212> TYPE: PRT
<213> ORGANISM: Artificial Sequence
<220> FEATURE:
<223> OTHER INFORMATION: peptide fragment of glucose-6-phosphate
      isomerase

<400> SEQUENCE: 286

Lys Ile Leu Leu Ala Asn Phe Leu Ala Gln Thr Glu Ala Leu Met Arg
1               5                   10                  15

Gly

<210> SEQ ID NO 287
<211> LENGTH: 18
<212> TYPE: PRT
<213> ORGANISM: Artificial Sequence
<220> FEATURE:
<223> OTHER INFORMATION: peptide fragment of glucose-6-phosphate
      isomerase

<400> SEQUENCE: 287

Lys Leu Thr Pro Phe Met Leu Gly Ala Leu Val Ala Met Tyr Glu His
1               5                   10                  15

Lys Ile

<210> SEQ ID NO 288
<211> LENGTH: 11
<212> TYPE: PRT
<213> ORGANISM: Artificial Sequence
<220> FEATURE:
<223> OTHER INFORMATION: peptide fragment of glucose-6-phosphate
      isomerase

<400> SEQUENCE: 288

Lys Asn Leu Val Thr Glu Asp Val Met Arg Met
1               5                   10

<210> SEQ ID NO 289
<211> LENGTH: 18
<212> TYPE: PRT
<213> ORGANISM: Artificial Sequence
<220> FEATURE:
<223> OTHER INFORMATION: peptide fragment of glucose-6-phosphate
      isomerase

<400> SEQUENCE: 289

Lys Asn Leu Val Thr Glu Asp Val Met Arg Met Leu Val Asp Leu Ala
1               5                   10                  15

Lys Ser

<210> SEQ ID NO 290
<211> LENGTH: 9
<212> TYPE: PRT
<213> ORGANISM: Artificial Sequence
<220> FEATURE:
<223> OTHER INFORMATION: peptide fragment of glucose-6-phosphate
      isomerase -continued

```
<400> SEQUENCE: 290

Lys Ser Pro Glu Asp Leu Glu Arg Leu
1               5

<210> SEQ ID NO 291
<211> LENGTH: 17
<212> TYPE: PRT
<213> ORGANISM: Artificial Sequence
<220> FEATURE:
<223> OTHER INFORMATION: peptide fragment of glucose-6-phosphate
      isomerase

<400> SEQUENCE: 291

Lys Thr Phe Thr Thr Gln Glu Thr Ile Thr Asn Ala Glu Thr Ala Lys
1               5                   10                  15

Glu

<210> SEQ ID NO 292
<211> LENGTH: 35
<212> TYPE: PRT
<213> ORGANISM: Artificial Sequence
<220> FEATURE:
<223> OTHER INFORMATION: peptide fragment of glucose-6-phosphate
      isomerase

<400> SEQUENCE: 292

Lys Thr Ile Thr Asp Val Ile Asn Ile Gly Ile Gly Gly Ser Asp Leu
1               5                   10                  15

Gly Pro Leu Met Val Thr Glu Ala Leu Lys Pro Tyr Ser Ser Gly Gly
            20                  25                  30

Pro Arg Val
        35

<210> SEQ ID NO 293
<211> LENGTH: 19
<212> TYPE: PRT
<213> ORGANISM: Artificial Sequence
<220> FEATURE:
<223> OTHER INFORMATION: peptide fragment of glucose-6-phosphate
      isomerase

<400> SEQUENCE: 293

Lys Thr Leu Ala Gln Leu Asn Pro Glu Ser Ser Leu Phe Ile Ile Ala
1               5                   10                  15

Ser Lys Thr

<210> SEQ ID NO 294
<211> LENGTH: 17
<212> TYPE: PRT
<213> ORGANISM: Artificial Sequence
<220> FEATURE:
<223> OTHER INFORMATION: peptide fragment of glucose-6-phosphate
      isomerase

<400> SEQUENCE: 294

Lys Val Phe Glu Gly Asn Arg Pro Thr Asn Ser Ile Val Phe Thr Lys
1               5                   10                  15

Leu

<210> SEQ ID NO 295
<211> LENGTH: 23
<212> TYPE: PRT
<213> ORGANISM: Artificial Sequence
```

```
<220> FEATURE:
<223> OTHER INFORMATION: peptide fragment of glucose-6-phosphate
      isomerase

<400> SEQUENCE: 295

Lys Val Lys Glu Phe Gly Ile Asp Pro Gln Asn Met Phe Glu Phe Trp
1               5                   10                  15

Asp Trp Val Gly Gly Arg Tyr
            20

<210> SEQ ID NO 296
<211> LENGTH: 17
<212> TYPE: PRT
<213> ORGANISM: Artificial Sequence
<220> FEATURE:
<223> OTHER INFORMATION: peptide fragment of glucose-6-phosphate
      isomerase

<400> SEQUENCE: 296

Arg Phe Ala Ala Tyr Phe Gln Gln Gly Asp Met Glu Ser Asn Gly Lys
1               5                   10                  15

Tyr

<210> SEQ ID NO 297
<211> LENGTH: 9
<212> TYPE: PRT
<213> ORGANISM: Artificial Sequence
<220> FEATURE:
<223> OTHER INFORMATION: peptide fragment of glucose-6-phosphate
      isomerase

<400> SEQUENCE: 297

Arg Met Leu Val Asp Leu Ala Lys Ser
1               5

<210> SEQ ID NO 298
<211> LENGTH: 12
<212> TYPE: PRT
<213> ORGANISM: Artificial Sequence
<220> FEATURE:
<223> OTHER INFORMATION: peptide fragment of glucose-6-phosphate
      isomerase

<400> SEQUENCE: 298

Arg Ser Asn Thr Pro Ile Leu Val Asp Gly Lys Asp
1               5                   10

<210> SEQ ID NO 299
<211> LENGTH: 20
<212> TYPE: PRT
<213> ORGANISM: Artificial Sequence
<220> FEATURE:
<223> OTHER INFORMATION: peptide fragment of glucose-6-phosphate
      isomerase

<400> SEQUENCE: 299

Arg Ser Asn Thr Pro Ile Leu Val Asp Gly Lys Asp Val Met Pro Glu
1               5                   10                  15

Val Asn Lys Val
            20

<210> SEQ ID NO 300
<211> LENGTH: 32
<212> TYPE: PRT
<213> ORGANISM: Artificial Sequence
<220> FEATURE:
```

```
<223> OTHER INFORMATION: peptide fragment of glucose-6-phosphate
      isomerase

<400> SEQUENCE: 300

Arg Val Asp His Gln Thr Gly Pro Ile Val Trp Gly Glu Pro Gly Thr
1               5                   10                  15

Asn Gly Gln His Ala Phe Tyr Gln Leu Ile His Gln Gly Thr Lys Met
            20                  25                  30

<210> SEQ ID NO 301
<211> LENGTH: 16
<212> TYPE: PRT
<213> ORGANISM: Artificial Sequence
<220> FEATURE:
<223> OTHER INFORMATION: peptide fragment of glucose-6-phosphate
      isomerase

<400> SEQUENCE: 301

Arg Val Trp Tyr Val Ser Asn Ile Asp Gly Thr His Ile Ala Lys Thr
1               5                   10                  15

<210> SEQ ID NO 302
<211> LENGTH: 20
<212> TYPE: PRT
<213> ORGANISM: Artificial Sequence
<220> FEATURE:
<223> OTHER INFORMATION: peptide fragment of Tu translation elongation
      factor, mitochondrial

<400> SEQUENCE: 302

Lys Ala Asp Ala Val Gln Asp Ser Glu Met Val Glu Leu Val Glu Leu
1               5                   10                  15

Glu Ile Arg Glu
            20

<210> SEQ ID NO 303
<211> LENGTH: 12
<212> TYPE: PRT
<213> ORGANISM: Artificial Sequence
<220> FEATURE:
<223> OTHER INFORMATION: peptide fragment of Tu translation elongation
      factor, mitochondrial

<400> SEQUENCE: 303

Lys Glu Leu Ala Met Pro Gly Glu Asp Leu Lys Phe
1               5                   10

<210> SEQ ID NO 304
<211> LENGTH: 11
<212> TYPE: PRT
<213> ORGANISM: Artificial Sequence
<220> FEATURE:
<223> OTHER INFORMATION: peptide fragment of Tu translation elongation
      factor, mitochondrial

<400> SEQUENCE: 304

Lys Ile Leu Ala Glu Gly Gly Gly Ala Lys Phe
1               5                   10

<210> SEQ ID NO 305
<211> LENGTH: 14
<212> TYPE: PRT
<213> ORGANISM: Artificial Sequence
<220> FEATURE:
<223> OTHER INFORMATION: peptide fragment of Tu translation elongation
      factor, mitochondrial
```

```
<400> SEQUENCE: 305

Lys Lys Tyr Glu Glu Ile Asp Asn Ala Pro Glu Glu Arg Ala
1               5                   10

<210> SEQ ID NO 306
<211> LENGTH: 16
<212> TYPE: PRT
<213> ORGANISM: Artificial Sequence
<220> FEATURE:
<223> OTHER INFORMATION: peptide fragment of Tu translation elongation
      factor, mitochondrial

<400> SEQUENCE: 306

Lys Leu Leu Asp Ala Val Asp Thr Tyr Ile Pro Val Pro Ala Arg Asp
1               5                   10                  15

<210> SEQ ID NO 307
<211> LENGTH: 11
<212> TYPE: PRT
<213> ORGANISM: Artificial Sequence
<220> FEATURE:
<223> OTHER INFORMATION: peptide fragment of Tu translation elongation
      factor, mitochondrial

<400> SEQUENCE: 307

Lys Thr Thr Leu Thr Ala Ala Ile Thr Lys Ile
1               5                   10

<210> SEQ ID NO 308
<211> LENGTH: 12
<212> TYPE: PRT
<213> ORGANISM: Artificial Sequence
<220> FEATURE:
<223> OTHER INFORMATION: peptide fragment of Tu translation elongation
      factor, mitochondrial

<400> SEQUENCE: 308

Lys Val Glu Ala Gln Val Tyr Ile Leu Ser Lys Glu
1               5                   10

<210> SEQ ID NO 309
<211> LENGTH: 14
<212> TYPE: PRT
<213> ORGANISM: Artificial Sequence
<220> FEATURE:
<223> OTHER INFORMATION: peptide fragment of Tu translation elongation
      factor, mitochondrial

<400> SEQUENCE: 309

Arg Ala Glu Ala Gly Asp Asn Leu Gly Ala Leu Val Arg Gly
1               5                   10

<210> SEQ ID NO 310
<211> LENGTH: 19
<212> TYPE: PRT
<213> ORGANISM: Artificial Sequence
<220> FEATURE:
<223> OTHER INFORMATION: peptide fragment of Tu translation elongation
      factor, mitochondrial

<400> SEQUENCE: 310

Arg Asp Lys Pro His Val Asn Val Gly Thr Ile Gly His Val Asp His
1               5                   10                  15

Gly Lys Thr

<210> SEQ ID NO 311
```

```
<211> LENGTH: 21
<212> TYPE: PRT
<213> ORGANISM: Artificial Sequence
<220> FEATURE:
<223> OTHER INFORMATION: peptide fragment of Tu translation elongation
      factor, mitochondrial

<400> SEQUENCE: 311

Arg Asp Leu Glu Lys Pro Phe Leu Leu Pro Val Glu Ala Val Tyr Ser
1               5                   10                  15

Val Pro Gly Arg Gly
            20

<210> SEQ ID NO 312
<211> LENGTH: 9
<212> TYPE: PRT
<213> ORGANISM: Artificial Sequence
<220> FEATURE:
<223> OTHER INFORMATION: peptide fragment of Tu translation elongation
      factor, mitochondrial

<400> SEQUENCE: 312

Arg Glu His Leu Leu Leu Ala Arg Gln
1               5

<210> SEQ ID NO 313
<211> LENGTH: 11
<212> TYPE: PRT
<213> ORGANISM: Artificial Sequence
<220> FEATURE:
<223> OTHER INFORMATION: peptide fragment of Tu translation elongation
      factor, mitochondrial

<400> SEQUENCE: 313

Arg Glu Leu Leu Thr Glu Phe Gly Tyr Lys Gly
1               5                   10

<210> SEQ ID NO 314
<211> LENGTH: 18
<212> TYPE: PRT
<213> ORGANISM: Artificial Sequence
<220> FEATURE:
<223> OTHER INFORMATION: peptide fragment of Tu translation elongation
      factor, mitochondrial

<400> SEQUENCE: 314

Arg Gly Ile Thr Ile Asn Ala Ala His Val Glu Tyr Ser Thr Ala Ala
1               5                   10                  15

Arg His

<210> SEQ ID NO 315
<211> LENGTH: 12
<212> TYPE: PRT
<213> ORGANISM: Artificial Sequence
<220> FEATURE:
<223> OTHER INFORMATION: peptide fragment of Tu translation elongation
      factor, mitochondrial

<400> SEQUENCE: 315

Arg Gly Thr Val Val Thr Gly Thr Leu Glu Arg Gly
1               5                   10

<210> SEQ ID NO 316
<211> LENGTH: 19
<212> TYPE: PRT
<213> ORGANISM: Artificial Sequence
<220> FEATURE:
```

```
<223> OTHER INFORMATION: peptide fragment of Tu translation elongation
      factor, mitochondrial

<400> SEQUENCE: 316

Arg Ile Ile Leu Pro Pro Glu Lys Glu Leu Ala Met Pro Gly Glu Asp
1               5                   10                  15

Leu Lys Phe

<210> SEQ ID NO 317
<211> LENGTH: 15
<212> TYPE: PRT
<213> ORGANISM: Artificial Sequence
<220> FEATURE:
<223> OTHER INFORMATION: peptide fragment of Tu translation elongation
      factor, mitochondrial

<400> SEQUENCE: 317

Arg Gln Ile Gly Val Glu His Val Val Val Tyr Val Asn Lys Ala
1               5                   10                  15

<210> SEQ ID NO 318
<211> LENGTH: 20
<212> TYPE: PRT
<213> ORGANISM: Artificial Sequence
<220> FEATURE:
<223> OTHER INFORMATION: peptide fragment of Tu translation elongation
      factor, mitochondrial

<400> SEQUENCE: 318

Arg Thr Ile Gly Thr Gly Leu Val Thr Asn Thr Leu Ala Met Thr Glu
1               5                   10                  15

Glu Glu Lys Asn
            20

<210> SEQ ID NO 319
<211> LENGTH: 13
<212> TYPE: PRT
<213> ORGANISM: Artificial Sequence
<220> FEATURE:
<223> OTHER INFORMATION: peptide fragment of Tu translation elongation
      factor, mitochondrial

<400> SEQUENCE: 319

Arg Thr Val Val Thr Gly Ile Glu Met Phe His Lys Ser
1               5                   10

<210> SEQ ID NO 320
<211> LENGTH: 12
<212> TYPE: PRT
<213> ORGANISM: Artificial Sequence
<220> FEATURE:
<223> OTHER INFORMATION: peptide fragment of alpha actin

<400> SEQUENCE: 320

Lys Ala Gly Phe Ala Gly Asp Asp Ala Pro Arg Ala
1               5                   10

<210> SEQ ID NO 321
<211> LENGTH: 13
<212> TYPE: PRT
<213> ORGANISM: Artificial Sequence
<220> FEATURE:
<223> OTHER INFORMATION: peptide fragment of alpha actin

<400> SEQUENCE: 321

Lys Asp Ser Tyr Val Gly Asp Glu Ala Gln Ser Lys Arg
```

<210> SEQ ID NO 322
<211> LENGTH: 13
<212> TYPE: PRT
<213> ORGANISM: Artificial Sequence
<220> FEATURE:
<223> OTHER INFORMATION: peptide fragment of alpha actin

<400> SEQUENCE: 322

Lys Glu Ile Thr Ala Leu Ala Pro Ser Thr Met Lys Ile
1               5                   10

<210> SEQ ID NO 323
<211> LENGTH: 15
<212> TYPE: PRT
<213> ORGANISM: Artificial Sequence
<220> FEATURE:
<223> OTHER INFORMATION: peptide fragment of alpha actin

<400> SEQUENCE: 323

Lys Gln Glu Tyr Asp Glu Ala Gly Pro Ser Ile Val His Arg Lys
1               5                   10                  15

<210> SEQ ID NO 324
<211> LENGTH: 18
<212> TYPE: PRT
<213> ORGANISM: Artificial Sequence
<220> FEATURE:
<223> OTHER INFORMATION: peptide fragment of alpha actin

<400> SEQUENCE: 324

Lys Tyr Pro Ile Glu His Gly Ile Ile Thr Asn Trp Asp Asp Met Glu
1               5                   10                  15

Lys Ile

<210> SEQ ID NO 325
<211> LENGTH: 13
<212> TYPE: PRT
<213> ORGANISM: Artificial Sequence
<220> FEATURE:
<223> OTHER INFORMATION: peptide fragment of alpha actin

<400> SEQUENCE: 325

Arg Ala Val Phe Pro Ser Ile Val Gly Arg Pro Arg His
1               5                   10

<210> SEQ ID NO 326
<211> LENGTH: 13
<212> TYPE: PRT
<213> ORGANISM: Artificial Sequence
<220> FEATURE:
<223> OTHER INFORMATION: peptide fragment of alpha actin

<400> SEQUENCE: 326

Lys Asp Ser Tyr Val Gly His Glu Ala Gln Ser Lys Arg
1               5                   10

<210> SEQ ID NO 327
<211> LENGTH: 23
<212> TYPE: PRT
<213> ORGANISM: Artificial Sequence
<220> FEATURE:
<223> OTHER INFORMATION: peptide fragment of alpha actin

<400> SEQUENCE: 327

-continued

```
Lys Asp Leu Tyr Ala Asn Asn Val Met Ser Gly Gly Thr Thr Met Tyr
1               5                   10                  15

Pro Gly Ile Ala Asp Arg Met
            20
```

<210> SEQ ID NO 328
<211> LENGTH: 13
<212> TYPE: PRT
<213> ORGANISM: Artificial Sequence
<220> FEATURE:
<223> OTHER INFORMATION: peptide fragment of alpha actin

<400> SEQUENCE: 328

```
Lys Ile Trp His His Thr Phe Tyr Asn Glu Leu Arg Val
1               5                   10
```

<210> SEQ ID NO 329
<211> LENGTH: 9
<212> TYPE: PRT
<213> ORGANISM: Artificial Sequence
<220> FEATURE:
<223> OTHER INFORMATION: peptide fragment of chaperonin containing TCP1,
      subunit 7 (eta)

<400> SEQUENCE: 329

```
Lys Ala Leu Glu Ile Ile Pro Arg Gln
1               5
```

<210> SEQ ID NO 330
<211> LENGTH: 14
<212> TYPE: PRT
<213> ORGANISM: Artificial Sequence
<220> FEATURE:
<223> OTHER INFORMATION: peptide fragment of chaperonin containing TCP1,
      subunit 7 (eta)

<400> SEQUENCE: 330

```
Lys Ala Thr Ile Ser Asn Asp Gly Ala Thr Ile Leu Lys Leu
1               5                   10
```

<210> SEQ ID NO 331
<211> LENGTH: 12
<212> TYPE: PRT
<213> ORGANISM: Artificial Sequence
<220> FEATURE:
<223> OTHER INFORMATION: peptide fragment of chaperonin containing TCP1,
      subunit 7 (eta)

<400> SEQUENCE: 331

```
Lys Leu Leu Asp Val Val His Pro Ala Ala Lys Thr
1               5                   10
```

<210> SEQ ID NO 332
<211> LENGTH: 16
<212> TYPE: PRT
<213> ORGANISM: Artificial Sequence
<220> FEATURE:
<223> OTHER INFORMATION: peptide fragment of chaperonin containing TCP1,
      subunit 7 (eta)

<400> SEQUENCE: 332

```
Lys Leu Pro Ile Gly Asp Val Ala Thr Gln Tyr Phe Ala Asp Arg Asp
1               5                   10                  15
```

<210> SEQ ID NO 333
<211> LENGTH: 18
<212> TYPE: PRT

```
<213> ORGANISM: Artificial Sequence
<220> FEATURE:
<223> OTHER INFORMATION: peptide fragment of chaperonin containing TCP1,
      subunit 7 (eta)

<400> SEQUENCE: 333

Lys Met Val Val Asp Ala Val Met Met Leu Asp Asp Leu Leu Gln Leu
1               5                   10                  15

Lys Met

<210> SEQ ID NO 334
<211> LENGTH: 19
<212> TYPE: PRT
<213> ORGANISM: Artificial Sequence
<220> FEATURE:
<223> OTHER INFORMATION: peptide fragment of chaperonin containing TCP1,
      subunit 7 (eta)

<400> SEQUENCE: 334

Lys Asn Asp Ser Val Val Ala Gly Gly Gly Ala Ile Glu Met Glu Leu
1               5                   10                  15

Ser Lys Tyr

<210> SEQ ID NO 335
<211> LENGTH: 12
<212> TYPE: PRT
<213> ORGANISM: Artificial Sequence
<220> FEATURE:
<223> OTHER INFORMATION: peptide fragment of chaperonin containing TCP1,
      subunit 7 (eta)

<400> SEQUENCE: 335

Lys Gln Gln Leu Leu Ile Gly Ala Tyr Ala Lys Ala
1               5                   10

<210> SEQ ID NO 336
<211> LENGTH: 24
<212> TYPE: PRT
<213> ORGANISM: Artificial Sequence
<220> FEATURE:
<223> OTHER INFORMATION: peptide fragment of chaperonin containing TCP1,
      subunit 7 (eta)

<400> SEQUENCE: 336

Lys Ser Gln Asp Ala Glu Val Gly Asp Gly Thr Thr Ser Val Thr Leu
1               5                   10                  15

Leu Ala Ala Glu Phe Leu Lys Gln
            20

<210> SEQ ID NO 337
<211> LENGTH: 14
<212> TYPE: PRT
<213> ORGANISM: Artificial Sequence
<220> FEATURE:
<223> OTHER INFORMATION: peptide fragment of chaperonin containing TCP1,
      subunit 7 (eta)

<400> SEQUENCE: 337

Lys Thr Phe Ser Tyr Ala Gly Phe Glu Met Gln Pro Lys Lys
1               5                   10

<210> SEQ ID NO 338
<211> LENGTH: 20
<212> TYPE: PRT
<213> ORGANISM: Artificial Sequence
<220> FEATURE:
```

```
<223> OTHER INFORMATION: peptide fragment of chaperonin containing TCP1,
      subunit 7 (eta)

<400> SEQUENCE: 338

Lys Val Gln Gly Gly Ala Leu Glu Asp Ser Gln Leu Val Ala Gly Val
1               5                   10                  15

Ala Phe Lys Lys
            20

<210> SEQ ID NO 339
<211> LENGTH: 14
<212> TYPE: PRT
<213> ORGANISM: Artificial Sequence
<220> FEATURE:
<223> OTHER INFORMATION: peptide fragment of chaperonin containing TCP1,
      subunit 7 (eta)

<400> SEQUENCE: 339

Arg Gly Gly Ala Glu Gln Phe Met Glu Glu Thr Glu Arg Ser
1               5                   10

<210> SEQ ID NO 340
<211> LENGTH: 13
<212> TYPE: PRT
<213> ORGANISM: Artificial Sequence
<220> FEATURE:
<223> OTHER INFORMATION: peptide fragment of chaperonin containing TCP1,
      subunit 7 (eta)

<400> SEQUENCE: 340

Arg Ser Thr Val Asp Ala Pro Thr Ala Ala Gly Arg Gly
1               5                   10

<210> SEQ ID NO 341
<211> LENGTH: 26
<212> TYPE: PRT
<213> ORGANISM: Artificial Sequence
<220> FEATURE:
<223> OTHER INFORMATION: peptide fragment of chaperonin containing TCP1,
      subunit 7 (eta)

<400> SEQUENCE: 341

Arg Val His Thr Val Glu Asp Tyr Gln Ala Ile Val Asp Ala Glu Trp
1               5                   10                  15

Asn Ile Leu Tyr Asp Lys Leu Glu Lys Ile
            20                  25

<210> SEQ ID NO 342
<211> LENGTH: 19
<212> TYPE: PRT
<213> ORGANISM: Artificial Sequence
<220> FEATURE:
<223> OTHER INFORMATION: peptide fragment of integrin-linked kinase

<400> SEQUENCE: 342

Lys Gly Ile Glu Ile Leu Thr Asp Met Ser Arg Pro Val Glu Leu Ser
1               5                   10                  15

Asp Arg Glu

<210> SEQ ID NO 343
<211> LENGTH: 33
<212> TYPE: PRT
<213> ORGANISM: Artificial Sequence
<220> FEATURE:
<223> OTHER INFORMATION: peptide fragment of integrin-linked kinase
```

<400> SEQUENCE: 343

Lys Gly Ile Glu Ile Leu Thr Asp Met Ser Arg Pro Val Glu Leu Ser
1               5                   10                  15

Asp Arg Glu Thr Leu Leu Asn Ser Ala Thr Thr Ser Leu Asn Ser Lys
            20                  25                  30

Val

<210> SEQ ID NO 344
<211> LENGTH: 10
<212> TYPE: PRT
<213> ORGANISM: Artificial Sequence
<220> FEATURE:
<223> OTHER INFORMATION: peptide fragment of integrin-linked kinase

<400> SEQUENCE: 344

Lys Leu Val Ile Glu Glu Ala Glu Arg Ser
1               5                   10

<210> SEQ ID NO 345
<211> LENGTH: 22
<212> TYPE: PRT
<213> ORGANISM: Artificial Sequence
<220> FEATURE:
<223> OTHER INFORMATION: peptide fragment of integrin-linked kinase

<400> SEQUENCE: 345

Lys Met Ile Gln Asp Gly Lys Gly Asp Val Thr Ile Thr Asn Asp Gly
1               5                   10                  15

Ala Thr Ile Leu Lys Gln
            20

<210> SEQ ID NO 346
<211> LENGTH: 19
<212> TYPE: PRT
<213> ORGANISM: Artificial Sequence
<220> FEATURE:
<223> OTHER INFORMATION: peptide fragment of integrin-linked kinase

<400> SEQUENCE: 346

Lys Thr Asp Met Asp Asn Gln Ile Val Val Ser Asp Tyr Ala Gln Met
1               5                   10                  15

Asp Arg Val

<210> SEQ ID NO 347
<211> LENGTH: 15
<212> TYPE: PRT
<213> ORGANISM: Artificial Sequence
<220> FEATURE:
<223> OTHER INFORMATION: peptide fragment of integrin-linked kinase

<400> SEQUENCE: 347

Lys Val Ile Asp Pro Ala Thr Ala Thr Ser Val Asp Leu Arg Asp
1               5                   10                  15

<210> SEQ ID NO 348
<211> LENGTH: 10
<212> TYPE: PRT
<213> ORGANISM: Artificial Sequence
<220> FEATURE:
<223> OTHER INFORMATION: peptide fragment of integrin-linked kinase

<400> SEQUENCE: 348

Lys Val Ser Asn Ser Gly Ile Thr Arg Val
1               5                   10

```
<210> SEQ ID NO 349
<211> LENGTH: 21
<212> TYPE: PRT
<213> ORGANISM: Artificial Sequence
<220> FEATURE:
<223> OTHER INFORMATION: peptide fragment of integrin-linked kinase

<400> SEQUENCE: 349

Lys Val Val Ser Gln Tyr Ser Ser Leu Leu Ser Pro Met Ser Val Asn
1               5                   10                  15

Ala Val Met Lys Val
            20

<210> SEQ ID NO 350
<211> LENGTH: 31
<212> TYPE: PRT
<213> ORGANISM: Artificial Sequence
<220> FEATURE:
<223> OTHER INFORMATION: peptide fragment of integrin-linked kinase

<400> SEQUENCE: 350

Arg Ala Phe Ala Asp Ala Met Glu Val Ile Pro Ser Thr Leu Ala Glu
1               5                   10                  15

Asn Ala Gly Leu Asn Pro Ile Ser Thr Val Thr Glu Leu Arg Asn
            20                  25                  30

<210> SEQ ID NO 351
<211> LENGTH: 18
<212> TYPE: PRT
<213> ORGANISM: Artificial Sequence
<220> FEATURE:
<223> OTHER INFORMATION: peptide fragment of integrin-linked kinase

<400> SEQUENCE: 351

Arg Ala Leu Ile Ala Gly Gly Gly Ala Pro Glu Ile Glu Leu Ala Leu
1               5                   10                  15

Arg Leu

<210> SEQ ID NO 352
<211> LENGTH: 10
<212> TYPE: PRT
<213> ORGANISM: Artificial Sequence
<220> FEATURE:
<223> OTHER INFORMATION: peptide fragment of integrin-linked kinase

<400> SEQUENCE: 352

Arg Ala Tyr Ile Leu Asn Leu Val Lys Gln
1               5                   10

<210> SEQ ID NO 353
<211> LENGTH: 15
<212> TYPE: PRT
<213> ORGANISM: Artificial Sequence
<220> FEATURE:
<223> OTHER INFORMATION: peptide fragment of integrin-linked kinase

<400> SEQUENCE: 353

Arg Asp Ala Leu Ser Asp Leu Ala Leu His Phe Leu Asn Lys Met
1               5                   10                  15

<210> SEQ ID NO 354
<211> LENGTH: 11
<212> TYPE: PRT
<213> ORGANISM: Artificial Sequence
```

```
<220> FEATURE:
<223> OTHER INFORMATION: peptide fragment of phosphoglycerate
      dehydrogenase

<400> SEQUENCE: 354

Lys Phe Met Gly Thr Glu Leu Asn Gly Lys Thr
1               5                   10

<210> SEQ ID NO 355
<211> LENGTH: 14
<212> TYPE: PRT
<213> ORGANISM: Artificial Sequence
<220> FEATURE:
<223> OTHER INFORMATION: peptide fragment of phosphoglycerate
      dehydrogenase

<400> SEQUENCE: 355

Lys Ile Leu Gln Asp Gly Gly Leu Gln Val Val Glu Lys Gln
1               5                   10

<210> SEQ ID NO 356
<211> LENGTH: 12
<212> TYPE: PRT
<213> ORGANISM: Artificial Sequence
<220> FEATURE:
<223> OTHER INFORMATION: peptide fragment of phosphoglycerate
      dehydrogenase

<400> SEQUENCE: 356

Lys Gln Ala Asp Val Asn Leu Val Asn Ala Lys Leu
1               5                   10

<210> SEQ ID NO 357
<211> LENGTH: 12
<212> TYPE: PRT
<213> ORGANISM: Artificial Sequence
<220> FEATURE:
<223> OTHER INFORMATION: peptide fragment of phosphoglycerate
      dehydrogenase

<400> SEQUENCE: 357

Lys Gln His Val Thr Glu Ala Phe Gln Phe His Phe
1               5                   10

<210> SEQ ID NO 358
<211> LENGTH: 11
<212> TYPE: PRT
<213> ORGANISM: Artificial Sequence
<220> FEATURE:
<223> OTHER INFORMATION: peptide fragment of phosphoglycerate
      dehydrogenase

<400> SEQUENCE: 358

Lys Thr Leu Gly Ile Leu Gly Leu Gly Arg Ile
1               5                   10

<210> SEQ ID NO 359
<211> LENGTH: 13
<212> TYPE: PRT
<213> ORGANISM: Artificial Sequence
<220> FEATURE:
<223> OTHER INFORMATION: peptide fragment of phosphoglycerate
      dehydrogenase

<400> SEQUENCE: 359

Lys Val Thr Ala Asp Val Ile Asn Ala Ala Glu Lys Leu
1               5                   10
```

<210> SEQ ID NO 360
<211> LENGTH: 17
<212> TYPE: PRT
<213> ORGANISM: Artificial Sequence
<220> FEATURE:
<223> OTHER INFORMATION: peptide fragment of phosphoglycerate
      dehydrogenase

<400> SEQUENCE: 360

Arg Ala Gly Thr Gly Val Asp Asn Val Asp Leu Glu Ala Ala Thr Arg
1               5                   10                  15

Lys

<210> SEQ ID NO 361
<211> LENGTH: 25
<212> TYPE: PRT
<213> ORGANISM: Artificial Sequence
<220> FEATURE:
<223> OTHER INFORMATION: peptide fragment of phosphoglycerate
      dehydrogenase

<400> SEQUENCE: 361

Arg Ala Leu Gln Ser Gly Gln Cys Ala Gly Ala Ala Leu Asp Val Phe
1               5                   10                  15

Thr Glu Glu Pro Pro Arg Asp Arg Ala
            20                  25

<210> SEQ ID NO 362
<211> LENGTH: 16
<212> TYPE: PRT
<213> ORGANISM: Artificial Sequence
<220> FEATURE:
<223> OTHER INFORMATION: peptide fragment of phosphoglycerate
      dehydrogenase

<400> SEQUENCE: 362

Arg Cys Gly Glu Glu Ile Ala Val Gln Phe Val Asp Met Val Lys Gly
1               5                   10                  15

<210> SEQ ID NO 363
<211> LENGTH: 10
<212> TYPE: PRT
<213> ORGANISM: Artificial Sequence
<220> FEATURE:
<223> OTHER INFORMATION: peptide fragment of phosphoglycerate
      dehydrogenase

<400> SEQUENCE: 363

Arg Asp Leu Pro Leu Leu Leu Phe Arg Thr
1               5                   10

<210> SEQ ID NO 364
<211> LENGTH: 13
<212> TYPE: PRT
<213> ORGANISM: Artificial Sequence
<220> FEATURE:
<223> OTHER INFORMATION: peptide fragment of phosphoglycerate
      dehydrogenase

<400> SEQUENCE: 364

Arg Gly Gly Ile Val Asp Glu Gly Ala Leu Leu Arg Ala
1               5                   10

<210> SEQ ID NO 365
<211> LENGTH: 12
<212> TYPE: PRT

```
<213> ORGANISM: Artificial Sequence
<220> FEATURE:
<223> OTHER INFORMATION: peptide fragment of phosphoglycerate
      dehydrogenase

<400> SEQUENCE: 365

Arg Gln Ile Pro Gln Ala Thr Ala Ser Met Lys Asp
1               5                   10

<210> SEQ ID NO 366
<211> LENGTH: 24
<212> TYPE: PRT
<213> ORGANISM: Artificial Sequence
<220> FEATURE:
<223> OTHER INFORMATION: peptide fragment of phosphoglycerate
      dehydrogenase

<400> SEQUENCE: 366

Arg Thr Gln Thr Ser Asp Pro Ala Met Leu Pro Thr Met Ile Gly Leu
1               5                   10                  15

Leu Ala Glu Ala Gly Val Arg Leu
            20

<210> SEQ ID NO 367
<211> LENGTH: 12
<212> TYPE: PRT
<213> ORGANISM: Artificial Sequence
<220> FEATURE:
<223> OTHER INFORMATION: peptide fragment of Sjogren syndrome antigen B
      (autoantigen La)

<400> SEQUENCE: 367

Lys Asp Ala Asn Asn Gly Asn Leu Gln Leu Arg Asn
1               5                   10

<210> SEQ ID NO 368
<211> LENGTH: 15
<212> TYPE: PRT
<213> ORGANISM: Artificial Sequence
<220> FEATURE:
<223> OTHER INFORMATION: peptide fragment of Sjogren syndrome antigen B
      (autoantigen La)

<400> SEQUENCE: 368

Lys Glu Val Thr Trp Glu Val Leu Glu Gly Glu Val Glu Lys Glu
1               5                   10                  15

<210> SEQ ID NO 369
<211> LENGTH: 20
<212> TYPE: PRT
<213> ORGANISM: Artificial Sequence
<220> FEATURE:
<223> OTHER INFORMATION: peptide fragment of Sjogren syndrome antigen B
      (autoantigen La)

<400> SEQUENCE: 369

Lys Gly Phe Pro Thr Asp Ala Thr Leu Asp Asp Ile Lys Glu Trp Leu
1               5                   10                  15

Glu Asp Lys Gly
            20

<210> SEQ ID NO 370
<211> LENGTH: 29
<212> TYPE: PRT
<213> ORGANISM: Artificial Sequence
<220> FEATURE:
<223> OTHER INFORMATION: peptide fragment of Sjogren syndrome antigen B
```

(autoantigen La)

<400> SEQUENCE: 370

Lys Gly Phe Pro Thr Asp Ala Thr Leu Asp Ile Lys Glu Trp Leu
1               5                   10                  15

Glu Asp Lys Gly Gln Val Leu Asn Ile Gln Met Arg Arg
            20                  25

<210> SEQ ID NO 371
<211> LENGTH: 11
<212> TYPE: PRT
<213> ORGANISM: Artificial Sequence
<220> FEATURE:
<223> OTHER INFORMATION: peptide fragment of Sjogren syndrome antigen B
      (autoantigen La)

<400> SEQUENCE: 371

Lys Gly Gln Val Leu Asn Ile Gln Met Arg Arg
1               5                   10

<210> SEQ ID NO 372
<211> LENGTH: 16
<212> TYPE: PRT
<213> ORGANISM: Artificial Sequence
<220> FEATURE:
<223> OTHER INFORMATION: peptide fragment of Sjogren syndrome antigen B
      (autoantigen La)

<400> SEQUENCE: 372

Lys Gly Ser Ile Phe Val Val Phe Asp Ser Ile Glu Ser Ala Lys Lys
1               5                   10                  15

<210> SEQ ID NO 373
<211> LENGTH: 13
<212> TYPE: PRT
<213> ORGANISM: Artificial Sequence
<220> FEATURE:
<223> OTHER INFORMATION: peptide fragment of Sjogren syndrome antigen B
      (autoantigen La)

<400> SEQUENCE: 373

Lys Ile Ile Glu Asp Gln Gln Glu Ser Leu Asn Lys Trp
1               5                   10

<210> SEQ ID NO 374
<211> LENGTH: 11
<212> TYPE: PRT
<213> ORGANISM: Artificial Sequence
<220> FEATURE:
<223> OTHER INFORMATION: peptide fragment of Sjogren syndrome antigen B
      (autoantigen La)

<400> SEQUENCE: 374

Lys Lys Phe Val Glu Thr Pro Gly Gln Lys Tyr
1               5                   10

<210> SEQ ID NO 375
<211> LENGTH: 15
<212> TYPE: PRT
<213> ORGANISM: Artificial Sequence
<220> FEATURE:
<223> OTHER INFORMATION: peptide fragment of Sjogren syndrome antigen B
      (autoantigen La)

<400> SEQUENCE: 375

Lys Leu Asp Glu Gly Trp Val Pro Leu Glu Ile Met Ile Lys Phe
1               5                   10                  15

<210> SEQ ID NO 376
<211> LENGTH: 10
<212> TYPE: PRT
<213> ORGANISM: Artificial Sequence
<220> FEATURE:
<223> OTHER INFORMATION: peptide fragment of Sjogren syndrome antigen B
      (autoantigen La)

<400> SEQUENCE: 376

Lys Leu Glu Glu Asp Ala Glu Met Lys Ser
1               5                   10

<210> SEQ ID NO 377
<211> LENGTH: 12
<212> TYPE: PRT
<213> ORGANISM: Artificial Sequence
<220> FEATURE:
<223> OTHER INFORMATION: peptide fragment of Sjogren syndrome antigen B
      (autoantigen La)

<400> SEQUENCE: 377

Lys Gln Lys Leu Glu Glu Asp Ala Glu Met Lys Ser
1               5                   10

<210> SEQ ID NO 378
<211> LENGTH: 16
<212> TYPE: PRT
<213> ORGANISM: Artificial Sequence
<220> FEATURE:
<223> OTHER INFORMATION: peptide fragment of Sjogren syndrome antigen B
      (autoantigen La)

<400> SEQUENCE: 378

Lys Ser Lys Ala Glu Leu Met Glu Ile Ser Glu Asp Lys Thr Lys Ile
1               5                   10                  15

<210> SEQ ID NO 379
<211> LENGTH: 13
<212> TYPE: PRT
<213> ORGANISM: Artificial Sequence
<220> FEATURE:
<223> OTHER INFORMATION: peptide fragment of Sjogren syndrome antigen B
      (autoantigen La)

<400> SEQUENCE: 379

Lys Tyr Lys Glu Thr Asp Leu Leu Ile Leu Phe Lys Asp
1               5                   10

<210> SEQ ID NO 380
<211> LENGTH: 19
<212> TYPE: PRT
<213> ORGANISM: Artificial Sequence
<220> FEATURE:
<223> OTHER INFORMATION: peptide fragment of Sjogren syndrome antigen B
      (autoantigen La)

<400> SEQUENCE: 380

Lys Tyr Lys Glu Thr Asp Leu Leu Ile Leu Phe Lys Asp Asp Tyr Phe
1               5                   10                  15

Ala Lys Lys

<210> SEQ ID NO 381
<211> LENGTH: 16
<212> TYPE: PRT
<213> ORGANISM: Artificial Sequence
<220> FEATURE:

<223> OTHER INFORMATION: peptide fragment of Sjogren syndrome antigen B
      (autoantigen La)

<400> SEQUENCE: 381

Arg Gly Asp Leu His Ile Leu Phe Ser Asn His Gly Glu Ile Lys Trp
1               5                   10                  15

<210> SEQ ID NO 382
<211> LENGTH: 16
<212> TYPE: PRT
<213> ORGANISM: Artificial Sequence
<220> FEATURE:
<223> OTHER INFORMATION: peptide fragment of Sjogren syndrome antigen B
      (autoantigen La)

<400> SEQUENCE: 382

Arg Leu Thr Thr Asp Phe Asn Val Ile Val Glu Ala Leu Ser Lys Ser
1               5                   10                  15

<210> SEQ ID NO 383
<211> LENGTH: 17
<212> TYPE: PRT
<213> ORGANISM: Artificial Sequence
<220> FEATURE:
<223> OTHER INFORMATION: peptide fragment of Sjogren syndrome antigen B
      (autoantigen La)

<400> SEQUENCE: 383

Arg Asn Lys Glu Val Thr Trp Glu Val Leu Glu Gly Glu Val Glu Lys
1               5                   10                  15

Glu

<210> SEQ ID NO 384
<211> LENGTH: 20
<212> TYPE: PRT
<213> ORGANISM: Artificial Sequence
<220> FEATURE:
<223> OTHER INFORMATION: peptide fragment of Sjogren syndrome antigen B
      (autoantigen La)

<400> SEQUENCE: 384

Arg Ser Pro Ser Lys Pro Leu Pro Glu Val Thr Asp Glu Tyr Lys Asn
1               5                   10                  15

Asp Val Lys Asn
            20

<210> SEQ ID NO 385
<211> LENGTH: 12
<212> TYPE: PRT
<213> ORGANISM: Artificial Sequence
<220> FEATURE:
<223> OTHER INFORMATION: peptide fragment of nudC nuclear distribution
      protein

<400> SEQUENCE: 385

Lys Asp Ala Glu Asn His Glu Ala Gln Leu Lys Asn
1               5                   10

<210> SEQ ID NO 386
<211> LENGTH: 10
<212> TYPE: PRT
<213> ORGANISM: Artificial Sequence
<220> FEATURE:
<223> OTHER INFORMATION: peptide fragment of nudC nuclear distribution
      protein

<400> SEQUENCE: 386

```
Lys Asp Met Val Val Asp Ile Gln Arg Arg
1               5                   10

<210> SEQ ID NO 387
<211> LENGTH: 11
<212> TYPE: PRT
<213> ORGANISM: Artificial Sequence
<220> FEATURE:
<223> OTHER INFORMATION: peptide fragment of nudC nuclear distribution
      protein

<400> SEQUENCE: 387

Lys Glu Leu Thr Asp Glu Glu Ala Glu Arg Leu
1               5                   10

<210> SEQ ID NO 388
<211> LENGTH: 19
<212> TYPE: PRT
<213> ORGANISM: Artificial Sequence
<220> FEATURE:
<223> OTHER INFORMATION: peptide fragment of nudC nuclear distribution
      protein

<400> SEQUENCE: 388

Lys Glu Leu Thr Asp Glu Glu Ala Glu Arg Leu Gln Leu Glu Ile Asp
1               5                   10                  15

Gln Lys Lys

<210> SEQ ID NO 389
<211> LENGTH: 14
<212> TYPE: PRT
<213> ORGANISM: Artificial Sequence
<220> FEATURE:
<223> OTHER INFORMATION: peptide fragment of nudC nuclear distribution
      protein

<400> SEQUENCE: 389

Lys Phe Met Asp Gln His Pro Glu Met Asp Phe Ser Lys Ala
1               5                   10

<210> SEQ ID NO 390
<211> LENGTH: 17
<212> TYPE: PRT
<213> ORGANISM: Artificial Sequence
<220> FEATURE:
<223> OTHER INFORMATION: peptide fragment of nudC nuclear distribution
      protein

<400> SEQUENCE: 390

Lys Gly Gln Pro Ala Ile Ile Asp Gly Glu Leu Tyr Asn Glu Val Lys
1               5                   10                  15

Val

<210> SEQ ID NO 391
<211> LENGTH: 13
<212> TYPE: PRT
<213> ORGANISM: Artificial Sequence
<220> FEATURE:
<223> OTHER INFORMATION: peptide fragment of nudC nuclear distribution
      protein

<400> SEQUENCE: 391

Lys Lys Asp Ala Glu Asn His Glu Ala Gln Leu Lys Asn
1               5                   10
```

-continued

```
<210> SEQ ID NO 392
<211> LENGTH: 17
<212> TYPE: PRT
<213> ORGANISM: Artificial Sequence
<220> FEATURE:
<223> OTHER INFORMATION: peptide fragment of nudC nuclear distribution
      protein

<400> SEQUENCE: 392

Lys Leu Ile Thr Gln Thr Phe Ser His His Asn Gln Leu Ala Gln Lys
1               5                   10                  15

Thr

<210> SEQ ID NO 393
<211> LENGTH: 17
<212> TYPE: PRT
<213> ORGANISM: Artificial Sequence
<220> FEATURE:
<223> OTHER INFORMATION: peptide fragment of nudC nuclear distribution
      protein

<400> SEQUENCE: 393

Lys Leu Lys Pro Asn Leu Gly Asn Gly Ala Asp Leu Pro Asn Tyr Arg
1               5                   10                  15

Trp

<210> SEQ ID NO 394
<211> LENGTH: 11
<212> TYPE: PRT
<213> ORGANISM: Artificial Sequence
<220> FEATURE:
<223> OTHER INFORMATION: peptide fragment of nudC nuclear distribution
      protein

<400> SEQUENCE: 394

Lys Leu Ser Asp Leu Asp Ser Glu Thr Arg Ser
1               5                   10

<210> SEQ ID NO 395
<211> LENGTH: 13
<212> TYPE: PRT
<213> ORGANISM: Artificial Sequence
<220> FEATURE:
<223> OTHER INFORMATION: peptide fragment of nudC nuclear distribution
      protein

<400> SEQUENCE: 395

Lys Ser Met Gly Leu Pro Thr Ser Asp Glu Gln Lys Lys
1               5                   10

<210> SEQ ID NO 396
<211> LENGTH: 16
<212> TYPE: PRT
<213> ORGANISM: Artificial Sequence
<220> FEATURE:
<223> OTHER INFORMATION: peptide fragment of nudC nuclear distribution
      protein

<400> SEQUENCE: 396

Lys Thr Asp Phe Phe Ile Gly Gly Glu Glu Gly Met Ala Glu Lys Leu
1               5                   10                  15

<210> SEQ ID NO 397
<211> LENGTH: 14
<212> TYPE: PRT
<213> ORGANISM: Artificial Sequence
<220> FEATURE:
```

```
<223> OTHER INFORMATION: peptide fragment of nudC nuclear distribution
      protein

<400> SEQUENCE: 397

Lys Val Glu Glu Ser Ser Trp Leu Ile Glu Asp Gly Lys Val
1               5                   10

<210> SEQ ID NO 398
<211> LENGTH: 10
<212> TYPE: PRT
<213> ORGANISM: Artificial Sequence
<220> FEATURE:
<223> OTHER INFORMATION: peptide fragment of nudC nuclear distribution
      protein

<400> SEQUENCE: 398

Lys Val Val Thr Val His Leu Glu Lys Ile
1               5                   10

<210> SEQ ID NO 399
<211> LENGTH: 17
<212> TYPE: PRT
<213> ORGANISM: Artificial Sequence
<220> FEATURE:
<223> OTHER INFORMATION: peptide fragment of nudC nuclear distribution
      protein

<400> SEQUENCE: 399

Arg Lys Thr Asp Phe Phe Ile Gly Gly Glu Glu Gly Met Ala Glu Lys
1               5                   10                  15

Leu

<210> SEQ ID NO 400
<211> LENGTH: 10
<212> TYPE: PRT
<213> ORGANISM: Artificial Sequence
<220> FEATURE:
<223> OTHER INFORMATION: peptide fragment of nudC nuclear distribution
      protein

<400> SEQUENCE: 400

Arg Leu Gln Leu Glu Ile Asp Gln Lys Lys
1               5                   10

<210> SEQ ID NO 401
<211> LENGTH: 13
<212> TYPE: PRT
<213> ORGANISM: Artificial Sequence
<220> FEATURE:
<223> OTHER INFORMATION: peptide fragment of nudC nuclear distribution
      protein

<400> SEQUENCE: 401

Arg Leu Val Ser Ser Asp Pro Glu Ile Asn Thr Lys Lys
1               5                   10

<210> SEQ ID NO 402
<211> LENGTH: 34
<212> TYPE: PRT
<213> ORGANISM: Artificial Sequence
<220> FEATURE:
<223> OTHER INFORMATION: peptide fragment of inosine 5'-monophosphate
      dehydrogenase 2

<400> SEQUENCE: 402

Lys Ala Leu Ala Leu Gly Ala Ser Thr Val Met Met Gly Ser Leu Leu
1               5                   10                  15
```

-continued

Ala Ala Thr Thr Glu Ala Pro Gly Glu Tyr Phe Phe Ser Asp Gly Ile
            20                  25                  30

Arg Leu

<210> SEQ ID NO 403
<211> LENGTH: 22
<212> TYPE: PRT
<213> ORGANISM: Artificial Sequence
<220> FEATURE:
<223> OTHER INFORMATION: peptide fragment of inosine 5'-monophosphate
      dehydrogenase 2

<400> SEQUENCE: 403

Lys Asp Lys Tyr Pro Asn Leu Gln Val Ile Gly Gly Asn Val Val Thr
1               5                   10                  15

Ala Ala Gln Ala Lys Asn
            20

<210> SEQ ID NO 404
<211> LENGTH: 20
<212> TYPE: PRT
<213> ORGANISM: Artificial Sequence
<220> FEATURE:
<223> OTHER INFORMATION: peptide fragment of inosine 5'-monophosphate
      dehydrogenase 2

<400> SEQUENCE: 404

Lys Gly Lys Leu Pro Ile Val Asn Glu Asp Asp Glu Leu Val Ala Ile
1               5                   10                  15

Ile Ala Arg Thr
            20

<210> SEQ ID NO 405
<211> LENGTH: 13
<212> TYPE: PRT
<213> ORGANISM: Artificial Sequence
<220> FEATURE:
<223> OTHER INFORMATION: peptide fragment of inosine 5'-monophosphate
      dehydrogenase 2

<400> SEQUENCE: 405

Lys Asn Leu Ile Asp Ala Gly Val Asp Ala Leu Arg Val
1               5                   10

<210> SEQ ID NO 406
<211> LENGTH: 16
<212> TYPE: PRT
<213> ORGANISM: Artificial Sequence
<220> FEATURE:
<223> OTHER INFORMATION: peptide fragment of inosine 5'-monophosphate
      dehydrogenase 2

<400> SEQUENCE: 406

Lys Arg Glu Asp Leu Val Val Ala Pro Ala Gly Ile Thr Leu Lys Glu
1               5                   10                  15

<210> SEQ ID NO 407
<211> LENGTH: 14
<212> TYPE: PRT
<213> ORGANISM: Artificial Sequence
<220> FEATURE:
<223> OTHER INFORMATION: peptide fragment of inosine 5'-monophosphate
      dehydrogenase 2

<400> SEQUENCE: 407

```
Lys Val Ala Gln Gly Val Ser Gly Ala Val Gln Asp Lys Gly
1               5                   10
```

<210> SEQ ID NO 408
<211> LENGTH: 8
<212> TYPE: PRT
<213> ORGANISM: Artificial Sequence
<220> FEATURE:
<223> OTHER INFORMATION: peptide fragment of inosine 5'-monophosphate
      dehydrogenase 2

<400> SEQUENCE: 408

```
Lys Val Ser Glu Tyr Ala Arg Arg
1               5
```

<210> SEQ ID NO 409
<211> LENGTH: 17
<212> TYPE: PRT
<213> ORGANISM: Artificial Sequence
<220> FEATURE:
<223> OTHER INFORMATION: peptide fragment of inosine 5'-monophosphate
      dehydrogenase 2

<400> SEQUENCE: 409

```
Lys Tyr Glu Gln Gly Phe Ile Thr Asp Pro Val Val Leu Ser Pro Lys
1               5                   10                  15

Asp
```

<210> SEQ ID NO 410
<211> LENGTH: 15
<212> TYPE: PRT
<213> ORGANISM: Artificial Sequence
<220> FEATURE:
<223> OTHER INFORMATION: peptide fragment of inosine 5'-monophosphate
      dehydrogenase 2

<400> SEQUENCE: 410

```
Arg Glu Asp Leu Val Val Ala Pro Ala Gly Ile Thr Leu Lys Glu
1               5                   10                  15
```

<210> SEQ ID NO 411
<211> LENGTH: 21
<212> TYPE: PRT
<213> ORGANISM: Artificial Sequence
<220> FEATURE:
<223> OTHER INFORMATION: peptide fragment of inosine 5'-monophosphate
      dehydrogenase 2

<400> SEQUENCE: 411

```
Arg Phe Gly Val Pro Val Ile Ala Asp Gly Gly Ile Gln Asn Val Gly
1               5                   10                  15

His Ile Ala Lys Ala
            20
```

<210> SEQ ID NO 412
<211> LENGTH: 12
<212> TYPE: PRT
<213> ORGANISM: Artificial Sequence
<220> FEATURE:
<223> OTHER INFORMATION: peptide fragment of inosine 5'-monophosphate
      dehydrogenase 2

<400> SEQUENCE: 412

```
Arg Gly Met Gly Ser Leu Asp Ala Met Asp Lys His
1               5                   10
```

-continued

```
<210> SEQ ID NO 413
<211> LENGTH: 10
<212> TYPE: PRT
<213> ORGANISM: Artificial Sequence
<220> FEATURE:
<223> OTHER INFORMATION: peptide fragment of inosine 5'-monophosphate
      dehydrogenase 2

<400> SEQUENCE: 413

Arg Leu Val Gly Ile Ile Ser Ser Arg Asp
1               5                   10

<210> SEQ ID NO 414
<211> LENGTH: 22
<212> TYPE: PRT
<213> ORGANISM: Artificial Sequence
<220> FEATURE:
<223> OTHER INFORMATION: peptide fragment of inosine 5'-monophosphate
      dehydrogenase 2

<400> SEQUENCE: 414

Arg Arg Phe Gly Val Pro Val Ile Ala Asp Gly Gly Ile Gln Asn Val
1               5                   10                  15

Gly His Ile Ala Lys Ala
            20

<210> SEQ ID NO 415
<211> LENGTH: 20
<212> TYPE: PRT
<213> ORGANISM: Artificial Sequence
<220> FEATURE:
<223> OTHER INFORMATION: peptide fragment of inosine 5'-monophosphate
      dehydrogenase 2

<400> SEQUENCE: 415

Arg Thr Ser Ser Ala Gln Val Glu Gly Gly Val His Ser Leu His Ser
1               5                   10                  15

Tyr Glu Lys Arg
            20

<210> SEQ ID NO 416
<211> LENGTH: 11
<212> TYPE: PRT
<213> ORGANISM: Artificial Sequence
<220> FEATURE:
<223> OTHER INFORMATION: peptide fragment of inosine 5'-monophosphate
      dehydrogenase 2

<400> SEQUENCE: 416

Arg Tyr Phe Ser Glu Ala Asp Lys Ile Lys Val
1               5                   10

<210> SEQ ID NO 417
<211> LENGTH: 15
<212> TYPE: PRT
<213> ORGANISM: Artificial Sequence
<220> FEATURE:
<223> OTHER INFORMATION: peptide fragment of brain abundant, membrane
      attached signal protein 1a

<400> SEQUENCE: 417

Lys Ala Glu Gly Ala Ala Thr Glu Glu Glu Gly Thr Pro Lys Glu
1               5                   10                  15

<210> SEQ ID NO 418
<211> LENGTH: 29
<212> TYPE: PRT
```

```
<213> ORGANISM: Artificial Sequence
<220> FEATURE:
<223> OTHER INFORMATION: peptide fragment of brain abundant, membrane
      attached signal protein 1a

<400> SEQUENCE: 418

Lys Ala Glu Gly Ala Ala Thr Glu Glu Gly Thr Pro Lys Glu Ser
1               5                   10                  15

Glu Pro Gln Ala Ala Ala Glu Pro Ala Glu Ala Lys Glu
            20                  25

<210> SEQ ID NO 419
<211> LENGTH: 15
<212> TYPE: PRT
<213> ORGANISM: Artificial Sequence
<220> FEATURE:
<223> OTHER INFORMATION: peptide fragment of brain abundant, membrane
      attached signal protein 1a

<400> SEQUENCE: 419

Lys Ala Glu Pro Glu Lys Thr Glu Gly Ala Ala Glu Ala Lys Ala
1               5                   10                  15

<210> SEQ ID NO 420
<211> LENGTH: 26
<212> TYPE: PRT
<213> ORGANISM: Artificial Sequence
<220> FEATURE:
<223> OTHER INFORMATION: peptide fragment of brain abundant, membrane
      attached signal protein 1a

<400> SEQUENCE: 420

Lys Ala Glu Pro Pro Lys Ala Pro Glu Gln Glu Gln Ala Ala Pro Gly
1               5                   10                  15

Pro Ala Ala Gly Gly Glu Ala Pro Lys Ala
            20                  25

<210> SEQ ID NO 421
<211> LENGTH: 21
<212> TYPE: PRT
<213> ORGANISM: Artificial Sequence
<220> FEATURE:
<223> OTHER INFORMATION: peptide fragment of brain abundant, membrane
      attached signal protein 1a

<400> SEQUENCE: 421

Lys Ala Pro Glu Gln Glu Gln Ala Ala Pro Gly Pro Ala Ala Gly Gly
1               5                   10                  15

Glu Ala Pro Lys Ala
            20

<210> SEQ ID NO 422
<211> LENGTH: 30
<212> TYPE: PRT
<213> ORGANISM: Artificial Sequence
<220> FEATURE:
<223> OTHER INFORMATION: peptide fragment of brain abundant, membrane
      attached signal protein 1a

<400> SEQUENCE: 422

Lys Ala Gln Gly Pro Ala Ala Ser Ala Glu Glu Pro Lys Pro Val Glu
1               5                   10                  15

Ala Pro Ala Ala Asn Ser Asp Gln Thr Val Thr Val Lys Glu
            20                  25                  30
```

```
<210> SEQ ID NO 423
<211> LENGTH: 16
<212> TYPE: PRT
<213> ORGANISM: Artificial Sequence
<220> FEATURE:
<223> OTHER INFORMATION: peptide fragment of brain abundant, membrane
      attached signal protein 1a

<400> SEQUENCE: 423

Lys Glu Thr Pro Ala Ala Thr Glu Ala Pro Ser Ser Thr Pro Lys Ala
1               5                   10                  15

<210> SEQ ID NO 424
<211> LENGTH: 10
<212> TYPE: PRT
<213> ORGANISM: Artificial Sequence
<220> FEATURE:
<223> OTHER INFORMATION: peptide fragment of brain abundant, membrane
      attached signal protein 1a

<400> SEQUENCE: 424

Lys Gly Tyr Asn Val Asn Asp Glu Lys Ala
1               5                   10

<210> SEQ ID NO 425
<211> LENGTH: 16
<212> TYPE: PRT
<213> ORGANISM: Artificial Sequence
<220> FEATURE:
<223> OTHER INFORMATION: peptide fragment of brain abundant, membrane
      attached signal protein 1a

<400> SEQUENCE: 425

Lys Lys Ala Glu Gly Ala Ala Thr Glu Glu Glu Gly Thr Pro Lys Glu
1               5                   10                  15

<210> SEQ ID NO 426
<211> LENGTH: 16
<212> TYPE: PRT
<213> ORGANISM: Artificial Sequence
<220> FEATURE:
<223> OTHER INFORMATION: peptide fragment of brain abundant, membrane
      attached signal protein 1a

<400> SEQUENCE: 426

Lys Lys Thr Glu Ala Pro Ala Ala Pro Ala Ala Gln Glu Thr Lys Ser
1               5                   10                  15

<210> SEQ ID NO 427
<211> LENGTH: 23
<212> TYPE: PRT
<213> ORGANISM: Artificial Sequence
<220> FEATURE:
<223> OTHER INFORMATION: peptide fragment of brain abundant, membrane
      attached signal protein 1a

<400> SEQUENCE: 427

Lys Ser Asp Gly Ala Pro Ala Ser Asp Ser Lys Pro Gly Ser Ser Glu
1               5                   10                  15

Ala Ala Pro Ser Ser Lys Glu
            20

<210> SEQ ID NO 428
<211> LENGTH: 30
<212> TYPE: PRT
<213> ORGANISM: Artificial Sequence
<220> FEATURE:
<223> OTHER INFORMATION: peptide fragment of eukaryotic translation
``` elongation factor 1 alpha 1

<400> SEQUENCE: 428

Lys Asp Gly Asn Ala Ser Gly Thr Thr Leu Leu Glu Ala Leu Asp Cys
1               5                   10                  15

Ile Leu Pro Pro Thr Arg Pro Thr Asp Lys Pro Leu Arg Leu
            20                  25                  30

<210> SEQ ID NO 429
<211> LENGTH: 9
<212> TYPE: PRT
<213> ORGANISM: Artificial Sequence
<220> FEATURE:
<223> OTHER INFORMATION: peptide fragment of eukaryotic translation
      elongation factor 1 alpha 1

<400> SEQUENCE: 429

Lys Glu Val Ser Thr Tyr Ile Lys Lys
1               5

<210> SEQ ID NO 430
<211> LENGTH: 30
<212> TYPE: PRT
<213> ORGANISM: Artificial Sequence
<220> FEATURE:
<223> OTHER INFORMATION: peptide fragment of eukaryotic translation
      elongation factor 1 alpha 1

<400> SEQUENCE: 430

Lys Ser Gly Asp Ala Ala Ile Val Asp Met Val Pro Gly Lys Pro Met
1               5                   10                  15

Cys Val Glu Ser Phe Ser Asp Tyr Pro Pro Leu Gly Arg Phe
            20                  25                  30

<210> SEQ ID NO 431
<211> LENGTH: 14
<212> TYPE: PRT
<213> ORGANISM: Artificial Sequence
<220> FEATURE:
<223> OTHER INFORMATION: peptide fragment of eukaryotic translation
      elongation factor 1 alpha 1

<400> SEQUENCE: 431

Lys Tyr Tyr Val Thr Ile Ile Asp Ala Pro Gly His Arg Asp
1               5                   10

<210> SEQ ID NO 432
<211> LENGTH: 26
<212> TYPE: PRT
<213> ORGANISM: Artificial Sequence
<220> FEATURE:
<223> OTHER INFORMATION: peptide fragment of eukaryotic translation
      elongation factor 1 alpha 1

<400> SEQUENCE: 432

Arg Val Glu Thr Gly Val Leu Lys Pro Gly Met Val Val Thr Phe Ala
1               5                   10                  15

Pro Val Asn Val Thr Thr Glu Val Lys Ser
            20                  25

<210> SEQ ID NO 433
<211> LENGTH: 8
<212> TYPE: PRT
<213> ORGANISM: Artificial Sequence
<220> FEATURE:
<223> OTHER INFORMATION: peptide fragment of eukaryotic translation elongation factor 1 alpha 1

<400> SEQUENCE: 433

Arg Tyr Glu Glu Ile Val Lys Glu
1               5

<210> SEQ ID NO 434
<211> LENGTH: 12
<212> TYPE: PRT
<213> ORGANISM: Artificial Sequence
<220> FEATURE:
<223> OTHER INFORMATION: peptide fragment of ATP synthase, H+
      transporting, mitochondrial F1 complex, alpha subunit 1

<400> SEQUENCE: 434

Lys Ala Val Asp Ser Leu Val Pro Ile Gly Arg Gly
1               5                   10

<210> SEQ ID NO 435
<211> LENGTH: 13
<212> TYPE: PRT
<213> ORGANISM: Artificial Sequence
<220> FEATURE:
<223> OTHER INFORMATION: peptide fragment of ATP synthase, H+
      transporting, mitochondrial F1 complex, alpha subunit 1

<400> SEQUENCE: 435

Lys Glu Ile Val Thr Asn Phe Leu Ala Gly Phe Glu Ala
1               5                   10

<210> SEQ ID NO 436
<211> LENGTH: 23
<212> TYPE: PRT
<213> ORGANISM: Artificial Sequence
<220> FEATURE:
<223> OTHER INFORMATION: peptide fragment of ATP synthase, H+
      transporting, mitochondrial F1 complex, alpha subunit 1

<400> SEQUENCE: 436

Lys Phe Glu Asn Ala Phe Leu Ser His Val Val Ser Gln His Gln Ala
1               5                   10                  15

Leu Leu Gly Thr Ile Arg Ala
            20

<210> SEQ ID NO 437
<211> LENGTH: 16
<212> TYPE: PRT
<213> ORGANISM: Artificial Sequence
<220> FEATURE:
<223> OTHER INFORMATION: peptide fragment of ATP synthase, H+
      transporting, mitochondrial F1 complex, alpha subunit 1

<400> SEQUENCE: 437

Lys Gly Ile Arg Pro Ala Ile Asn Val Gly Leu Ser Val Ser Arg Val
1               5                   10                  15

<210> SEQ ID NO 438
<211> LENGTH: 22
<212> TYPE: PRT
<213> ORGANISM: Artificial Sequence
<220> FEATURE:
<223> OTHER INFORMATION: peptide fragment of ATP synthase, H+
      transporting, mitochondrial F1 complex, alpha subunit 1

<400> SEQUENCE: 438

Lys Gly Met Ser Leu Asn Leu Glu Pro Asp Asn Val Gly Val Val Val
1               5                   10                  15

Phe Gly Asn Asp Lys Leu
            20

<210> SEQ ID NO 439
<211> LENGTH: 13
<212> TYPE: PRT
<213> ORGANISM: Artificial Sequence
<220> FEATURE:
<223> OTHER INFORMATION: peptide fragment of ATP synthase, H+
      transporting, mitochondrial F1 complex, alpha subunit 1

<400> SEQUENCE: 439

Lys His Ala Leu Ile Ile Tyr Asp Asp Leu Ser Lys Gln
1               5                   10

<210> SEQ ID NO 440
<211> LENGTH: 23
<212> TYPE: PRT
<213> ORGANISM: Artificial Sequence
<220> FEATURE:
<223> OTHER INFORMATION: peptide fragment of ATP synthase, H+
      transporting, mitochondrial F1 complex, alpha subunit 1

<400> SEQUENCE: 440

Lys Gln Gly Gln Tyr Ser Pro Met Ala Ile Glu Glu Gln Val Ala Val
1               5                   10                  15

Ile Tyr Ala Gly Val Arg Gly
            20

<210> SEQ ID NO 441
<211> LENGTH: 15
<212> TYPE: PRT
<213> ORGANISM: Artificial Sequence
<220> FEATURE:
<223> OTHER INFORMATION: peptide fragment of ATP synthase, H+
      transporting, mitochondrial F1 complex, alpha subunit 1

<400> SEQUENCE: 441

Lys Thr Gly Thr Ala Glu Met Ser Ser Ile Leu Glu Glu Arg Ile
1               5                   10                  15

<210> SEQ ID NO 442
<211> LENGTH: 14
<212> TYPE: PRT
<213> ORGANISM: Artificial Sequence
<220> FEATURE:
<223> OTHER INFORMATION: peptide fragment of ATP synthase, H+
      transporting, mitochondrial F1 complex, alpha subunit 1

<400> SEQUENCE: 442

Lys Thr Ser Ile Ala Ile Asp Thr Ile Ile Asn Gln Lys Arg
1               5                   10

<210> SEQ ID NO 443
<211> LENGTH: 15
<212> TYPE: PRT
<213> ORGANISM: Artificial Sequence
<220> FEATURE:
<223> OTHER INFORMATION: peptide fragment of ATP synthase, H+
      transporting, mitochondrial F1 complex, alpha subunit 1

<400> SEQUENCE: 443

Arg Glu Ala Tyr Pro Gly Asp Val Phe Tyr Leu His Ser Arg Leu
1               5                   10                  15

<210> SEQ ID NO 444

<211> LENGTH: 24
<212> TYPE: PRT
<213> ORGANISM: Artificial Sequence
<220> FEATURE:
<223> OTHER INFORMATION: peptide fragment of ATP synthase, H+
      transporting, mitochondrial F1 complex, alpha subunit 1

<400> SEQUENCE: 444

Arg Glu Val Ala Ala Phe Ala Gln Phe Gly Ser Asp Leu Asp Ala Ala
1               5                   10                  15

Thr Gln Gln Leu Leu Ser Arg Gly
            20

<210> SEQ ID NO 445
<211> LENGTH: 17
<212> TYPE: PRT
<213> ORGANISM: Artificial Sequence
<220> FEATURE:
<223> OTHER INFORMATION: peptide fragment of ATP synthase, H+
      transporting, mitochondrial F1 complex, alpha subunit 1

<400> SEQUENCE: 445

Arg Ile Leu Gly Ala Asp Thr Ser Val Asp Leu Glu Glu Thr Gly Arg
1               5                   10                  15

Val

<210> SEQ ID NO 446
<211> LENGTH: 17
<212> TYPE: PRT
<213> ORGANISM: Artificial Sequence
<220> FEATURE:
<223> OTHER INFORMATION: peptide fragment of ATP synthase, H+
      transporting, mitochondrial F1 complex, alpha subunit 1

<400> SEQUENCE: 446

Arg Asn Val Gln Ala Glu Glu Met Val Glu Phe Ser Ser Gly Leu Lys
1               5                   10                  15

Gly

<210> SEQ ID NO 447
<211> LENGTH: 12
<212> TYPE: PRT
<213> ORGANISM: Artificial Sequence
<220> FEATURE:
<223> OTHER INFORMATION: peptide fragment of ATP synthase, H+
      transporting, mitochondrial F1 complex, alpha subunit 1

<400> SEQUENCE: 447

Arg Val Leu Ser Ile Gly Asp Gly Ile Ala Arg Val
1               5                   10

<210> SEQ ID NO 448
<211> LENGTH: 14
<212> TYPE: PRT
<213> ORGANISM: Artificial Sequence
<220> FEATURE:
<223> OTHER INFORMATION: peptide fragment of ATP synthase, H+
      transporting, mitochondrial F1 complex, alpha subunit 1

<400> SEQUENCE: 448

Arg Val Val Asp Ala Leu Gly Asn Ala Ile Asp Gly Lys Gly
1               5                   10

<210> SEQ ID NO 449
<211> LENGTH: 23
<212> TYPE: PRT

<213> ORGANISM: Artificial Sequence
<220> FEATURE:
<223> OTHER INFORMATION: peptide fragment of fascin homolog 1, actin-bundling protein

<400> SEQUENCE: 449

Lys Lys Asn Gly Gln Leu Ala Ala Ser Val Glu Thr Ala Gly Asp Ser
1               5                   10                  15

Glu Leu Phe Leu Met Lys Leu
            20

<210> SEQ ID NO 450
<211> LENGTH: 12
<212> TYPE: PRT
<213> ORGANISM: Artificial Sequence
<220> FEATURE:
<223> OTHER INFORMATION: peptide fragment of fascin homolog 1, actin-bundling protein

<400> SEQUENCE: 450

Lys Leu Ile Asn Arg Pro Ile Ile Val Phe Arg Gly
1               5                   10

<210> SEQ ID NO 451
<211> LENGTH: 22
<212> TYPE: PRT
<213> ORGANISM: Artificial Sequence
<220> FEATURE:
<223> OTHER INFORMATION: peptide fragment of fascin homolog 1, actin-bundling protein

<400> SEQUENCE: 451

Lys Asn Gly Gln Leu Ala Ala Ser Val Glu Thr Ala Gly Asp Ser Glu
1               5                   10                  15

Leu Phe Leu Met Lys Leu
            20

<210> SEQ ID NO 452
<211> LENGTH: 11
<212> TYPE: PRT
<213> ORGANISM: Artificial Sequence
<220> FEATURE:
<223> OTHER INFORMATION: peptide fragment of fascin homolog 1, actin-bundling protein

<400> SEQUENCE: 452

Lys Val Asn Ala Ser Ala Ser Ser Leu Lys Lys
1               5                   10

<210> SEQ ID NO 453
<211> LENGTH: 12
<212> TYPE: PRT
<213> ORGANISM: Artificial Sequence
<220> FEATURE:
<223> OTHER INFORMATION: peptide fragment of fascin homolog 1, actin-bundling protein

<400> SEQUENCE: 453

Lys Val Asn Ala Ser Ala Ser Ser Leu Lys Lys Lys
1               5                   10

<210> SEQ ID NO 454
<211> LENGTH: 12
<212> TYPE: PRT
<213> ORGANISM: Artificial Sequence
<220> FEATURE:
<223> OTHER INFORMATION: peptide fragment of fascin homolog 1, actin-bundling protein

<400> SEQUENCE: 454

Lys Tyr Leu Thr Ala Glu Ala Phe Gly Phe Lys Val
1               5                   10

<210> SEQ ID NO 455
<211> LENGTH: 19
<212> TYPE: PRT
<213> ORGANISM: Artificial Sequence
<220> FEATURE:
<223> OTHER INFORMATION: peptide fragment of fascin homolog 1,
      actin-bundling protein

<400> SEQUENCE: 455

Lys Tyr Trp Thr Leu Thr Ala Thr Gly Gly Val Gln Ser Thr Ala Ser
1               5                   10                  15

Ser Lys Asn

<210> SEQ ID NO 456
<211> LENGTH: 20
<212> TYPE: PRT
<213> ORGANISM: Artificial Sequence
<220> FEATURE:
<223> OTHER INFORMATION: peptide fragment of fascin homolog 1,
      actin-bundling protein

<400> SEQUENCE: 456

Arg Asp Val Pro Trp Gly Val Asp Ser Leu Ile Thr Leu Ala Phe Gln
1               5                   10                  15

Asp Gln Arg Tyr
            20

<210> SEQ ID NO 457
<211> LENGTH: 12
<212> TYPE: PRT
<213> ORGANISM: Artificial Sequence
<220> FEATURE:
<223> OTHER INFORMATION: peptide fragment of fascin homolog 1,
      actin-bundling protein

<400> SEQUENCE: 457

Arg Phe Leu Ile Val Ala His Asp Asp Gly Arg Trp
1               5                   10

<210> SEQ ID NO 458
<211> LENGTH: 30
<212> TYPE: PRT
<213> ORGANISM: Artificial Sequence
<220> FEATURE:
<223> OTHER INFORMATION: peptide fragment of fascin homolog 1,
      actin-bundling protein

<400> SEQUENCE: 458

Arg Lys Val Thr Gly Thr Leu Asp Ala Asn Arg Ser Ser Tyr Asp Val
1               5                   10                  15

Phe Gln Leu Glu Phe Asn Asp Gly Ala Tyr Asn Ile Lys Asp
            20                  25                  30

<210> SEQ ID NO 459
<211> LENGTH: 18
<212> TYPE: PRT
<213> ORGANISM: Artificial Sequence
<220> FEATURE:
<223> OTHER INFORMATION: peptide fragment of fascin homolog 1,
      actin-bundling protein

<400> SEQUENCE: 459

Arg Leu Val Ala Arg Pro Glu Pro Ala Thr Gly Tyr Thr Leu Glu Phe
1               5                   10                  15

Arg Ser

<210> SEQ ID NO 460
<211> LENGTH: 26
<212> TYPE: PRT
<213> ORGANISM: Artificial Sequence
<220> FEATURE:
<223> OTHER INFORMATION: peptide fragment of fascin homolog 1,
      actin-bundling protein

<400> SEQUENCE: 460

Arg Gln Gly Met Asp Leu Ser Ala Asn Gln Asp Glu Glu Thr Asp Gln
1               5                   10                  15

Glu Thr Phe Gln Leu Glu Ile Asp Arg Asp
            20                  25

<210> SEQ ID NO 461
<211> LENGTH: 29
<212> TYPE: PRT
<213> ORGANISM: Artificial Sequence
<220> FEATURE:
<223> OTHER INFORMATION: peptide fragment of fascin homolog 1,
      actin-bundling protein

<400> SEQUENCE: 461

Arg Gln Gly Met Asp Leu Ser Ala Asn Gln Asp Glu Glu Thr Asp Gln
1               5                   10                  15

Glu Thr Phe Gln Leu Glu Ile Asp Arg Asp Thr Lys Lys
            20                  25

<210> SEQ ID NO 462
<211> LENGTH: 20
<212> TYPE: PRT
<213> ORGANISM: Artificial Sequence
<220> FEATURE:
<223> OTHER INFORMATION: peptide fragment of fascin homolog 1,
      actin-bundling protein

<400> SEQUENCE: 462

Arg Ser Ser Tyr Asp Val Phe Gln Leu Glu Phe Asn Asp Gly Ala Tyr
1               5                   10                  15

Asn Ile Lys Asp
            20

<210> SEQ ID NO 463
<211> LENGTH: 11
<212> TYPE: PRT
<213> ORGANISM: Artificial Sequence
<220> FEATURE:
<223> OTHER INFORMATION: peptide fragment of fascin homolog 1,
      actin-bundling protein

<400> SEQUENCE: 463

Arg Trp Ser Leu Gln Ser Glu Ala His Arg Arg
1               5                   10

<210> SEQ ID NO 464
<211> LENGTH: 11
<212> TYPE: PRT
<213> ORGANISM: Artificial Sequence
<220> FEATURE:

<223> OTHER INFORMATION: peptide fragment of fascin homolog 1,
     actin-bundling protein

<400> SEQUENCE: 464

Arg Tyr Ser Val Gln Thr Ala Asp His Arg Phe
1               5                   10

<210> SEQ ID NO 465
<211> LENGTH: 10
<212> TYPE: PRT
<213> ORGANISM: Artificial Sequence
<220> FEATURE:
<223> OTHER INFORMATION: peptide fragment of eukaryotic translation
     initiation factor 4A3

<400> SEQUENCE: 465

Lys Glu Gln Ile Tyr Asp Val Tyr Arg Tyr
1               5                   10

<210> SEQ ID NO 466
<211> LENGTH: 9
<212> TYPE: PRT
<213> ORGANISM: Artificial Sequence
<220> FEATURE:
<223> OTHER INFORMATION: peptide fragment of eukaryotic translation
     initiation factor 4A3

<400> SEQUENCE: 466

Lys Phe Met Thr Asp Pro Ile Arg Ile
1               5

<210> SEQ ID NO 467
<211> LENGTH: 16
<212> TYPE: PRT
<213> ORGANISM: Artificial Sequence
<220> FEATURE:
<223> OTHER INFORMATION: peptide fragment of eukaryotic translation
     initiation factor 4A3

<400> SEQUENCE: 467

Lys Gly Arg Asp Val Ile Ala Gln Ser Gln Ser Gly Thr Gly Lys Thr
1               5                   10                  15

<210> SEQ ID NO 468
<211> LENGTH: 16
<212> TYPE: PRT
<213> ORGANISM: Artificial Sequence
<220> FEATURE:
<223> OTHER INFORMATION: peptide fragment of eukaryotic translation
     initiation factor 4A3

<400> SEQUENCE: 468

Lys Leu Asp Tyr Gly Gln His Val Val Ala Gly Thr Pro Gly Arg Val
1               5                   10                  15

<210> SEQ ID NO 469
<211> LENGTH: 15
<212> TYPE: PRT
<213> ORGANISM: Artificial Sequence
<220> FEATURE:
<223> OTHER INFORMATION: peptide fragment of eukaryotic translation
     initiation factor 4A3

<400> SEQUENCE: 469

Lys Met Leu Val Leu Asp Glu Ala Asp Glu Met Leu Asn Lys Gly
1               5                   10                  15

```
<210> SEQ ID NO 470
<211> LENGTH: 12
<212> TYPE: PRT
<213> ORGANISM: Artificial Sequence
<220> FEATURE:
<223> OTHER INFORMATION: peptide fragment of eukaryotic translation
      initiation factor 4A3

<400> SEQUENCE: 470

Lys Arg Asp Glu Leu Thr Leu Glu Gly Ile Lys Gln
1               5                   10

<210> SEQ ID NO 471
<211> LENGTH: 11
<212> TYPE: PRT
<213> ORGANISM: Artificial Sequence
<220> FEATURE:
<223> OTHER INFORMATION: peptide fragment of eukaryotic translation
      initiation factor 4A3

<400> SEQUENCE: 471

Lys Arg Lys Val Asp Trp Leu Thr Glu Lys Met
1               5                   10

<210> SEQ ID NO 472
<211> LENGTH: 22
<212> TYPE: PRT
<213> ORGANISM: Artificial Sequence
<220> FEATURE:
<223> OTHER INFORMATION: peptide fragment of eukaryotic translation
      initiation factor 4A3

<400> SEQUENCE: 472

Arg Asp Ile Glu Gln Tyr Tyr Ser Thr Gln Ile Asp Glu Met Pro Met
1               5                   10                  15

Asn Val Ala Asp Leu Ile
            20

<210> SEQ ID NO 473
<211> LENGTH: 14
<212> TYPE: PRT
<213> ORGANISM: Artificial Sequence
<220> FEATURE:
<223> OTHER INFORMATION: peptide fragment of eukaryotic translation
      initiation factor 4A3

<400> SEQUENCE: 473

Arg Asp Val Ile Ala Gln Ser Gln Ser Gly Thr Gly Lys Thr
1               5                   10

<210> SEQ ID NO 474
<211> LENGTH: 18
<212> TYPE: PRT
<213> ORGANISM: Artificial Sequence
<220> FEATURE:
<223> OTHER INFORMATION: peptide fragment of eukaryotic translation
      initiation factor 4A3

<400> SEQUENCE: 474

Arg Glu Ala Asn Phe Thr Val Ser Ser Met His Gly Asp Met Pro Gln
1               5                   10                  15

Lys Glu

<210> SEQ ID NO 475
<211> LENGTH: 10
<212> TYPE: PRT
<213> ORGANISM: Artificial Sequence
```

<220> FEATURE:
<223> OTHER INFORMATION: peptide fragment of eukaryotic translation
      initiation factor 4A3

<400> SEQUENCE: 475

Arg Glu Leu Ala Val Gln Ile Gln Lys Gly
1               5                   10

<210> SEQ ID NO 476
<211> LENGTH: 13
<212> TYPE: PRT
<213> ORGANISM: Artificial Sequence
<220> FEATURE:
<223> OTHER INFORMATION: peptide fragment of eukaryotic translation
      initiation factor 4A3

<400> SEQUENCE: 476

Arg Glu Thr Gln Ala Leu Ile Leu Ala Pro Thr Arg Glu
1               5                   10

<210> SEQ ID NO 477
<211> LENGTH: 18
<212> TYPE: PRT
<213> ORGANISM: Artificial Sequence
<220> FEATURE:
<223> OTHER INFORMATION: peptide fragment of eukaryotic translation
      initiation factor 4A3

<400> SEQUENCE: 477

Arg Gly Ile Tyr Ala Tyr Gly Phe Glu Lys Pro Ser Ala Ile Gln Gln
1               5                   10                  15

Arg Ala

<210> SEQ ID NO 478
<211> LENGTH: 21
<212> TYPE: PRT
<213> ORGANISM: Artificial Sequence
<220> FEATURE:
<223> OTHER INFORMATION: peptide fragment of eukaryotic translation
      initiation factor 4A3

<400> SEQUENCE: 478

Arg Gly Leu Asp Val Pro Gln Val Ser Leu Ile Ile Asn Tyr Asp Leu
1               5                   10                  15

Pro Asn Asn Arg Glu
            20

<210> SEQ ID NO 479
<211> LENGTH: 17
<212> TYPE: PRT
<213> ORGANISM: Artificial Sequence
<220> FEATURE:
<223> OTHER INFORMATION: peptide fragment of eukaryotic translation
      initiation factor 4A3

<400> SEQUENCE: 479

Arg Lys Leu Asp Tyr Gly Gln His Val Val Ala Gly Thr Pro Gly Arg
1               5                   10                  15

Val

<210> SEQ ID NO 480
<211> LENGTH: 11
<212> TYPE: PRT
<213> ORGANISM: Artificial Sequence
<220> FEATURE:
<223> OTHER INFORMATION: peptide fragment of eukaryotic translation

```
                initiation factor 4A3

<400> SEQUENCE: 480

Arg Leu Leu Lys Glu Glu Asp Met Thr Lys Val
1               5                   10

<210> SEQ ID NO 481
<211> LENGTH: 12
<212> TYPE: PRT
<213> ORGANISM: Artificial Sequence
<220> FEATURE:
<223> OTHER INFORMATION: peptide fragment of eukaryotic translation
      initiation factor 4A3

<400> SEQUENCE: 481

Arg Val Leu Ile Ser Thr Asp Val Trp Ala Arg Gly
1               5                   10
```